United States Patent
Rey et al.

(10) Patent No.: US 10,842,152 B2
(45) Date of Patent: Nov. 24, 2020

(54) ISOTHIAZOLO-BASED BICYCLES, PROCESSES FOR THEIR PREPARATION AND THEIR USE AS HERBICIDES AND/OR PLANT GROWTH REGULATORS

(71) Applicant: Bayer CropScience Aktiengesellschaft, Monheim am Rhein (FR)

(72) Inventors: Jullien Rey, Sierentz (FR); Joerg Tiebes, Frankfurt (DE); Marc Mosrin, Cologne (DE); Thomas Droege, Langenfeld (DE); Hansjoerg Dietrich, Liederbach am Taunus (DE); Anu Bheemaiah Machettira, Frankfurt am Main (DE); Elmar Gatzweiler, Bad Nauheim (DE); Christopher Hugh Rosinger, Hofheim (DE); Dirk Schmutzler, Hattersheim (DE); Daniela Portz, Vettweiss (DE); Kerstin Ilg, Cologne (DE); Philippe Rinolfi, Chatillon D Azergues (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/627,983

(22) PCT Filed: Jun. 28, 2018

(86) PCT No.: PCT/EP2018/067378
§ 371 (c)(1),
(2) Date: Dec. 31, 2019

(87) PCT Pub. No.: WO2019/007795
PCT Pub. Date: Jan. 10, 2019

(65) Prior Publication Data
US 2020/0178532 A1 Jun. 11, 2020

(30) Foreign Application Priority Data
Jul. 3, 2017 (EP) .................................... 17179255

(51) Int. Cl.
*A01N 43/90* (2006.01)
*C07D 513/04* (2006.01)

(52) U.S. Cl.
CPC ........... *A01N 43/90* (2013.01); *C07D 513/04* (2013.01)

(58) Field of Classification Search
CPC .............................. A01N 43/90; C07D 513/04
See application file for complete search history.

(56) References Cited

U.S. PATENT DOCUMENTS

| | | | |
|---|---|---|---|
| 4,631,211 A | 12/1986 | Houghten | |
| 7,838,463 B2 | 11/2010 | Bickers et al. | |
| 8,138,118 B2 | 3/2012 | Bickers et al. | |
| 9,102,623 B2 | 8/2015 | Ziemer et al. | |
| 9,512,128 B2 | 12/2016 | Alig et al. | |
| 2004/0224844 A1 | 11/2004 | Bickers et al. | |
| 2005/0037922 A1 | 2/2005 | Bickers et al. | |
| 2005/0049145 A1 | 3/2005 | Bickers et al. | |
| 2005/0256000 A1 | 11/2005 | Schaper et al. | |
| 2008/0269052 A1 | 10/2008 | Rosinger et al. | |
| 2008/0269059 A1 | 10/2008 | Ziemer et al. | |
| 2011/0065698 A1* | 3/2011 | Pierre ....................... A61P 3/10 514/232.8 |
| 2011/0143939 A1 | 6/2011 | Schaper et al. | |
| 2012/0252670 A1 | 10/2012 | Ziemer et al. | |
| 2015/0344499 A1 | 12/2015 | Alig et al. | |
| 2019/0037848 A1 | 2/2019 | Tiebes et al. | |
| 2019/0110476 A1 | 4/2019 | Bernier et al. | |

FOREIGN PATENT DOCUMENTS

| | | |
|---|---|---|
| CN | 103288855 B | 3/2015 |
| WO | 9107874 A1 | 6/1991 |
| WO | 9108202 A1 | 6/1991 |
| WO | 9507897 A1 | 3/1995 |
| WO | 9745016 A1 | 12/1997 |
| WO | 9813361 A1 | 4/1998 |
| WO | 9827049 A1 | 6/1998 |
| WO | 9838856 A1 | 9/1998 |
| WO | 9900020 A1 | 1/1999 |
| WO | 9916744 A1 | 4/1999 |
| WO | 0234048 A1 | 5/2002 |
| WO | 2004084631 A1 | 10/2004 |
| WO | 2005015994 A1 | 2/2005 |
| WO | 2005016001 A1 | 2/2005 |
| WO | 2005112630 A1 | 12/2005 |
| WO | 2007023719 A1 | 3/2007 |
| WO | 2007023764 A1 | 3/2007 |
| WO | 2008131860 A2 | 11/2008 |
| WO | 2008131861 A1 | 11/2008 |
| WO | 2014095979 A1 | 6/2014 |
| WO | 2016102420 A2 | 6/2016 |
| WO | 2016102435 A2 | 6/2016 |

OTHER PUBLICATIONS

PCT International Search Report for PCT/EP2018/067378, dated Aug. 21, 2018.

\* cited by examiner

Primary Examiner — Andrew S Rosenthal
(74) Attorney, Agent, or Firm — McBee Moore & Vanik IP, LLC

(57) ABSTRACT

The invention relates to the technical field of the herbicides and/or plant growth regulators. Specifically, the invention primarily relates to novel substituted isothiazolopyridones, and compositions comprising said novel substituted isothiazolopyridones. Further, the present invention relates to processes for the preparation said novel substituted isothiazolopyridones and their use as herbicides and/or plant growth regulators.

8 Claims, No Drawings

US 10,842,152 B2

ISOTHIAZOLO-BASED BICYCLES, PROCESSES FOR THEIR PREPARATION AND THEIR USE AS HERBICIDES AND/OR PLANT GROWTH REGULATORS

BACKGROUND

Field

The invention relates to the technical field of herbicides and/or plant growth regulators. Specifically, the invention relates to novel substituted isothiazolopyridones, and compositions comprising said novel substituted isothiazolopyridones. Further, the present invention relates to processes for the preparation of said novel substituted isothiazolopyridones and their use as herbicides and/or plant growth regulators.

Description of Related Art

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavourable profile.

Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities.

The prior art discloses several isothiazoles and isothiazolamides:

WO 2016/102435 discloses isothiazolamides and their use as fungicides.

WO 2016/102420 discloses isothiazolamides and their use as herbicides and/or plant growth regulators.

In their application, herbicides known to date for controlling harmful plants or unwanted vegetation may have some disadvantages, be it (a) that they have no or else insufficient herbicidal activity against specific harmful plants, (b) that the spectrum of harmful plants which can be controlled with the herbicides is not broad enough, and/or (c) that the selectivity of herbicides in and the compatibility with crop plants is too low, thereby causing unwanted damage and/or unwanted reduced harvest yields of the crops.

Thus, there is still a need for alternative herbicides, in particular highly active herbicides, in particular useful at low application rates and/or having good compatibility with crop plants, for the selective application in plant crops or use on non-crop land. It is also desirable to provide alternative chemical active compounds which may be used in an advantageous manner as herbicides or plant growth regulators.

SUMMARY

It is therefore an objective of the present invention to provide compounds having herbicidal activity which are highly effective against economically important harmful plants even at relatively low application rates and that can be used selectively in crop plants.

It has now been found that the compounds of the following formulae (G1) and (G2) and/or the salts thereof meet said objective(s).

The present invention primarily relates to compounds of the formulae (G1) and (G2) and/or salts thereof

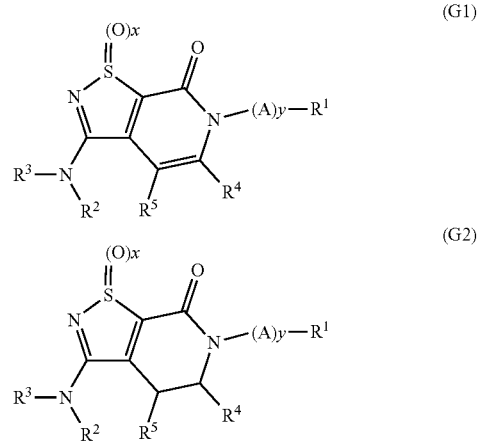

in which
A is $CR^6R^7$,
x is 0, 1 or 2,
$R^1$ is hydrogen, $(C_1-C_8)$-alkyl, $(C_2-C_8)$-alkenyl, $(C_2-C_8)$-alkynyl, $(C_1-C_8)$-alkoxy, $(C_1-C_8)$-alkoxy-$(C_1-C_8)$-alkyl, $(C_1-C_8)$-alkylthio, $(C_3-C_8)$-cycloalkyl, $(C_3-C_8)$-cycloalkenyl, $(C_3-C_8)$-cycloalkyl-$(C_1-C_8)$-alkyl, $(C_3-C_8)$-cycloalkenyl-$(C_1-C_8)$-alkyl, $(C_3-C_8)$-cycloalkoxy, $(C_3-C_8)$-cycloalkyl-$(C_1-C_5)$-alkoxy, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, aryloxy, heteroaryloxy, heterocyclyloxy, wherein all these residues are unsubstituted or substituted by one or more residues from the group consisting of halogen, nitro, hydroxyl, cyano, $NR^{13}R^{14}$, $(C_1-C_8)$-alkyl, $(C_1-C_8)$-haloalkyl, $(C_1-C_8)$-alkoxy, $(C_1-C_8)$-haloalkoxy, $(C_1-C_8)$-alkylthio, $(C_1-C_8)$-alkylsulphinyl, $(C_1-C_8)$-alkylsulphonyl, $(C_1-C_8)$-haloalkylthio, $(C_1-C_8)$-haloalkylsulphinyl, $(C_1-C_8)$-haloalkylsulphonyl, $(C_1-C_8)$-alkoxycarbonyl, $(C_1-C_8)$-haloalkoxycarbonyl, $(C_1-C_8)$-alkylcarboxy, $(C_3-C_8)$-cycloalkyl, $(C_3-C_8)$-cycloalkyl-$(C_1-C_8)$-alkyl, $(C_1-C_8)$-alkoxycarbonyl-$(C_1-C_8)$-alkyl, hydroxycarbonyl, hydroxycarbonyl-$(C_1-C_8)$-alkyl, $R^{13}R^{14}N$-carbonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$,
$R^2$, $R^3$ are each independently hydrogen, $(C_1-C_8)$-alkyl, $(C_2-C_8)$-alkenyl, $(C_2-C_8)$-alkynyl, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_1-C_8)$-alkoxyphenyl, $(C_1-C_8)$-alkoxyphenyl-$(C_1-C_8)$-alkyl, $(C_1-C_8)$-alkoxy-$(C_1-C_8)$-alkylcarbonyl, $(C_1-C_8)$-alkoxy-$(C_1-C_8)$-alkoxy-$(C_1-C_8)$-alkylcarbonyl, $(C_1-C_8)$-alkoxycarbonyl, $(C_2-C_8)$-alkenyloxycarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, $R^{13}R^{14}N$-carbonyl, $(C_1-C_8)$-alkylthio, $(C_1-C_8)$-alkylthiocarbonyl, $(C_1-C_8)$-alkylsulphinyl, $(C_1-C_8)$-alkylsulphonyl, $(C_1-C_8)$- alkylthio-($C_1$-$C_8$)-alkyl, ($C_1$-$C_8$)-alkylsulphinyl-($C_1$-$C_8$)-alkyl, ($C_1$-$C_8$)-alkylsulphonyl-($C_1$-$C_8$)-alkyl, ($C_1$-$C_8$)-alkylthio-($C_1$-$C_8$)-alkylcarbonyl, ($C_1$-$C_8$)-alkylsulphinyl-($C_1$-$C_8$)-alkylcarbonyl, ($C_1$-$C_8$)-alkylsulphonyl-($C_1$-$C_8$)-alkylcarbonyl, ($C_1$-$C_8$)-alkoxycarbonyl-($C_1$-$C_8$)-alkylcarbonyl, ($C_3$-$C_8$)-cycloalkyl, ($C_3$-$C_8$)-cycloalkenyl, ($C_3$-$C_8$)-cycloalkyl-($C_1$-$C_8$)-alkyl, ($C_3$-$C_8$)-cycloalkenyl-($C_1$-$C_8$)-alkyl, ($C_3$-$C_8$)-cycloalkylcarbonyl, ($C_3$-$C_8$)-cycloalkenylcarbonyl, ($C_3$-$C_8$)-cycloalkyl-($C_1$-$C_8$)-alkylcarbonyl, ($C_3$-$C_8$)-cycloalkenyl-($C_1$-$C_8$)-alkylcarbonyl, aryl, aryl-($C_1$-$C_8$)-alkyl, heteroaryl, heteroaryl-($C_1$-$C_8$)-alkyl, heterocyclyl, heterocyclyl-($C_1$-$C_8$)-alkyl, arylcarbonyl, aryl-($C_1$-$C_8$)-alkylcarbonyl, heteroarylcarbonyl, heteroaryl-($C_1$-$C_8$)-alkylcarbonyl, heterocyclylcarbonyl, or heterocyclyl-($C_1$-$C_8$)-alkylcarbonyl, wherein all these residues are unsubstituted or substituted by one or more residues from the group consisting of halogen, nitro, hydroxyl, cyano, $NR^{13}R^{14}$, ($C_1$-$C_8$)-alkyl, ($C_1$-$C_8$)-haloalkyl, ($C_1$-$C_8$)-alkoxy, ($C_1$-$C_8$)-haloalkoxy, ($C_1$-$C_8$)-alkylthio, ($C_1$-$C_8$)-alkylsulphinyl, ($C_1$-$C_8$)-alkylsulphonyl, ($C_1$-$C_8$)-haloalkylthio, ($C_1$-$C_8$)-haloalkylsulphinyl, ($C_1$-$C_8$)-haloalkylsulphonyl, ($C_1$-$C_8$)-alkoxycarbonyl, ($C_1$-$C_8$)-haloalkoxycarbonyl, ($C_1$-$C_8$)-alkylcarboxy, ($C_3$-$C_8$)-cycloalkyl, ($C_3$-$C_8$)-cycloalkyl-($C_1$-$C_8$)-alkyl, ($C_1$-$C_8$)-alkoxycarbonyl-($C_1$-$C_8$)-alkyl, hydroxycarbonyl, hydroxycarbonyl-($C_1$-$C_4$)-alkyl, $R^{13}R^{14}$N-carbonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $NR^2R^3$ is —N=$CR^8R^9$ or —N=$S(O)_n R^{10} R^{11}$, $R^4$, $R^5$ are each independently hydrogen, formyl, cyano, halogen, oxytetrahydropyranmethyl, ($C_1$-$C_8$)-alkoxycarbonyl, imino-($C_1$-$C_8$)-alkyl, ($C_1$-$C_8$)-alkylcarbonyloxy, ($C_1$-$C_6$)-alkylcarbonyloxy-($C_1$-$C_6$)-alkyl, ($C_1$-$C_8$)-alkylsilyl, ($C_2$-$C_6$)-alkenylcarbonyl, ($C_2$-$C_6$)-alkynylcarbonyl, ($C_3$-$C_8$)-cycloalkyl-($C_1$-$C_8$)-alkylaminocarbonyl, aminocarbonyl, ($C_1$-$C_8$)-alkylcarboxy, ($C_1$-$C_8$)-alkyl, ($C_2$-$C_8$)-alkenyl, ($C_2$-$C_8$)-alkynyl, $NR^{13}R^{14}$, $R^{13}R^{14}N$—($C_1$-$C_8$)-alkyl, ($C_1$-$C_8$)-alkoxy, ($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkylthio, ($C_1$-$C_8$)-alkylsulphinyl, ($C_1$-$C_8$)-alkylsulphonyl, ($C_1$-$C_8$)-alkylthio-($C_1$-$C_8$)-alkyl, ($C_1$-$C_8$)-alkylsulphinyl-($C_1$-$C_8$)-alkyl, ($C_1$-$C_8$)-alkylsulphonyl-($C_1$-$C_8$)-alkyl, ($C_3$-$C_8$)-cycloalkyl, ($C_3$-$C_8$)-cycloalkenyl, ($C_3$-$C_8$)-cycloalkyl-($C_1$-$C_8$)-alkyl, ($C_3$-$C_8$)-cycloalkenyl-($C_1$-$C_8$)-alkyl, ($C_3$-$C_8$)-cycloalkoxy, ($C_3$-$C_8$)-cycloalkyl-($C_1$-$C_8$)-alkoxy, aryl, aryl-($C_1$-$C_8$)-alkyl, heteroaryl, heteroaryl-($C_1$-$C_8$)-alkyl, heterocyclyl, heterocyclyl-($C_1$-$C_8$)-alkyl, aryloxy, heteroaryloxy, heterocyclyloxy, wherein all these residues are unsubstituted or substituted by one or more residues from the group consisting of halogen, hydroxyl, cyano, ($C_1$-$C_6$)-alkoxy, ($C_1$-$C_6$)-alkyl, ($C_1$-$C_8$)-haloalkyl, ($C_1$-$C_8$)-haloalkoxy, ($C_1$-$C_8$)-alkylthio, ($C_1$-$C_8$)-alkylsulphinyl, ($C_1$-$C_8$)-alkylsulphonyl, ($C_1$-$C_8$)-haloalkylthio, ($C_1$-$C_8$)-haloalkylsulphinyl, ($C_1$-$C_8$)-haloalkylsulphonyl, ($C_1$-$C_6$)-alkoxycarbonyl, ($C_1$-$C_6$)-alkoxycarbonyl-($C_1$-$C_6$)-alkoxy, ($C_3$-$C_6$)-cycloalkyl-($C_1$-$C_6$)-alkoxyimino, ($C_2$-$C_6$)-alkenyloxyimino, ($C_1$-$C_6$)-alkyloxyimino, aminocarbonyl and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, provided that $R^4$ and $R^5$ are not hydrogen at the same time, $R^6$, $R^7$ are each independently hydrogen, cyano, halogen, ($C_1$-$C_8$)-alkyl, ($C_2$-$C_8$)-alkenyl, ($C_2$-$C_8$)-alkynyl, or ($C_3$-$C_8$)-cycloalkyl, $R^8$, $R^9$ are each independently hydrogen, ($C_1$-$C_8$)-alkyl, ($C_2$-$C_8$)-alkenyl, ($C_2$-$C_8$)-alkynyl, ($C_2$-$C_8$)-alkenyloxy, ($C_2$-$C_8$)-alkynyloxy, $NR^{13}R^{14}$, ($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkylthio-($C_1$-$C_8$)-alkyl, ($C_1$-$C_8$)-alkylsulphinyl-($C_1$-$C_8$)-alkyl, ($C_1$-$C_8$)-alkylsulphonyl-($C_1$-$C_8$)-alkyl, ($C_3$-$C_8$)-cycloalkyl, ($C_3$-$C_8$)-cycloalkenyl, ($C_3$-$C_8$)-cycloalkyl-($C_1$-$C_8$)-alkyl, ($C_3$-$C_8$)-cycloalkenyl-($C_1$-$C_8$)-alkyl, aryl, aryl-($C_1$-$C_8$)-alkyl, heteroaryl, heteroaryl-($C_1$-$C_8$)-alkyl, heterocyclyl, heterocyclyl-($C_1$-$C_8$)-alkyl, wherein all these residues are unsubstituted or substituted by one or more residues from the group consisting of halogen, nitro, hydroxyl, cyano, ($C_1$-$C_8$)-alkyl, ($C_1$-$C_8$)-haloalkyl, ($C_1$-$C_8$)-alkoxy, ($C_1$-$C_8$)-haloalkoxy, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, $R^{10}$, $R^{11}$ are each independently hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, phenyl, phenyl-($C_1$-$C_6$)-alkyl, pyridinyl, furanyl, thienyl, pyridinyl-($C_1$-$C_6$)-alkyl, thienyl-($C_1$-$C_6$)-alkyl, furanyl-($C_1$-$C_6$)-alkyl, heterocyclyl, heterocyclyl-($C_1$-$C_6$)-alkyl, wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, and wherein heterocyclyl has q oxo groups, and wherein each of the aforementioned heterocyclic residues, in addition to the carbon atoms, has in each case p ring members from the group consisting of $N(R^2)_m$, O and $S(O)_n$, or $R^{10}$ and $R^{11}$, together with the sulphur atom to which they are attached, form a 3- to 6-membered unsaturated, partially saturated or saturated ring, which comprises in each case, in addition to the carbon atoms and in addition to the sulphur atom, p ring members from the group consisting of $N(R^2)_m$, O and $S(O)_n$, and wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl or ($C_1$-$C_6$)-alkylsulphonyl, $R^{12}$ is hydrogen, ($C_1$-$C_6$)-alkyl or ($C_1$-$C_6$)-alkylcarbonyl, $R^{13}$, $R^{14}$ are each independently hydrogen, ($C_1$-$C_6$)-alkyl, wherein these residues are unsubstituted or substituted by one or more residues from the group consisting of halogen, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, or $R^{13}$ and $R^{14}$, together with the nitrogen atom to which they are attached, form a 3- to 8-membered unsaturated, partially saturated or saturated ring, n is independently selected from 0, 1 or 2,
m is independently selected from 0 or 1,
p is independently selected from 0, 1, 2 or 3,
q is independently selected from 0, 1 or 2,
y is 0 or 1.

DETAILED DESCRIPTION OF A PREFERRED EMBODIMENT

Salts for the purposes of the present invention are preferably agrochemically active salts of the compounds according to the invention.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Solvates of the compounds of the invention or their salts are stoichiometric compositions of the compounds with solvents.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

Not included are combinations which are against natural laws and which the person skilled in the art would therefore exclude based on his/her expert knowledge. Ring structures having three or more adjacent oxygen atoms, for example, are excluded.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. Here, the metals can be present in the various valencies that they can assume.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions. The geometric isomers can be separated according to general methods, which are known per se by the man ordinary skilled in the art.

Unless otherwise stated, the following definitions apply for the substituents and residues used throughout this specification and claims: Halogen represents radicals of fluorine, chlorine, bromine and iodine. Preference is given to the radicals of fluorine and chlorine.

Alkyl represents a straight-chain or branched saturated hydrocarbon radical having 1 to 8 carbon atoms. Non-limiting examples include methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl and 1-methyl-2-cyclopropylethyl. Preference is given to ($C_1$-$C_4$)-alkyl representing a straight-chain or branched saturated hydrocarbon radical having 1 to 4 carbon atoms, such as methyl, ethyl, n-propyl, isopropyl, n-butyl, iso-butyl, sec-butyl, tert.-butyl.

Haloalkyl represents in general an alkyl-radical having 1 to 8 carbon atoms, in which 1 up to all hydrogen atoms are replaced by halogen atoms. Non-limiting examples include chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

Cycloalkyl represents a monocyclic saturated hydrocarbon radical having 3 to 8, preferably 3 to 6 carbon atoms. Non-limiting examples include cyclopropyl, cyclobutyl, cyclopentyl, cyclohexyl, cycloheptyl and cyclooctyl.

Halocycloalkyl represents in general a monocyclic saturated hydrocarbon radical having 3 to 8, preferably 3 to 6 carbon atoms, in which 1 up to 7 hydrogen atoms are replaced by halogen atoms. Non-limiting examples include chlorocyclopropyl, dichlorocyclopropyl, dibromocyclopropyl, fluorocyclopropyl, chlorocyclopentyl and chlorocyclohexyl.

Alkenyl represents an unsaturated, straight-chain or branched hydrocarbon radical having 2 to 8, preferably 2 to 6, carbon atoms and one or two double bonds in any position. Non-limiting examples include ethenyl, prop-1- enyl, prop-2-enyl, 1-methylethenyl, but-1-enyl, but-2-enyl, but-3-enyl, 1-methylprop-1-enyl, 2-methylprop-1-enyl, 1-methylprop-2-enyl, 2-methylprop-2-enyl, pent-1-enyl, pent-2-enyl, pent-3-enyl, pent-4-enyl, 1-methylbut-1-enyl, 2-methylbut-1-enyl, 3-methylbut-1-enyl, 1-methylbut-2-enyl, 2-methylbut-2-enyl, 3-methylbut-2-enyl, 1-methylbut-3-enyl, 2-methylbut-3-enyl, 3-methylbut-3-enyl, 1,1-dimethylprop-2-enyl, 1,2-dimethylprop-1-enyl, 1,2-dimethylprop-2-enyl, 1-ethylprop-1-enyl, 1-ethylprop-2-enyl, hex-1-enyl, hex-2-enyl, hex-3-enyl, hex-4-enyl, hex-5-enyl, 1-methylpent-1-enyl, 2-methylpent-1-enyl, 3-methylpent-1-enyl, 4-methylpent-1-enyl, 1-methylpent-2-enyl, 2-methylpent-2-enyl, 3-methylpent-2-enyl, 4-methylpent-2-enyl, 1-methylpent-3-enyl, 2-methylpent-3-enyl, 3-methylpent-3-enyl, 4-methylpent-3-enyl, 1-methylpent-4-enyl, 2-methylent-4-enyl, 3-methylpent-4-enyl, 4-methylpent-4-enyl, 1,1-dimethylbut-2-enyl, 1,1,-dimethylbut-3-enyl, 1,2-dimethylbut-1-enyl, 1,2-dimethylbut-2-enyl, 1,2-dimethylbut-3-enyl, 1,3-dimethylbut-1-enyl, 1,3-dimethylbut-2-enyl, 1,3-dimethylbut-3-enyl, 2,2-dimethylbut-3-enyl, 2,3-dimethylbut-1-enyl, 2,3-dimethylbut-2-enyl, 2,3-dimethylbut-3-enyl, 3,3-dimethylbut-1-enyl, 3,3-dimethylbut-2-enyl, 1-ethylbut-1-enyl, 1-ethylbut-2-enyl, 1-ethylbut-3-enyl, 2-ethylbut-1-enyl, 2-ethylbut-2-enyl, 2-ethylbut-3-enyl, 1,1,2-trimethylprop-2-enyl, 1-ethyl-1-methylprop-2-enyl, 1-ethyl-2-methylprop-1-enyl and 1-ethyl-2-methylprop-2-enyl.

Cycloalkenyl represents a monocyclic or bicyclic partially unsaturated hydrocarbon radical having 5 to 10 carbon atoms and one to three double bonds. Non-limiting examples include cycloopentenyl, cyclo-hexenyl, cyclohexadienyl, cycloheptenyl, cyclooctenyl, cyclooctadienyl, indanyl and tetrahydro-naphthalenyl.

Alkynyl represents a straight-chain or branched hydrocarbyl groups having 2 to 8, preferably 2 to 6, carbon atoms and one triple bond in any position. Non-limiting examples include ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 1-methylbut-2-ynyl, 1-methylbut-3-ynyl, 2-methylbut-3-ynyl, 3-methylbut-1-ynyl, 1,1-dimethylprop-2-ynyl, 1-ethylprop-2-ynyl, hex-1-ynyl, hex-2-ynyl, hex-3-ynyl, hex-4-ynyl, hex-5-ynyl, 1-methylpent-2-ynyl, 1-methylpent-3-ynyl, 1-methylpent-4-ynyl, 2-methylpent-3-ynyl, 2-methylpent-4-ynyl, 3-methylpent-1-ynyl, 3-methylpent-4-ynyl, 4-methylpent-1-ynyl, 4-methylpent-2-ynyl, 1,1-dimethylbut-2-ynyl, 1,1-dimethylbut-3-ynyl, 1,2-dimethylbut-3-ynyl, 2,2-dimethylbut-3-ynyl, 3,3-dimethylbut-1-ynyl, 1-ethylbut-2-ynyl, 1-ethylbut-3-ynyl, 2-ethylbut-3-ynyl and 1-ethyl-1-methylprop-2-ynyl.

Haloalkenyl represents in general an alkenyl-radical having 2 to 8 carbon atoms, in which 1 up to all hydrogen atoms are replaced by halogen atoms. Non-limiting examples include 3-bromo-2-propenyl, 2-bromo-2-propenyl, 3-chloro-2-propenyl and 2-chloro-2-propenyl.

Haloalkynyl represents in general an alkynyl-radical having 2 to 8 carbon atoms, in which 1 up to all hydrogen atoms are replaced by halogen atoms. Non-limiting examples include 2-iodopropynyl and 2-bromopropynyl.

Alkoxy represents a saturated, straight-chain or branched alkoxy radical having 1 to 8 atoms. Non-limiting examples include methoxy, ethoxy, propoxy, 1-methylethoxy, butoxy, 1-methylpropoxy, 2-methylpropoxy, 1,1-dimethylethoxy.

Haloalkoxy represents a saturated, straight-chain or branched alkoxy radical having 1 to 8 atoms, in which one up to all hydrogen atoms are replaced by halogen atoms. Non-limiting examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloro-ethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

Alkylthio represents a thiol radical with a saturated, straight-chain or branched alkyl residue having 1 to 8 carbon atoms. Non-limiting examples include methylthio, ethylthio, n-propylthio, iso-propylthio, 1-methylethylthio, n-butylthio and tert.-butylthio.

Alkylsulphinyl represents $(C_1-C_8)$-alkyl-S(O)— radical with a saturated, straight-chain or branched alkyl residue having 1 to 8 carbon atoms. Non-limiting examples include methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethyl-butylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl.

Alkylsulplphvl represents a sulphone radical with a saturated, straight-chain or branched alkyl residue having 1 to 8 carbon atoms. Non-limiting examples include methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexyl-sulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethyl-butylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl.

Heterocyclyl represent a monocyclic, saturated or partially unsaturated heterocyclic radical having a total number of 3 to 7, including 2 to 6 carbon atoms and 1 up to 3 heteroatoms and/or hetero-groups independently selected from the group consisting of N, O, S, SO, $SO_2$ and Di-$(C_1-C_4)$-alkylsilyl, which ring system can be bonded via a ring carbon atom or, if possible, via a ring nitrogen atom. Non-limiting examples include oxiranyl, aziridinyl, oxetan-2-yl, oxetan-3-yl, azetidin-2-yl, azetidin-3-yl, tetrahydrofuran-2-yl, tetrahydrofuran-3-yl, tetrahydrothien-2-yl, tetrahydrothien-3-yl, pyrrolidin-2-yl, pyrrolidin-3-yl, thiolan-2-yl, thiolan-3-yl, sulfolan-2yl, sulfolan-3-yl, isoxazolidin-3-yl, isoxazolidin-4-yl, isoxazolidin-5-yl, isothiazolidin-3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidin-2-yl, piperidin-3-yl, piperidin-4-yl, 1,3-dioxan-5-yl, tetrahydropyran-2-yl, tetrahydropyran-3-yl, tetrahydropyran-4-yl, tetrahydrothiopyran-2-yl, tetra-hydrothiopyran-3-yl, tetrahydrothiopyran-4-yl, hexahydropyridazin-3-yl, hexahydropyridazin-4-yl, hexahydropyrimidin-2-yl, hexahydropyrimidin-4-yl, hexahydropyrimidin-5-yl, piperazin-2-yl, morpholin-2-yl, morpholin-3-yl, thiomorpholin-2-yl, thiomorpholin-3-yl, 1,1-dioxidothiomorpholin-2-yl, 1,1-dioxidothiomorpholin-3-yl, 1,3,5-hexahydrotriazin-2-yl and 1,2,4-hexahydrotriazin-3-yl.

Heteroaryl and heteroaryl ring in general represents a mono-cyclic, aromatic heterocyclic radical having a total number of 5 or 6 ring atoms, including 1 to 5 carbon atoms and up to 4 heteroatoms independently selected from the group consisting of N, O and S, which ring system can be bonded via a ring carbon atom or, if possible, via a ring nitrogen atom. Non-limiting examples include furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl, triazinyl. Preferred are furyl, thienyl, pyrazolyl, imidazolyl, thiazolyl, oxazolyl, isoxazolyl, triazolyl, oxadiazolyl, thiadiazolyl, pyridyl and pyrimidinyl.

Oxo represents a doubly bonded oxygen atom.

Preferred are compounds of the formulae (G1) and (G2) and/or salts thereof, wherein A is $CR^6R^7$, x is 0, 1 or 2, $R^1$ is hydrogen, $(C_3-C_6)$-cycloalkyl, $(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, phenyl, pyridinyl, furanyl, thienyl wherein all these residues are unsubstituted or substituted by one or more residues from the group consisting of halogen, nitro, hydroxyl, cyano, $NR^{13}R^{14}$, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, $R^2$, $R^3$ are each independently hydrogen, $(C_1-C_6)$-alkoxyphenyl-$(C_1-C_6)$-alkyl, $(C_1-C_6)$-alkylthiocarbonyl, $(C_1-C_6)$-haloalkylthiocarbonyl, $(C_1-C_6)$-alkoxy-$(C_1-C_6)$-alkylcarbonyl, $(C_1-C_6)$-alkylthio-$(C_1-C_6)$-alkylcarbonyl, $(C_1-C_6)$-alkylsulphinyl-$(C_1-C_6)$-alkylcarbonyl, $(C_1-C_6)$-alkylsulphonyl-$(C_1-C_6)$-alkylcarbonyl, $(C_1-C_6)$-alkylcarbonyl, $(C_1-C_6)$-haloalkylcarbonyl, $(C_2-C_6)$-alkenylcarbonyl, $(C_2-C_6)$-alkynylcarbonyl, $(C_1-C_6)$-alkoxycarbonyl-$(C_1-C_6)$-alkylcarbonyl, $(C_1-C_6)$-alkoxycarbonyl, $(C_1-C_6)$-haloalkoxycarbonyl, $(C_2-C_6)$-alkenyloxycarbonyl, $(C_3-C_6)$-cycloalkylcarbonyl, $(C_3-C_6)$-cycloalkyl-$(C_1-C_6)$-alkylcarbonyl, phenylcarbonyl, phenyl-$(C_1-C_6)$-alkylcarbonyl, pyridinylcarbonyl, furanylcarbonyl, thienylcarbonyl, pyridinyl-$(C_1-C_6)$-alkylcarbonyl, furanyl-$(C_1-C_6)$-alkylcarbonyl, thienyl-$(C_1-C_6)$-alkylcarbonyl, heterocyclylcarbonyl, heterocyclyl-$(C_1-C_6)$-alkylcarbonyl, wherein all these residues are unsubstituted or substituted by one or more residues from the group consisting of halogen, nitro, hydroxyl, cyano, $NR^{13}R^{14}$, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $NR^2R^3$ is $-N=S(O)_nR^{10}R^{11}$, $R^4$, $R^5$ are each independently hydrogen, formyl, oxytetrahydropyranmethyl, cyano, halogen, $(C_1-C_6)$-alkoxycarbonyl, $(C_1-C_6)$-alkoxy-$(C_1-C_6)$-alkyl, $(C_1-C_6)$-alkylcarbonyloxy, $(C_1-C_6)$-alkylcarbonyloxy-$(C_1-C_6)$-alkyl, $(C_1-C_6)$-alkyloxycarbonyloxy-$(C_1-C_6)$-alkyl $(C_1-C_6)$-alkyl, $(C_1-C_6)$-alkylsilyl, $(C_3-C_6)$-cycloalkyl-$(C_1-C_6)$-alkyl, $(C_3-C_6)$-cycloalkyl, $(C_3-C_6)$-cycloalkenyl, $(C_2-C_6)$-alkynylcarbonyl, $(C_3-C_6)$-cycloalkyl-$(C_1-C_6)$-alkylaminocarbonyl, $(C_2-C_6)$-alkenyl, aminocarbonyl, $(C_2-C_6)$-alkynyl, $(C_2-C_6)$-alkenylcarbonyl, imino-$(C_1-C_6)$-alkyl, phenyl, pyridinyl, furanyl, thienyl, wherein all these residues are unsubstituted or substituted by one or more residues from the group consisting of halogen, hydroxyl, $(C_1-C_6)$-alkoxy, $(C_1-C_6)$-alkyl, $(C_1-C_6)$-alkoxycarbonyl, $(C_1-C_6)$-alkoxycarbonyl-$(C_1-C_6)$-alkoxy, $(C_3-C_6)$-cycloalkyl-$(C_1-C_6)$-alkoxyimino, $(C_2-C_6)$-alkenyloxyimino, $(C_1-C_6)$-alkyloxyimino, aminocarbonyl, provided that $R^4$ and $R^5$ are not hydrogen at the same time, $R^6$ is hydrogen, $R^7$ is hydrogen or $(C_1-C_6)$-alkyl, $(C_3-C_6)$-cycloalkyl, $R^{10}$, $R^{11}$ are each independently hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, phenyl, phenyl-$(C_1-C_6)$-alkyl, pyridinyl, furanyl, thienyl, pyridinyl-$(C_1-C_6)$-alkyl, thienyl-$(C_1-C_6)$-alkyl, furanyl-$(C_1-C_6)$-alkyl, heterocyclyl, heterocyclyl-$(C_1-C_6)$-alkyl, wherein all these residues are unsubstituted or substituted by one or more residues from the group consisting of halogen, nitro, hydroxyl, cyano, $NR^{13}R^{14}$, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $R^{10}$ and $R^{11}$, together with the sulphur atom to which they are attached, form a 3- to 6-membered unsaturated, partially saturated or saturated ring, which comprises in each case, in addition to the carbon atoms and in addition to the sulphur atom, p ring members from the group consisting of $N(R^{12})_m$, O and $S(O)_n$, and wherein all these residues are unsubstituted or substituted by one or more residues from the group consisting of halogen, nitro, hydroxyl, cyano, $NR^{13}R^{14}$, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl or $(C_1-C_6)$-alkylsulphonyl, $R^{12}$ is hydrogen, $(C_1-C_6)$-alkyl or $(C_1-C_6)$-alkylcarbonyl, $R^{13}$, $R^{14}$ are each independently hydrogen, $(C_1-C_6)$-alkyl, wherein these residues are unsubstituted or substituted by one or more residues from the group consisting of halogen, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, or $R^{13}$ and $R^{14}$, together with the nitrogen atom to which they are attached, form a 3- to 8-membered unsaturated, partially saturated or saturated ring, n is 0,
m is independently selected from 0 or 1,
p is independently selected from 0 or 1,
q is independently selected from 0 or 1,
y is 0 or 1.

Particularly preferred are compounds of the formulae (G1) and (G2) and/or salts thereof, wherein A is $CR^6R^7$,
x is 0, 1 or 2,
$R^1$ is hydrogen, cyclopropyl, cyclobutyl, cyclopentyl, cyclohexyl or phenyl, wherein all these residues are unsubstituted or substituted by one or more residues from the group consisting of halogen, $R^2$, $R^3$ are each independently hydrogen, $(C_1-C_4)$-alkoxyphenyl-$(C_1-C_4)$-alkyl, $(C_1-C_4)$-alkylcarbonyl, $(C_1-C_4)$-haloalkylcarbonyl, $(C_2-C_5)$-alkenylcarbonyl, $(C_2-C_5)$-alkynylcarbonyl, $(C_1-C_4)$-alkoxycarbonyl, $(C_1-C_4)$-haloalkoxycarbonyl, $(C_1-C_4)$-alkoxy-$(C_1-C_4)$-alkylcarbonyl, $(C_1-C_4)$-haloalkoxy-$(C_1-C_4)$-alkylcarbonyl, $R^4$, $R^5$ are each independently hydrogen, formyl, oxytetrahydropyranmethyl, cyano, halogen, $(C_1-C_4)$-alkoxycarbonyl, $(C_1-C_4)$-alkoxy-$(C_1-C_4)$-alkyl, $(C_1-C_4)$-alkylcarbonyloxy-$(C_1-C_4)$-alkyl, $(C_1-C_4)$-alkylcarbonyloxy, $(C_1-C_6)$-alkyl, $(C_1-C_4)$-alkylsilyl, $(C_3-C_6)$-cycloalkyl-$(C_1-C_4)$-alkyl, $(C_3-C_6)$-cycloalkyl, $(C_3-C_6)$-cycloalkenyl, $(C_2-C_5)$-alkynylcarbonyl, $(C_3-C_6)$-cycloalkyl-$(C_1-C_4)$-alkylaminocarbonyl, $(C_2-C_6)$-alkenyl, aminocarbonyl, $(C_2-C_6)$-alkynyl, $(C_2-C_5)$-alkenylcarbonyl, $(C_1-C_4)$-alkoxycarbonylamino-$(C_1-C_4)$-alkyl, imino-$(C_1-C_4)$-alkyl, phenyl, pyridinyl, furanyl, thienyl, carboxythienyl, phenoxycarbonyl, wherein all these residues are unsubstituted or substituted by one or more residues from the group consisting of halogen, hydroxyl, $(C_1-C_4)$-alkoxy, $(C_1-C_4)$-alkyl, $(C_1-C_4)$-alkoxycarbonyl, $(C_1-C_4)$-alkoxycarbonyl-$(C_1-C_4)$-alkoxy, $(C_3-C_6)$-cycloalkyl-$(C_1-C_4)$-alkoxyimino, $(C_2-C_5)$alkenyloxyimino, $(C_1-C_4)$alkyloxyimino, aminocarbonyl, provided that $R^4$ and $R^5$ are not hydrogen at the same time, $R^6$ is hydrogen,
$R^7$ is hydrogen or methyl,
y is 0 or 1.

Preferred are compounds of the formula (G1), wherein x corresponds to 0. These compounds correspond to the formula (I):

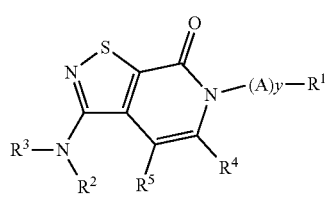

(I)

Compounds of the formula (I), wherein $R^1$, $R^2$, $R^3$, $R^4$, $R^5$, A and y have the meaning as defined in the context of the formula (G1), preferably have the meaning as defined in one of the preferred or particularly preferred embodiments.

Particularly preferred are compounds of the formula (I), wherein at least one of $R^2$ and $R^3$ equals H and one of $R^4$ and $R^5$ equals H.

Preferred are compounds of the formula (G1), wherein x corresponds to 1. These compounds correspond to the formula (II):

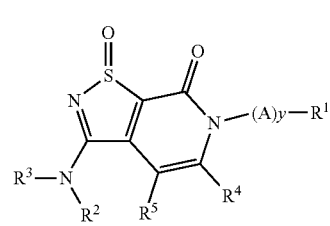

(II)

Compounds of the formula (II) wherein $R^1$, $R^2$, $R^3$, $R^4$, $R^5$, A and y have the meaning as defined in the context of the formula (G1), preferably have the meaning as defined in one of the preferred or particularly preferred embodiments.

Preferred are compounds of the formula (G1), wherein x corresponds to 2. These compounds correspond to the formula (III):

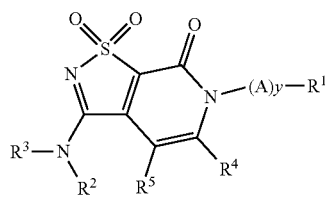

(III)

Compounds of the formula (III) wherein $R^1$, $R^2$, $R^3$, $R^4$, $R^5$, A and y have the meaning as defined in the context of the formula (G1), preferably have the meaning as defined in one of the preferred or particularly preferred embodiments.

Preferred are compounds of the formula (G2), wherein x corresponds to 0. These compounds correspond to the formula (IV):

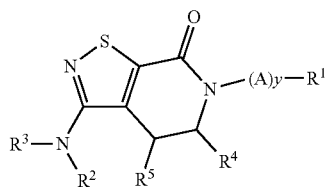

(IV)

Compounds of the formula (IV) wherein $R^1$, $R^2$, $R^3$, $R^4$, $R^5$, A and y have the meaning as defined in the context of the formula (G2), preferably have the meaning as defined in one of the preferred or particularly preferred embodiments.

In the following Tables 1 to 4 specific and preferred definitions of $R^1$bis, $R^2$, $R^3$, $R^4$ and $R^5$, respectively, are mentioned (where $R^1$bis=$(A)_y$-$R^1$).

TABLE 1

Preferred compounds of the formula (I):

| Ex. No. | R2 | R3 | R1bis | R4 | R5 |
|---|---|---|---|---|---|
| I-001 | H | (4-methoxy-phenyl)methyl | H | phenyl | phenyl |
| I-002 | H | (4-methoxy-phenyl)methyl | H | hydroxymethyl | phenyl |
| I-003 | H | (4-methoxy-phenyl)methyl | H | (methoxycarbonyl) | phenyl |
| I-004 | H | (4-methoxy-phenyl)methyl | H | (methoxycarbonyl) | (methoxycarbonyl) |
| I-005 | H | H | H | phenyl | phenyl |
| I-008 | H | H | H | (methoxycarbonyl) | (methoxycarbonyl) |
| I-009 | H | H | H | hydroxymethyl | phenyl |
| I-010 | H | (4-methoxy-phenyl)methyl | H | 2-hydroxyethyl | H |
| I-011 | H | (4-methoxy-phenyl)methyl | H | trimethylsilyl | H |
| I-012 | H | H | H | (methoxycarbonyl) | phenyl |
| I-013 | H | H | H | trimethylsilyl | H |
| I-014 | H | H | H | 2-hydroxyethyl | H |
| I-015 | H | H | H | cyclohexylmethyl | H |
| I-017 | H | H | H | (methoxycarbonyl) | H |
| I-018 | H | H | cyclohexylmethyl | methyl | H |
| I-019 | H | H | H | [[[rac-(1S)-1-cyclohexyl-ethyl]amino]carbonyl] | H |
| I-020 | H | H | cyclohexylmethyl | ethyl | H |
| I-021 | H | 2,2,3,3,3-pentafluor-propanoyl | cyclohexylmethyl | isopropyl | H |
| I-022 | H | 2,2,3,3,3-pentafluor-propanoyl | cyclohexylmethyl | cyclopropyl | H |
| I-023 | H | H | cyclohexylmethyl | isopropyl | H |
| I-024 | H | propionyl | cyclohexylmethyl | isopropyl | H |
| I-025 | H | propionyl | cyclohexylmethyl | cyclopropyl | H |
| I-026 | H | H | cyclohexylmethyl | propyl | H |
| I-027 | H | H | cyclohexylmethyl | acetyloxymethyl | H |
| I-028 | H | H | cyclohexylmethyl | methoxymethyl | H |
| I-029 | H | propionyl | cyclohexylmethyl | ethyl | H |
| I-030 | H | 2,2,3,3,3-pentafluor-propanoyl | cyclohexylmethyl | ethyl | H |
| I-031 | H | propionyl | cyclohexylmethyl | propyl | H |
| I-032 | H | 2,2,3,3,3-pentafluor-propanoyl | cyclohexylmethyl | propyl | H |
| I-033 | H | propionyl | cyclohexylmethyl | methoxymethyl | H |
| I-034 | H | 2,2,3,3,3-pentafluor-propanoyl | cyclohexylmethyl | methoxymethyl | H |
| I-035 | H | 2,2,3,3,3-pentafluor-propanoyl | cyclohexylmethyl | acetyloxymethyl | H |
| I-036 | H | H | cyclohexylmethyl | hydroxymethyl | H |
| I-037 | H | H | cyclohexylmethyl | cyclopropyl | H |
| I-038 | H | H | cyclohexylmethyl | oxytetrahydropy-ranmethyl | H |
| I-040 | H | H | cyclohexylmethyl | formyl | H |
| I-041 | H | H | cyclohexylmethyl | diethoxymethyl | H |
| I-042 | propionyl | propionyl | cyclohexylmethyl | oxytetrahydropy-ranmethyl | H |
| I-043 | H | 2,2,3,3,3-pentafluor-propanoyl | cyclohexylmethyl | oxytetrahydropy-ranmethyl | H |
| I-046 | H | H | cyclohexylmethyl | propionyloxymethyl | H |
| I-047 | H | 2,2,3,3,3-pentafluor-propanoyl | cyclohexylmethyl | hydroxymethyl | H |
| I-048 | H | propionyl | cyclohexylmethyl | hydroxymethyl | H |
| I-049 | propionyl | propionyl | cyclohexylmethyl | hydroxymethyl | H |
| I-050 | H | H | cyclohexylmethyl | 2-methylpropyl | H |
| I-051 | H | H | cyclohexylmethyl | vinyl | H |
| I-052 | H | H | cyclohexylmethyl | (4-fluorphenyl) | H |
| I-053 | (tert-butoxycarbonyl) | (tert-butoxycarbonyl) | cyclohexylmethyl | H | brom |
| I-054 | H | H | cyclohexylmethyl | H | brom |

TABLE 1-continued

Preferred compounds of the formula (I):

| Ex. No. | R2 | R3 | R1bis | R4 | R5 |
|---|---|---|---|---|---|
| I-055 | H | H | cyclohexylmethyl | 2-methoxypropan-2-yl | H |
| I-056 | H | (2,2,2-trifluoracetyl) | cyclohexylmethyl | 2-methylpropyl | H |
| I-057 | H | H | cyclohexylmethyl | (4-chlorphenyl) | H |
| I-058 | (tert-butoxycarbonyl) | (tert-butoxycarbonyl) | cyclohexylmethyl | formyl | H |
| I-059 | H | H | cyclohexylmethyl | (2,4-difluorphenyl) | H |
| I-060 | H | H | cyclohexylmethyl | phenyl | H |
| I-061 | (tert-butoxycarbonyl) | (tert-butoxycarbonyl) | cyclohexylmethyl | oxytetrahydropyranmethyl | H |
| I-062 | H | propionyl | cyclohexylmethyl | vinyl | H |
| I-063 | H | H | cyclohexylmethyl | [(tert-butoxycarbonyl)amino]methyl | H |
| I-064 | H | H | cyclohexylmethyl | H | Cl |
| I-065 | propionyl | propionyl | cyclohexylmethyl | 2-methoxypropan-2-yl | H |
| I-066 | H | propionyl | cyclohexylmethyl | 2-methoxypropan-2-yl | H |
| I-067 | propionyl | propionyl | cyclohexylmethyl | vinyl | H |
| I-068 | (tert-butoxycarbonyl) | (tert-butoxycarbonyl) | cyclohexylmethyl | H | Cl |
| I-069 | H | H | cyclohexylmethyl | H | 2-trimethyl-silylethin-1-yl |
| I-070 | H | H | cyclohexylmethyl | H | ethinyl |
| I-071 | H | H | cyclohexylmethyl | H | (4-fluorphenyl) |
| I-072 | H | H | cyclohexylmethyl | 1-hydroxyethyl | H |
| I-073 | H | H | (2,4,5-trifluorphenyl)methyl | (4-chlorphenyl) | H |
| I-074 | H | H | (2,4,5-trifluorphenyl)methyl | phenyl | H |
| I-075 | H | H | (2,4,5-trifluorphenyl)methyl | (2,4-difluorphenyl) | H |
| I-076 | H | H | (2,4,5-trifluorphenyl)methyl | (4-fluorphenyl) | H |
| I-077 | H | 2,2,3,3,3-pentafluorpropanoyl | cyclohexylmethyl | H | brom |
| I-078 | H | propionyl | cyclohexylmethyl | H | brom |
| I-079 | propionyl | propionyl | cyclohexylmethyl | H | brom |
| I-080 | H | H | cyclohexylmethyl | H | vinyl |
| I-081 | H | 2,2,3,3,3-pentafluorpropanoyl | cyclohexylmethyl | H | Cl |
| I-082 | propionyl | propionyl | cyclohexylmethyl | H | Cl |
| I-083 | H | propionyl | cyclohexylmethyl | H | Cl |
| I-084 | H | acetyl | cyclohexylmethyl | H | Cl |
| I-085 | H | (2-methoxyacetyl) | cyclohexylmethyl | H | Cl |
| I-086 | H | (2,2,2-trifluoracetyl) | cyclohexylmethyl | H | Cl |
| I-087 | H | (2-methoxyacetyl) | cyclohexylmethyl | H | brom |
| I-088 | H | (2,2,2-trifluoracetyl) | cyclohexylmethyl | H | brom |
| I-089 | H | H | cyclohexylmethyl | (aminocarbonyl) | H |
| I-090 | H | H | cyclohexylmethyl | H | 3-methylbut-1-in-1-yl |
| I-091 | H | 2,2,3,3,3-pentafluorpropanoyl | cyclohexylmethyl | H | (4-chlorphenyl) |
| I-092 | propionyl | propionyl | cyclohexylmethyl | H | (4-chlorphenyl) |
| I-093 | H | propionyl | cyclohexylmethyl | H | (4-chlorphenyl) |
| I-094 | H | H | cyclohexylmethyl | H | ethyl |
| I-095 | H | H | cyclohexylmethyl | H | pent-1-in-1-yl |
| I-096 | H | H | cyclohexylmethyl | H | pyridin-3-yl |
| I-097 | propionyl | propionyl | cyclohexylmethyl | H | phenyl |
| I-098 | H | propionyl | cyclohexylmethyl | H | phenyl |
| I-099 | H | H | cyclohexylmethyl | H | phenyl |
| I-100 | H | H | cyclohexylmethyl | H | (4-chlorphenyl) |
| I-101 | H | 2,2,3,3,3-pentafluorpropanoyl | cyclohexylmethyl | H | phenyl |
| I-102 | H | H | cyclohexylmethyl | H | brom |
| I-103 | H | acetyl | cyclohexylmethyl | H | 3-methoxyprop-1-in-1-yl |
| I-104 | H | H | cyclohexylmethyl | H | 2-phenylethin-1-yl |
| I-105 | H | H | cyclohexylmethyl | H | (3-methoxy-3-methylbut-1-in-1-yl) |

TABLE 1-continued

Preferred compounds of the formula (I):

| Ex. No. | R2 | R3 | R1bis | R4 | R5 |
|---|---|---|---|---|---|
| I-106 | H | H | cyclohexylmethyl | H | 4-methylpent-1-in-1-yl |
| I-107 | H | 2,2,3,3,3-pentafluor-propanoyl | cyclohexylmethyl | H | ethyl |
| I-108 | H | H | cyclohexylmethyl | H | [(E)-3-methoxyprop-1-en-1-yl] |
| I-109 | H | H | cyclohexylmethyl | H | [(E)-pent-1-en-1-yl] |
| I-110 | H | H | cyclohexylmethyl | H | pentyl |
| I-111 | H | H | cyclohexylmethyl | H | F |
| I-112 | H | H | cyclohexylmethyl | H | cyclopropyl |
| I-113 | H | H | cyclohexylmethyl | H | [(E)-2-ethoxyethen-1-yl] |
| I-114 | H | H | cyclohexylmethyl | H | prop-1-en-2-yl |
| I-115 | H | H | cyclohexylmethyl | H | prop-1-in-1-yl |
| I-116 | H | propionyl | cyclohexylmethyl | phenyl | H |
| I-117 | H | H | cyclohexylmethyl | H | 4-methylpentyl |
| I-118 | H | H | cyclohexylmethyl | H | [(E)-prop-1-en-1-yl] |
| I-119 | H | H | cyclohexylmethyl | H | cyclohexen-1-yl |
| I-120 | H | H | cyclohexylmethyl | H | [(E)-prop-1-en-1-yl] |
| I-121 | H | H | cyclohexylmethyl | H | 3-cyclopentylprop-1-in-1-yl |
| I-122 | H | H | cyclohexylmethyl | H | 3-cyclohexylprop-1-in-l-yl |
| I-123 | H | H | cyclohexylmethyl | H | 3-phenylprop-1-in-1-yl |
| I-124 | H | H | cyclohexylmethyl | H | 3-thienyl |
| I-125 | H | H | cyclohexylmethyl | H | furan-2-yl |
| I-126 | H | H | cyclohexylmethyl | H | propyl |
| I-127 | H | 2,2,3,3,3-pentafluor-propanoyl | cyclohexylmethyl | H | F |
| I-128 | H | propionyl | cyclohexylmethyl | H | F |
| I-129 | H | H | cyclohexylmethyl | H | furan-3-yl |
| I-130 | H | H | cyclohexylmethyl | H | acetyl |
| I-131 | H | H | cyclohexylmethyl | H | thiophen-2-yl |
| I-132 | H | H | cyclohexylmethyl | H | (5-methyl-2-furyl) |
| I-133 | H | H | cyclohexylmethyl | H | 1-ethoxyethen-1-yl |
| I-134 | H | H | cyclohexylmethyl | H | [(1Z)-1-(methoxyimino)ethyl] |
| I-135 | H | H | cyclohexylmethyl | H | cyano |
| I-136 | H | H | (2,4,5-trifluor-phenyl)methyl | H | Cl |
| I-137 | (tert-butoxycarbonyl) | (tert-butoxycarbonyl) | [rac-(1S,2R)-2-chlorcyclo-hexyl]methyl | H | H |
| I-141 | H | H | cyclohexylmethyl | H | [(1Z)-1-(ethoxyimino)ethyl] |
| I-142 | H | H | cyclohexylmethyl | H | [(1Z)-1-(ethoxyimino)ethyl] |
| I-143 | H | H | cyclohexylmethyl | H | allyl |
| I-145 | H | H | cyclohexylmethyl | H | [rac-(1S)-1-fluorethyl] |
| I-146 | H | H | cyclohexylmethyl | H | [5-(methoxycarbonyl)-3-thienyl] |
| I-147 | H | H | cyclohexylmethyl | H | 1-hydroxyethyl |
| I-148 | H | H | cyclohexylmethyl | H | (5-carboxy-3-thienyl) |
| I-149 | H | acetyl | cyclohexylmethyl | H | acetyl |
| I-150 | H | H | cyclohexylmethyl | H | [5-(aminocarbonyl)-3-thienyl] |
| I-151 | H | H | cyclohexylmethyl | H | (phenoxycarbonyl) |
| I-152 | (tert-butoxycarbonyl) | (tert-butoxycarbonyl) | [rac-(1S,2R)-2-chlorcyclo-hexyl]methyl | H | Cl |
| I-153 | (tert-butoxycarbonyl) | (tert-butoxycarbonyl) | [rac-(1S,2R)-2-chlorcyclohexyl]methyl | H | Cl |
| I-154 | (tert-butoxycarbonyl) | (tert-butoxycarbonyl) | [rac-(1S,2R)-2-chlorcyclo-hexyl]methyl | H | Cl |
| I-155 | H | H | [rac-(1S,2R)-2-chlorcyclo-hexyl]methyl | H | Cl |

TABLE 1-continued

Preferred compounds of the formula (I):

| Ex. No. | R2 | R3 | R1bis | R4 | R5 |
|---|---|---|---|---|---|
| I-156 | H | H | [rac-(1S,2R)-2-chlorcyclo-hexyl]methyl | H | Cl |
| I-159 | H | (2,2-difluoracetyl) | [rac-(1S,2R)-2-chlorcyclo-hexyl]methyl | H | Cl |
| I-160 | H | (2,2-difluoracetyl) | [rac-(1S,2R)-2-chlorcyclo-hexyl]methyl | H | Cl |
| I-161 | H | 2,2,3,3,3-pentafluor-propanoyl | [rac-(1S,2R)-2-chlorcyclo-hexyl]methyl | H | Cl |
| I-162 | H | 2,2,3,3,3-pentafluor-propanoyl | [rac-(1S,2R)-2-chlorcyclo-hexyl]methyl | H | Cl |
| I-163 | H | H | (2,4,5-trifluor-phenyl)methyl | H | F |
| I-164 | (tert-butoxycarbonyl) | (tert-butoxycarbonyl) | (2,4,5-trifluor-phenyl)methyl | H | F |
| I-165 | H | (2,2-difluoracetyl) | (2,4,5-trifluor-phenyl)methyl | H | F |
| I-166 | H | H | cyclohexylmethyl | H | [(1Z)-1-[(2-methoxy-2-oxoethoxy)imino]ethyl] |
| I-167 | H | H | cyclohexylmethyl | H | [(1Z)-1-(cyclopropylmethoxy-imino)ethyl] |
| I-168 | H | H | cyclohexylmethyl | H | [(1Z)-1-(allyloxyimino)ethyl] |
| I-169 | H | H | cyclohexylmethyl | H | [(1Z)-1-(isopropyloxy-imino)ethyl] |
| I-170 | H | H | cyclohexylmethyl | H | carboxy |
| I-171 | H | (2,2,2-trifluoracetyl) | [rac-(1S,2R)-2-chlorcyclo-hexyl]methyl | H | Cl |
| I-172 | H | propionyl | [rac-(1S,2R)-2-chlorcyclo-hexyl]methyl | H | Cl |
| I-173 | H | propionyl | [rac-(1S,2R)-2-chlorcyclo-hexyl]methyl | H | Cl |
| I-174 | H | (2,2,2-trifluoracetyl) | (2,4,5-trifluor-phenyl)methyl | H | F |
| I-175 | H | propionyl | (2, 4, 5-trifluor-phenyl)methyl | H | F |
| I-176 | propionyl | propionyl | (2,4,5-trifluor-phenyl)methyl | H | F |
| I-177 | H | (2,2,2-trifluoracetyl) | [rac-(1S,2R)-2-chlorcyclo-hexyl]methyl | H | Cl |
| I-178 | H | H | [rac-(1S,2R)-2-chlorcyclo-hexyl]methyl | H | F |
| I-179 | H | H | cyclohexylmethyl | H | [(E)-4-methoxy-4-oxobut-2-en-2-yl] |
| I-180 | H | 2,2,3,3,3-pentafluor-propanoyl | (2,4,5-trifluor-phenyl)methyl | H | F |
| I-181 | H | H | [rac-(1S,2R)-2-chlorcyclo-hexyl]methyl | H | F |
| I-182 | H | H | [rac-(1S,2R)-2-chlorcyclo-hexyl]methyl | H | F |
| I-183 | H | 2,2,3,3,3-pentafluor-propanoyl | [rac-(1S,2R)-2-chlorcyclo-hexyl]methyl | H | F |
| I-184 | propionyl | propionyl | cyclohexylmethyl | H | F |

Specific preferred compounds of the formula (II) are shown in Table 2.

TABLE 2

Preferred compounds of the formula (II):

| Ex. No. | R2 | R3 | R1bis | R4 | R5 |
|---|---|---|---|---|---|
| I-157 | H | H | cyclohexylmethyl | H | acetyl |

Specific preferred compounds of formula (III) are shown in Table 3.

TABLE 3

Preferred compounds of formula (III):

| Ex. No. | R2 | R3 | R1bis | R4 | R5 |
|---|---|---|---|---|---|
| I-139 | H | H | cyclohexylmethyl | H | 3-thienyl |
| I-140 | H | H | cyclohexylmethyl | H | thiophen-2-yl |
| I-158 | H | H | cyclohexylmethyl | H | acetyl |

Specific preferred compounds of formula (IV) are shown in Table 4.

TABLE 4

Preferred compounds of formula (IV):

| Ex. No. | R2 | R3 | R1bis | R4 | R5 |
|---|---|---|---|---|---|
| 1-006 | (tert-butoxycarbonyl) | H | cyclohexylmethyl | (tert-butoxycarbonyl)oxymethyl | H |
| 1-007 | H | H | cyclohexylmethyl | hydroxymethyl | H |
| 1-016 | (tert-butoxycarbonyl) | H | H | (tert-butoxycarbonyl)oxymethyl | H |
| 1-039 | H | H | cyclohexylmethyl | propionyloxymethyl | H |
| 1-044 | propionyl | H | cyclohexylmethyl | hydroxymethyl | H |
| 1-045 | propionyl | H | cyclohexylmethyl | propionyloxymethyl | H |
| 1-138 | H | H | cyclohexylmethyl | H | (tert-butoxycarbonyl)oxy |
| 1-144 | H | H | cyclohexylmethyl | H | hydroxy |

Preferably, one or more compounds of the formulae (G1), (G2), (I), (II), (III) and (IV) each as defined above, and the salts thereof, are used in the context of the present invention as herbicides and/or plant growth regulators, preferably in crops of useful plants and/or ornamental plants, wherein the structural elements in the formulae (G1), (G2), (I), (II), (III) and (IV) each have, independently from one another, the meaning as defined in the context of the meaning as defined in one of the preferred or particularly preferred embodiments.

Furthermore one or more compounds of the formulae (G1), (G2), (I), (II), (III) and (IV) each as defined above, and the salts thereof, can be used as fungicides or insecticides.

The present invention also provides processes for preparing the compounds of the general formulae (G1), (G2) and/or their salts. This includes processes which can be carried out analogously to known methods.

Compounds according to the invention may be obtained using different synthetic routes shown in the following Schemes 1 to 8.

Scheme 1: Overview of the synthesis for (G1)

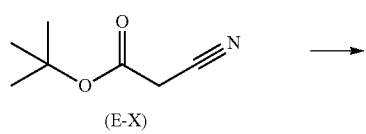

(E-X)

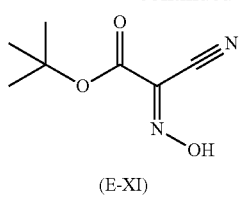

(E-XI)

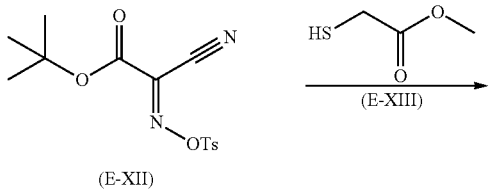

(E-XII)     (E-XIII)

-continued

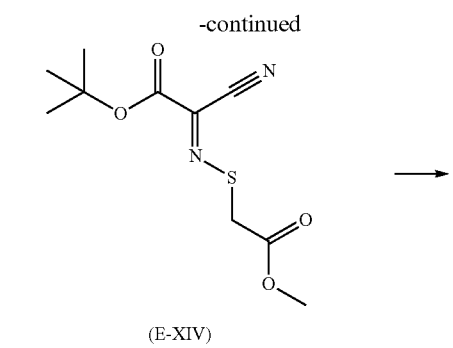

(E-XIV)

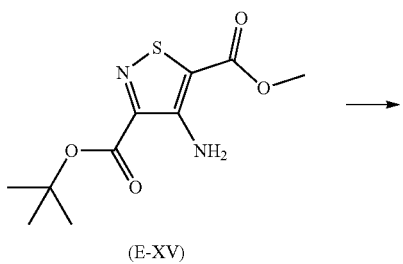

(E-XV)

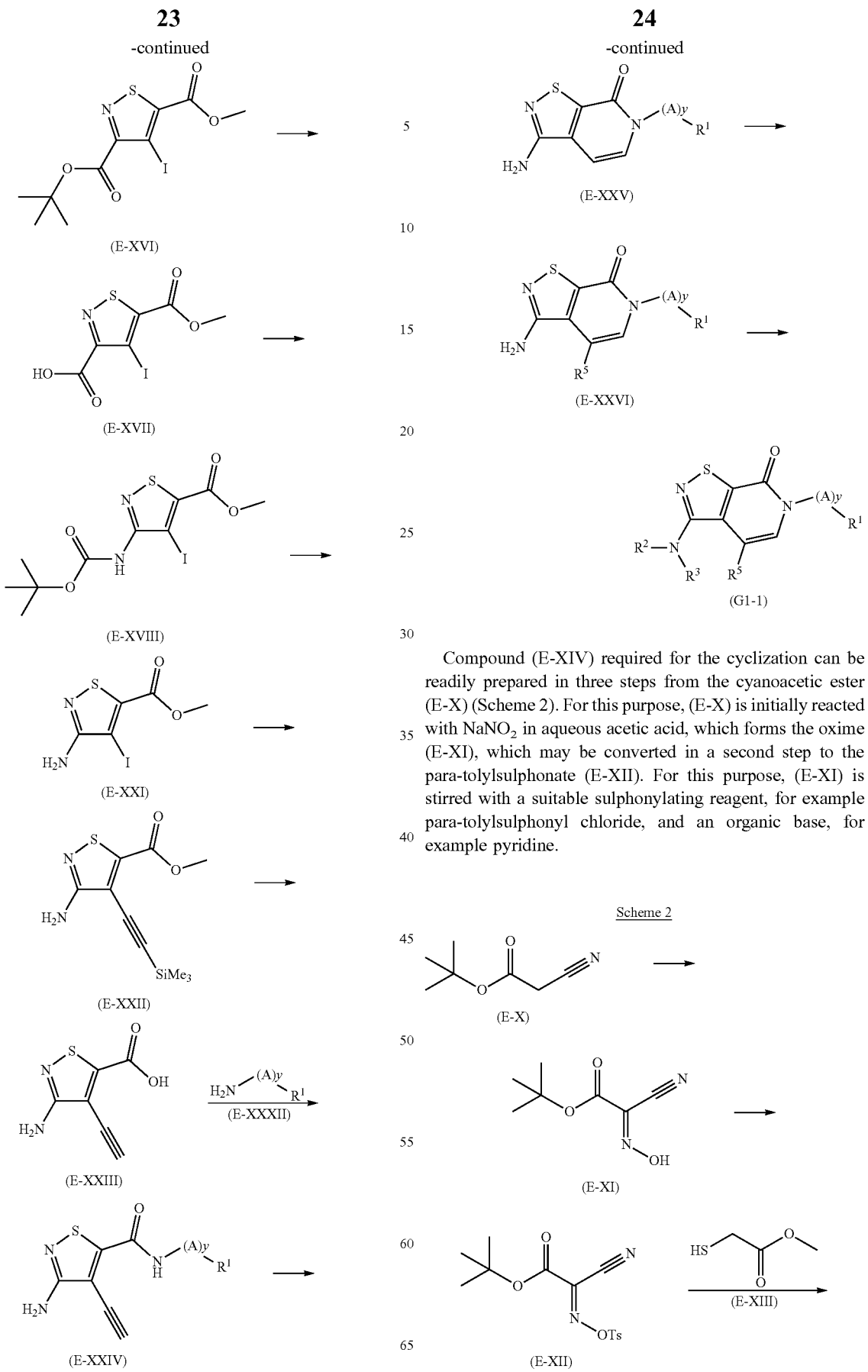

Compound (E-XIV) required for the cyclization can be readily prepared in three steps from the cyanoacetic ester (E-X) (Scheme 2). For this purpose, (E-X) is initially reacted with NaNO₂ in aqueous acetic acid, which forms the oxime (E-XI), which may be converted in a second step to the para-tolylsulphonate (E-XII). For this purpose, (E-XI) is stirred with a suitable sulphonylating reagent, for example para-tolylsulphonyl chloride, and an organic base, for example pyridine.

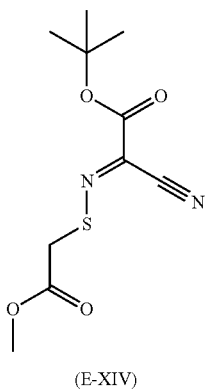

(E-XIV)

The resulting tosylate (E-XII) is reacted in the third step with the thioglycolate (E-XIII), forming a N—S bond, to give the cyclization precursor (E-XIV). This reaction generally takes place in a commonly used organic solvent such as ethanol, with the aid of an organic base such as pyridine (Scheme 2).

The amino compound (E-XV) may be synthesized from the compound (E-XIV) via cyclization, by firstly treating the latter with a weak base, for example triethylamine or other organic bases, and directly after with ethanolic HCl (Scheme 3).

The ester (E-XVI) may be obtained from the amino compound (E-XV) by the Sandmeyer reaction or related reactions. For instance, (E-XV) may be reacted, for example, with an alkyl nitrite, such as isoamyl nitrite, and iodine in an inert solvent, such as acetonitrile, at temperatures between 20° C. and 150° C.

The acid (E-XVII) may be obtained, for example, from the tertiary butyl ester (E-XVI) by the action of acid, such as, for example, trifluoroacetic acid (TFA) or dilute mineral acid in the presence of triethylsilane (Scheme 3).

Scheme 3

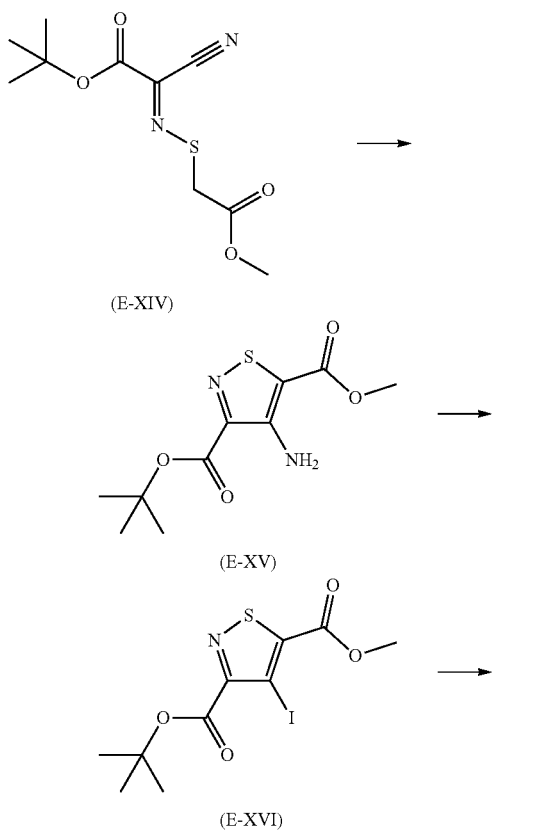

Scheme 4

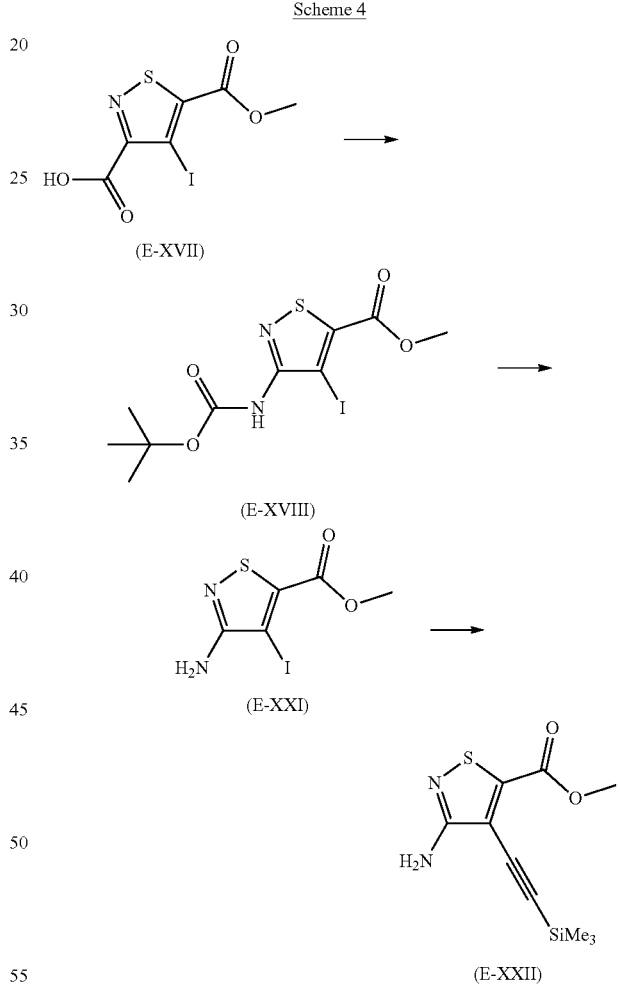

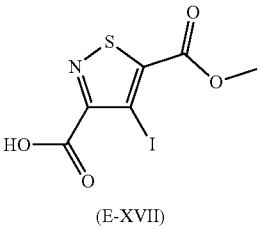

(E-XVII)

The compound (E-XVIII) can be obtained, for example, from the acid (E-XVII) by Hoffman degradation, Curtius or Schmidt rearrangement or by a related reaction, wherein the tertiary butyl carbamate, which is readily isolatable, is directly obtained using a suitable reaction procedure (t-BuOH as solvent or solvent constituent), preferably in the presence of t-BuOH, T3P (propylphosphonic anhydride), trimethylsilyl azide and NEt$_3$ in a solvent like THF (tetrahydrofuran) at elevated temperatures (typically 70° C.) (Scheme 4).

This tertiary butyl carbamate (E-XVIII) may be cleaved to the free amine (E-XXI) by treatment with acid, such as, for example, trifluoroacetic acid or dilute mineral acid.

The ester (E-XXII) can be obtained from compound (E-XXI) by reaction of ethynyltrimethylsilane in the presence of palladium (II) diphenylphosphine dichloride $Pd(PPh_2)_2Cl_2$, CuI and $NEt_3$ in a suitable solvent (e.g. DMF) at elevated temperatures (e.g. 100° C.) (Scheme 4).

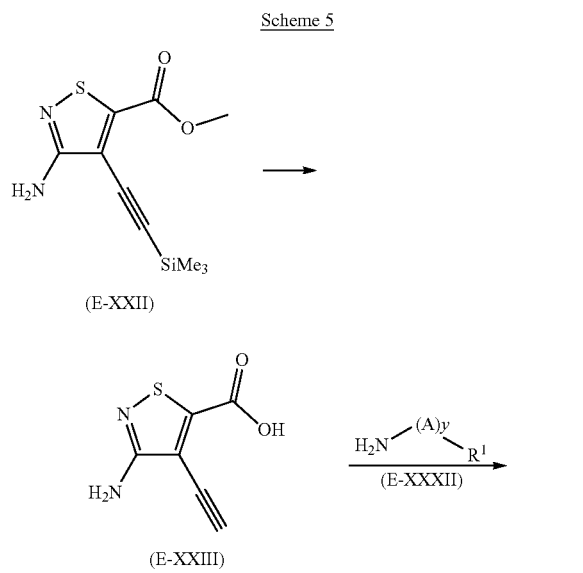

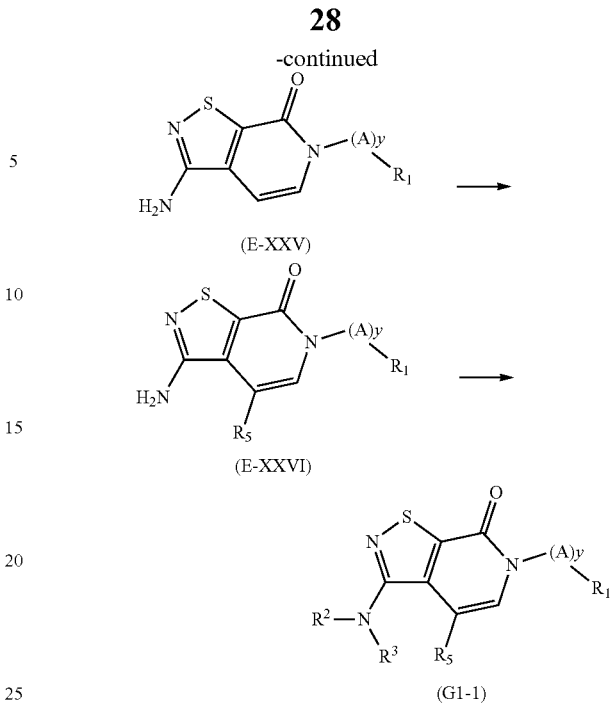

The acid (E-XXIII) in turn is available from the corresponding ester (E-XXII) by basic ester cleavage, for example, with the aid of inorganic bases such as NaOH or LiOH or other bases in aqueous solvents or solvent mixtures like MeOH and THF (tetrahydrofuran).

Intermediate (E-XXIV) may be obtained from the corresponding acid (E-XXIII) by the common amidation reactions with suitable amines (E-XXXII), preferably in the presence of T3P (propylphosphonic anhydride) and $NEt_3$ in a solvent like THF.

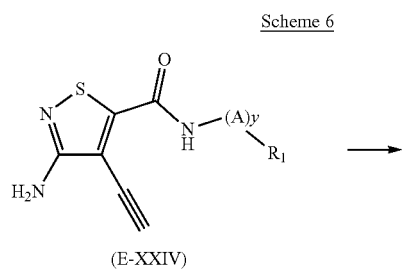

The ring closure of compound (E-XXIV) is effected in the presence of TBAF (tetra-n-butylammonium fluoride) (see e.g. Tetrahedron 2001, 51, 9697-9710) in a suitable solvent, e.g. THF, yielding the isothiazolopyridones (E-XXV) having a free amine group (i.e. $R^2=R^3=H$) (Scheme 6). Compound of formula (E-XXV) may be converted to compound of formula (E-XXVI). Introducing halogens ($R^5=Br$, Cl, F) can be achieved using standard halogenating reagents such as NBS (N-bromosuccinimide), NCS (N-chlorosuccinimide) and Selectfluor® in solvents such as THF, DMF (N,N-dimethylformamide) or DMA (N,N-dimethylacetamide) with temperatures ranging from room temperature (rt) up to 100° C. Sometimes, the free amine (i.e. $R^2=R^3=H$) has to be protected with a Boc (tertbutoxycarbonyl) group (i.e. $R^2=R^3=Boc$) prior to performing the halogenation. Afterwards, the Boc groups can be removed using TFA (trifluoroacetic acid) in dichloromethane (DCM) at rt yielding the compound of formula (E-XXVI) where $R^5$ equals Br, Cl, F. Starting from $R^5$ equals Br, several known and well-described palladium-based reactions can be performed (Sonogashira, Suzuki, Stille etc.) to further functionalize this position. In the final step, the substituents on the amine—$R^2$ and/or $R^3$—are installed using suitable known reactions for converting free amine groups to correspondingly substituted amine groups. For example, suitable conversions are achieved with the corresponding acyl halide(s), acid anhydride(s) or the like, preferably acyl chlorides $R^2COCl$ and/or $R^3COCl$, or anyhdrides $(R^2CO)_2O$, $(R^3CO)_2O$ and/or $R^2CO(O)OCR^3$ using an amine like $NEt_3$, preferably in the presence of DMAP (4-dimethylaminopyridine) in a suitable solvent like DCM at rt and yielding (G1-1).

The compounds (E-X), (E-XI), (E-XII), (E-XIII), (E-XIV), (E-XV), (E-XVI), (E-XVII), (E-XVIII), (E-XXI) and (E-XXXII) are known and have been described in the prior art. Also, the synthetic routes for obtaining (E-XXI) have been described in WO 2016/102435 and WO 2016/102420.

Scheme 7

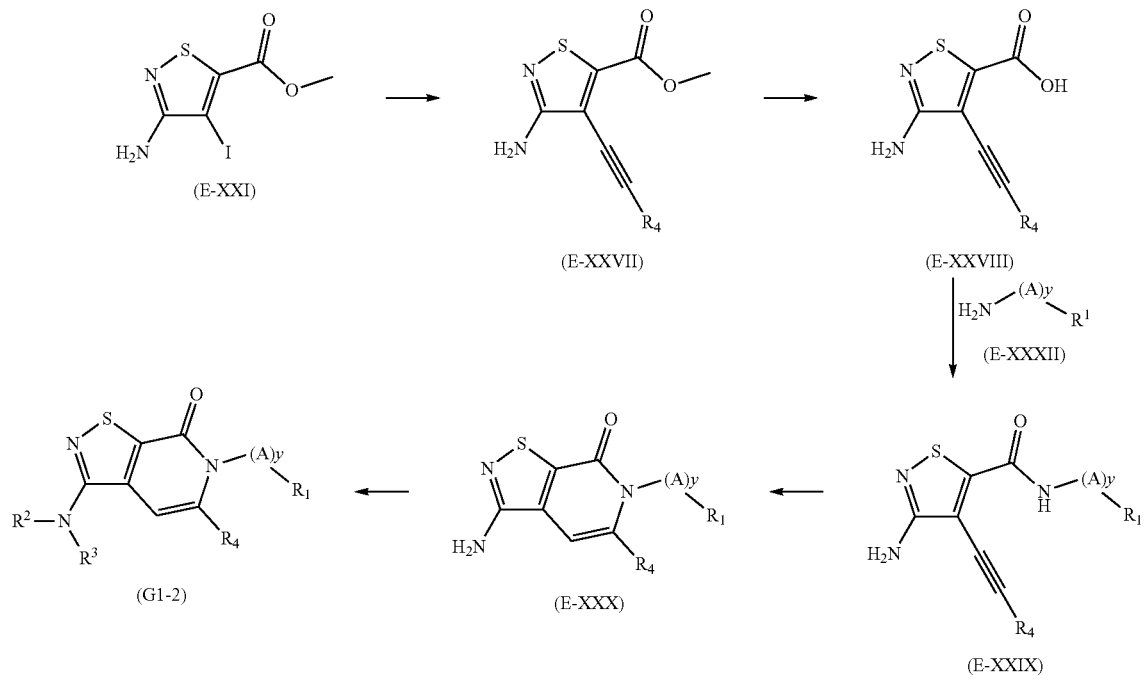

Compounds of the formula (G1-2) are prepared the same way as (G1-1) until reaching intermediate (E-XXI). (E-XXI) is alkynylated using a Sonogashira coupling with Pd(PPh$_3$)$_2$Cl$_2$ in the presence of a base such as Et$_3$N with or without DMF with temperatures ranging from 40° C. up to 100° C. After methyl ester cleavage under basic conditions and amide coupling reaction (both steps are analogous to the one described previously in Scheme 5), the desired intermediate of formula (E-XXIX) was formed. Finally, the cyclization step (the temperature might be raised to 50° C. occasionally) and introduction of R$^2$ and R$^3$ is analogously to the formation of (G1-1) yielding compound of the formula (G-1-2).

Scheme 8

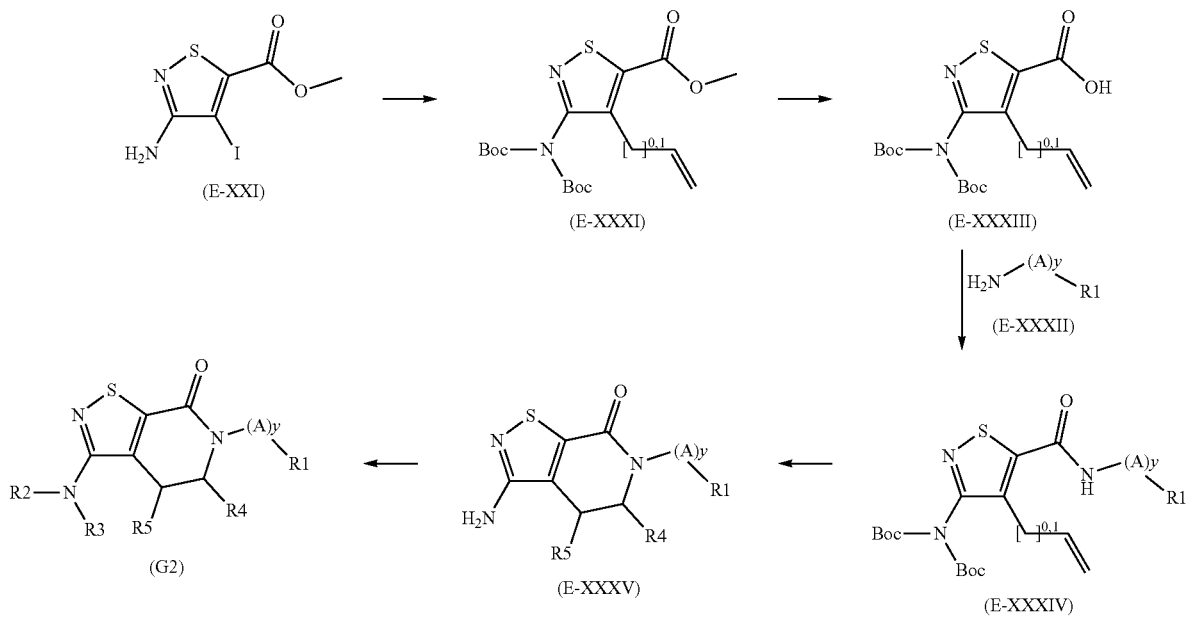

Compounds of the formula (G2) are formed starting from compounds of the formula (E-XXI). Using an olefination reaction, a vinyl moiety can be directly introduced using potassium vinyltrifluoroborate in the presence of $Et_3N$, $PdCl_2$ and EtOH at 100° C. followed by carbamate formation ($R^2=R^3$=Boc) yielding compound of the formula (E-XXXI). An allyl group can also be introduced starting from (E-XXI). The amino group needs first to be protected as a carbamate ($R^2=R^3$=Boc) and an halogen magnesium exchange can then occur in the presence of isopropylmagnesium chloride lithium chloride at −70° C. in THF. Addition of CuCN*2LiCl (Chem. Eur J. 2009, 15, 1468) and warming to −30° C. followed by quenching with allyl bromide. Like previously described, ester cleavage under basic conditions yielded compound of formula (E-XXXIII) and subsequent amide coupling with amine (E-XXXII) formed (E-XXXIV). The desired cyclization can then be performed from the corresponding vinyl or allyl intermediates by means of an epoxide formation using m-CPBA (metachloroperbenzoic acic) in DCM at rt and subsequent treatment with a base such as sodium hydride in THF with temperature ranging between 0° C. and rt. Carbamate deprotection in the presence of trifluoroacetic acid in DCM at rt yielded compound of the formula (E-XXXV) (with $R^4$=H, $R^5$=OH from the vinyl starting material and $R^5$=H and $R^4$=$CH_2OH$ from the allyl starting material). The alcohol can then be converted to other substituents. Introduction of substituents $R^2$ and $R^3$ to form (G2) are analogous to those described above.

Depending on the type of reaction and the reaction conditions used, the skilled person will select suitable organic solvents, such as:

aliphatic hydrocarbons such as pentane, hexane, cyclohexane or petroleum ether;

aromatic hydrocarbons such as toluene, o-, m- or p-xylene, halogenated hydrocarbons such as methylene chloride, chloroform or chlorobenzene, ethers, such as diethyl ether, diisopropyl ether, tert-butyl methyl ether, dioxane, anisole and tetrahydrofuran (THF), nitriles such as acetonitrile or propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulphoxide, dimethylformamide, dimethylacetamide, sulpholane, mixtures of the organic solvents mentioned.

If the compounds described in the context of the present invention, in particular the intermediates and compounds of the formulae (G1) and (G2) of the present invention, are obtained as solids, the purification can also be carried out by recrystallization or digestion.

The following acids are generally suitable for preparing the acid addition salts of the compounds of the formulae (G1) and (G2): hydrohalic acids, such as hydrochloric acid or hydrobromic acid, furthermore phosphoric acid, nitric acid, sulphuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulphonic acids, such as p-toluenesulphonic acid and 1,5-naphthalenedisulphonic acid. The acid addition compounds of the formulae (G1) and (G2) can be obtained in a simple manner by the customary methods for forming salts, for example by dissolving a compound of the formulae (G1) and (G2) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formulae (G1) and (G2) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide.

What is meant by the "inert solvents" referred to in the above process variants are in each case solvents which are inert under the respective reaction conditions.

Collections of compounds of the formulae (G1) and (G2) which can be synthesized by the aforementioned process can also be prepared in a parallel manner, it being possible for this to take place in a manual, partly automated or completely automated manner. In this connection, it is possible to automate the reaction procedure, the work-up or the purification of the products and/or intermediates. Overall, this is understood as meaning a procedure as described, for example, by S. H. DeWitt in "Annual Reports in Combinatorial Chemistry and Molecular Diversity: Automated Synthesis", Volume 1, Verlag Escom, 1997, pages 69 to 77.

For the parallelized reaction procedure and workup it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleiheim, Germany. For the parallel purification of compounds (G1) and (G2) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described here, the preparation of compounds of the formulae (G1) and (G2) can take place completely or partially by solid-phase supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example Barry A. Bunin in "The Combinatorial Index", Academic Press, 1998.

The use of solid-phase-supported synthesis methods permits a number of protocols, which are known from the literature and which for their part may be performed manually or in an automated manner, to be carried out. For example, the "teabag method" (Houghten, U.S. Pat. No. 4,631,211; Houghten et al., Proc. Natl. Acad. Sci, 1985, 82, 5131-5135) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The compounds of the formulae (G1) and (G2) used in the context of the present invention or according to the invention (and/or their salts) have excellent herbicidal efficacy against a broad spectrum of economically important monocotyledonous and dicotyledonous annual harmful plants. The active compounds of the formulae (G1) and (G2) also provide good control over perennial harmful plants which are difficult to control and produce shoots from rhizomes, root stocks or other perennial organs.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds), to the soil in or on which the plants grow (for example the soil of cropland or non-cropland) or to the area on which the plants grow (for example the area under cultivation).

Thus, in a further aspect, the present invention relates to a method for controlling harmful plants or for regulating the growth of plants, characterized in that an effective amount of
    one or more compounds of the formulae (G1) or (G2) and/or salts thereof as defined hereinabove, preferably in one of the preferred, more preferred or particularly preferred embodiments,
    or
    a herbicidal and/or plant growth-regulating composition as defined hereinafter comprising one or more compounds of the formulae (G1) or (G2) and/or salts thereof as defined hereinabove, preferably in one of the preferred, more preferred or particularly preferred embodiments,
is applied to the plants, seeds of plants, the soil in which or on which the plants grow or the area under cultivation.

The compounds according to the invention can be deployed, for example, prior to sowing (if appropriate also by incorporation into the soil), prior to emergence or after emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The compounds of the formulae (G1) and (G2) to be used according to the invention or the compounds of the formulae (G1) and (G2) according to the invention and/or their salts were found to be highly effective in the control of harmful plants such as *Alopecurus myosuroides, Avena fatua, Echinochloa crus-galli, Lolium multiflorum, Setaria viridis, Abutilon theophrasti, Amaranthus retroflexus, Matricaria inodora* (=*Tripleurospermum maritimum* subsp. *inodorum*), *Pharbitis purpurea, Polygonum convolvulus* (=*Fallopia convolvulus*), *Stellaria media, Viola tricolor*, and *Veronica persica.*

When the compounds of the formulae (G1) and (G2) according to the invention are applied to the soil surface before germination, either the weed seedlings are prevented completely from emerging or the weeds grow until they have reached the cotyledon stage, but then stop growing and eventually, after three to four weeks have elapsed, die completely.

If the compounds of the formulae (G1) and (G2) are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamentals.

Furthermore, it has been found that the compounds of the formulae (G1) and (G2) to be used according to the invention or the compounds of the formulae (G1) and (G2) according to the invention and/or their salts show excellent or very good pre-emergence and post-emergence action, and are particularly selectively in certain crops, in particular in oilseed rape, soya beans, cotton and cereals (and here in particular in maize, barley, wheat, rye, oats, triticale, millet varieties, rice).

In addition, the compounds according to the invention (depending on their particular structure and their application rate) have outstanding growth-regulating properties in crop plants. They intervene to regulate the plant's metabolism and can thus be used for controlled influence on plant constituents and to facilitate harvesting, for example by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and/or plant growth-regulating properties, the active compounds of the formulae (G1) and (G2) can also be used for control of harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred with a view to transgenic crops to use the compounds according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and/or plant-growth-regulatory properties, the active compounds of the formulae (G1) or (G2) can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radication.

It is preferred to use the compounds of the formulae (G1) or (G2) according to the invention and/or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to employ the compounds of the formulae (G1) or (G2) according to the invention as herbicides in crops of useful plants which are resistant, or have been made resistant by recombinant means, to the phytotoxic effects of the herbicides.

On employment of the active compounds of the formulae (G1) and (G2) according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formulae (G1) or (G2) according to the invention and/or their salts as herbicides for controlling harmful plants in crops of useful plants or ornamentals, optionally in transgenic crop plants.

Preference is given to the use by the pre- or post-emergence method in cereals such as wheat, barley, rye, oats, millet and rice, in particular in wheat by the post-emergence method.

Preference is also given to the use by the pre- or post-emergence method in corn, in particular by the pre-emergence method in corn.

Preference is also given to the use by the pre- or post-emergence method in soybeans, in particular by the post-emergence method in soybeans.

The use according to the invention for the control of harmful plants or for the growth regulation of plants also includes the case in which the active compound of the formulae (G1) or (G2) or its salt is not formed from a precursor substance ("prodrug") until after application on the plant, in the plant or in the soil.

The invention also provides the method (application method) for controlling harmful plants or for regulating the growth of plants which comprises applying an effective amount of one or more compounds of the formulae (G1) or (G2) and/or salts thereof onto the plants (harmful plants, if appropriate together with the useful plants), plant seeds, the soil in which or on which the plants grow or the area under cultivation.

The compounds of the formulae (G1) and (G2) according to the invention can be used in the form of wettable powders, emulsifiable concentrates, sprayable solutions, dusting products or granules in the customary formulations. The invention therefore also provides herbicidal and/or plant growth-regulating compositions which comprise compounds of the formulae (G1) or (G2) and/or salts thereof.

Thus, in a further aspect, the present invention relates to a herbicidal and/or plant growth-regulating composition, characterized in that said composition comprises one or more compounds of the formulae (G1) and (G2) and/or salts thereof as defined hereinabove, preferably in one of the preferred, more preferred or particularly preferred embodiments, and one or more further substances selected from groups (i) and/or (ii):

(i) one or more further agrochemically active substances, preferably selected from the group consisting of insecticides, acaricides, nematicides, further herbicides, fungicides, safeners, fertilizers and/or further growth regulators, (ii) one or more formulation auxiliaries customary in crop protection.

The compounds of the formulae (G1) and (G2) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and further additives are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schinfeldt, "Grenzflichenaktive Athylenoxidaddukte" [Interface-active Ethylene Oxide Adducts], Wiss. Verlagsgesell., Stuttgart 1976; Winnacker-Kiichler, "Chemische Technologie", volume 7, C. Hanser Verlag Munich, 4th ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are produced by dissolving the active compound in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). The emulsifiers used may, for example, be: alkylarylsulphonic calcium salts, such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting products are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be produced either by spraying the active compound onto adsorptive granulated inert material or by applying active compound concentrates by means of adhesives, for example polyvinyl alcohol, sodium polyacrylate or mineral oils, to the surface of carrier substances, such as sand, kaolinites or of granulated inert material. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formulae (G1) or (G2) and/or salts thereof.

In wettable powders, the active compound concentration is, for example, about 10 to 90% by weight; the remainder to 100% by weight consists of the customary formulation constituents. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formulae (G1) and (G2) and/or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds of the formulae (G1) and (G2) or mixtures thereof, the safeners can be formulated with further herbicides/pesticides and be provided and employed as a finished formulation or tankmix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The application rate of the compounds of the formulae (G1) or (G2) and/or salts thereof can vary within wide limits. For the application as herbicide for controlling harmful plants, for example, generally the range of from 0.001 to 10.0 kg/ha of active substance is suitable, preferably the compounds of the formulae (G1) or (G2) and/or salts thereof are applied in the range of from 0.005 to 5 kg/ha, in particular in the range of from 0.01 to 1 kg/ha. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate of the compounds of the formulae (G1) or (G2) and/or salts thereof is, for example, in the range of from 0.001 to 2 kg/ha or more of active substance, preferably in the range of from 0.005 to 1 kg/ha, in particular in the range of from 10 to 500 g/ha of active substance. This applies both to application by the pre-emergence method and the post-emergence method, the post-emergence treatment generally being preferred.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

Components which can be used in combination with the active compounds according to the invention in mixed formulations or in tank mix are, for example, known active compounds as they are described in, for example, Weed Research 26, 441-445 (1986), or "The Pesticide Manual", 16th edition, The British Crop Protection Council and the Royal Soc. of Chemistry, 2006, and the literature cited therein, and which for example act as inhibitor of acetolactate synthase, acetyl-CoA-carboxylase, cellulose-synthase, enolpyruvylshikimat-3-phosphat-synthase, glutamin-synthetase, p-hydroxyphenylpyruvat-dioxygenase, phytoendesaturase, photosystem I, photosystem II, and/or protoporphyrinogen-oxidase.

Examples of active compounds which may be mentioned as herbicides or plant growth regulators which are known from the literature and which can be combined with the compounds according to the invention are the following (compounds are either described by "common name" in accordance with the International Organization for Standardization (ISO) or by chemical name or by a customary code number), and always comprise all applicable forms such as acids, salts, ester, or modifications such as isomers, like stereoisomers and optical isomers. As an example at least one applicable form and/or modifications can be mentioned.

Examples for herbicides are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, etha-metsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxa-prop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flu-propanate, flupyrsulfuron, flupyrsulfuronmethyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethy,1 and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

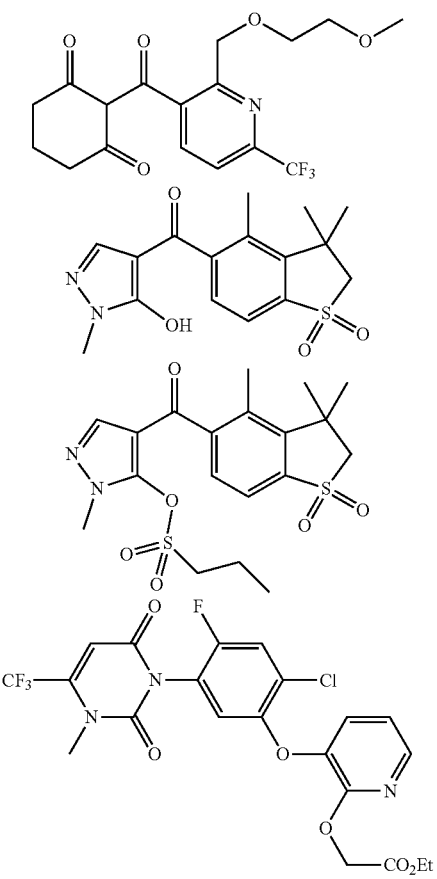

Examples for plant growth regulators are:

Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyl-oxyacetic acid, nitrophenolate-mixture, paclobutrazol, N-(2-phenylethyl)-beta-alanine, N-phenyl-phthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

The safeners are preferably selected from the group consisting of:

S1) compounds of the formula (S1)

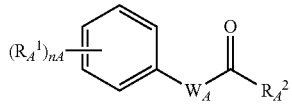

where the symbols and indices have the following meanings:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of $(W_A^1)$ to $(W_A^4)$,

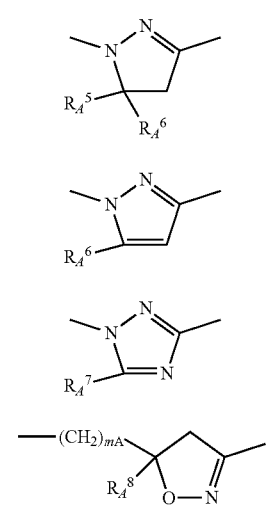

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical having preferably a total of 1 to 18 C-atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr(-diethyl)"), and related compounds, as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the type of the triazolecarboxylic acids ($S1^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620; e) compounds of the type of the 5-benzyl- or 5-phenyl-2-isoxazoline-3-carboxylic acid or the 5,5-diphenyl-2-isoxazoline-3-carboxylic acid ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2)

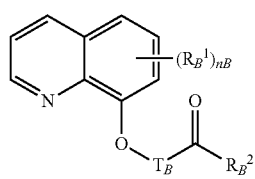

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;

$R_B^3$ is hydrogen or an unsubstituted or substituted aliphatic hydrocarbon radical having preferably a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$- or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the type of the 8-quinolinoxyacetic acid (S2$^a$), preferably 1-methylhexyl (5-chloro-8-quinolinoxy) acetate (common name "cloquintocet-mexyl" (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;

b) compounds of the type of the (5-chloro-8-quinolinoxy) malonic acid (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

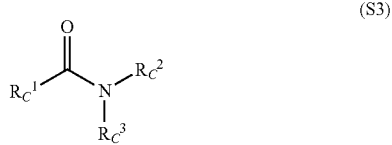

(S3)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the type of the dichloroacetamides which are frequently used as pre-emergence safeners (soil-acting safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8) "diclonon" (dicyclonon) or "BAS145138" or "LAB 145138" (S3-9) (3-dichloroacetyl-2,5,5-trimethyl-1,3-diazabicyclo[4.3.0]nonane) from BASF, "furilazole" or "MON 13900" ((RS)-1-dichloroacetyl-3,3,8a-trimethylperhydropyrrolo[1,2-a] pyrimidin-6-one) (S3-10) and also its (R)-isomer (S3-11).

S4) N-Acylsulphonamides of the formula (S4) and their salts

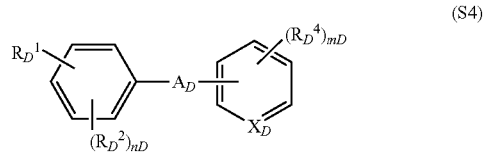

(S4)

where the symbols and indices have the following meanings:

$A_D$ is $SO_2$—$NR_D^3$—$CO$ or $CO$—$NR_D^3$—$SO_2$;

$X_D$ is CH or N;

$R_D^1$ is $CO$—$NR_D^5R_D^6$ or $NHCO$—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;
$v_D$ is 0, 1, 2 or 3;

from among these, preference is given to compounds of the type of the N-acylsulphonamides, for example of the formula (S4$^a$) below, which are known, for example, from WO-A-97/45016

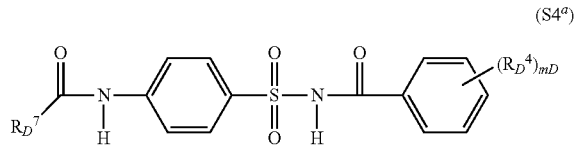

in which
$R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$;
$m_D$ is 1 or 2;
$v_D$ is 0, 1, 2 or 3;
and also
acylsulphamoylbenzamides, for example of the formula (S4$^b$) below, which are known, for example, from WO-A-99/16744,

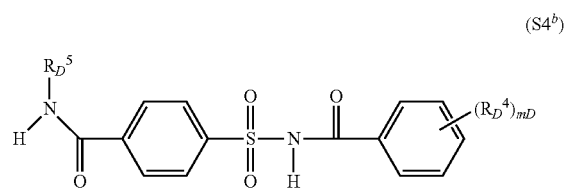

for example those in which
$R_D^5$=cyclopropyl and $(R_D^4)$=2-OMe ("cyprosulphamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and also
compounds of the type of the N-acylsulphamoylphenylureas of the formula (S4$^c$), which are known, for example, from EP-A-365484,

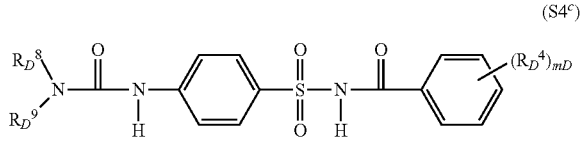

in which
$R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl,
$R_D^4$ is halogen, $(C_1-C_4)$-alkyl, $(C_1-C_4)$-alkoxy, $CF_3$,
$m_D$ is 1 or 2;
for example
1-[4-(N-2-methoxybenzoylsulphamoyl)phenyl]-3-methylurea,
1-[4-(N-2-methoxybenzoylsulphamoyl)phenyl]-3,3-dimethylurea,
1-[4-(N-4,5-dimethylbenzoylsulphamoyl)phenyl]-3-methylurea,
and also
N-phenylsulphonylterephthalamides of the formula (S4$^d$), which are known, for example, from CN 101838227,

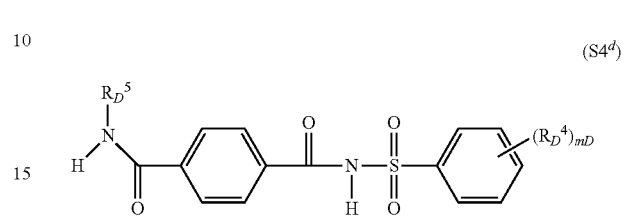

e.g. such compounds in which
$R_D^4$ is halogen, $(C_1-C_4)$-alkyl, $(C_1-C_4)$-alkoxy, $CF_3$;
$m_D$ is 1 or 2;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

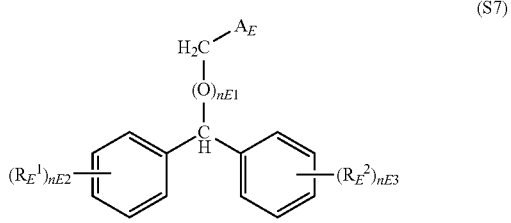

where the symbols and indices have the following meanings:
$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium,
$n_E^1$ is 0 or 1;
$n_E^2$, $n_E^3$ independently of one another are 0, 1 or 2,
preferably:
diphenylmethoxyacetic acid,
ethyl diphenylmethoxyacetate, methyl diphenylmethoxyacetate (CAS Reg. No.: 41858-19-9) (S7-1).

S8) Compounds of the formula (S8), as described in WO-A-98/27049,

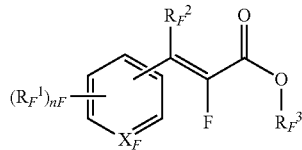

in which $X_F$ is CH or N, $n_F$ is, if $X_F$=N, an integer from 0 to 4 and
is, if $X_F$=CH, an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ is CH, $n_F$ is an integer from 0 to 2, $R_F^1$ is halogen, $(C_1-C_4)$-alkyl, $(C_1-C_4)$-haloalkyl, $(C_1-C_4)$-alkoxy, $(C_1-C_4)$-haloalkoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy;

or salts thereof,

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula (S10$^a$) or (S10$_b$) as described in WO-A-2007/023719 and WO-A-2007/023764

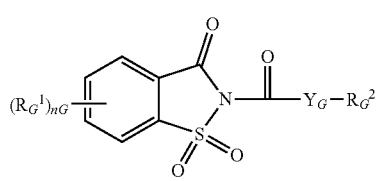

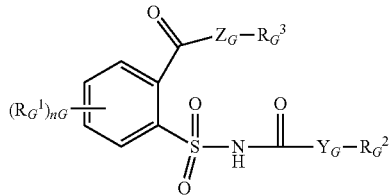

in which $R_G^1$ is halogen, $(C_1-C_4)$-alkyl, methoxy, nitro, cyano, $CF_3$, $OCF_3$ $Y_G$, $Z_G$ independently of one another are O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl; benzyl, halobenzyl, $R_G^3$ is hydrogen or $(C_1-C_6)$-alkyl.

S11) Active compounds of the type of the oxyimino compounds (S11), which are known as seed dressings, such as, for example, "oxabetrinil" ((Z)-1,3-dioxolan-2-yl-methoxyimino-(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxyimino (phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):

"naphthalic anhydrid" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL 304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage, "MG 191" (CAS Reg. No.: 96420-72-3) (2-dichloromethyl-2-methyl-1,3-dioxolane) (S13-5) from Nitrokemia, which is known as safener for corn, "MG 838" (CAS Reg. No.: 133993-74-5) (2-propenyl 1-oxa-4-azaspiro[4.5]decane-4-carbodithioate) (S13-6) from Nitrokemia, "disulphoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active compounds which, besides a herbicidal effect against harmful plants, also have a safener effect on crop plants such as rice, such as, for example, "dimepiperate"

or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "cumyluron"="JC-940" (3-(2-chlorophenylmethyl)-1-(1-methyl-1-phenylethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulphonyl)benzene) from Kumiai, (CAS Reg. No. 54091-06-4), which is known as safener against some herbicide damage in rice.

S15) Compounds of the formula (S15) or its tautomers,

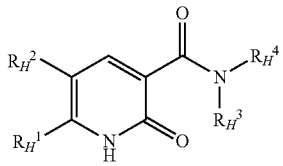

(S15)

which are known, for example, from WO-A-2008/131861 and WO-A-2008/131860, in which $R_H^1$ is $(C_1-C_6)$-haloalkyl, $R_H^2$ is hydrogen or halogen, $R_H^3$, $R_H^4$ independently of one another are hydrogen, $(C_1-C_{16})$-alkyl, $(C_2-C_{16})$-alkenyl or $(C_2-C_{16})$-alkynyl, where each of the 3 last-mentioned radicals is unsubstituted or substituted by one or more radicals from the group consisting of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di-[$(C_1-C_4)$-alkyl]-amino, [$(C_1-C_4)$-alkoxy]-carbonyl, [$(C_1-C_4)$-haloalkoxy]-carbonyl, unsubstituted or substituted $(C_3-C_6)$-cycloalkyl, unsubstituted or substituted phenyl, and unsubstituted or substituted heterocyclyl;

or $(C_3-C_6)$-cycloalkyl, $(C_4-C_6)$-cycloalkenyl, $(C_3-C_6)$-cycloalkyl which is at one site of the ring condensed with a 4 to 6-membered saturated or unsaturated carbocyclic ring, or $(C_4-C_6)$-cycloalkenyl which is at one site of the ring condensed with a 4 to 6-membered saturated or unsaturated carbocyclic ring, where each of the 4 last-mentioned radicals is unsubstituted or substituted by one or more radicals from the group consisting of halogen, hydroxy, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di-$(C_1-C_4)$-alkyl]-amino, [$(C_1-C_4)$-alkoxy]-carbonyl, [$(C_1-C_4)$-haloalkoxy]-carbonyl, unsubstituted or substituted $(C_3-C_6)$-cycloalkyl, unsubstituted or substituted phenyl, and unsubstituted or substituted heterocyclyl; or $R_H^3$ is $(C_1-C_4)$-alkoxy, $(C_2-C_4)$-alkenyloxy, $(C_2-C_6)$-alkynyloxy or $(C_2-C_4)$-haloalkoxy, and $R_H^4$ is hydrogen or $(C_1-C_4)$-alkyl, or $R_H^3$ and $R_H^4$ together with the directly bound N-atom are a 4 to 8-membered heterocyclic ring, which can contain further hetero ring atoms besides the N-atom, preferably up to two further hetero ring atoms from the group consisting of N, O and S, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy, and $(C_1-C_4)$-alkylthio.

S16) Active compounds which are primarily used as herbicides, but also have safener effect on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

EXAMPLES

In an exemplary manner, some synthesis examples of compounds of the general formulae (G1) and (G2) are described below. In the examples, the amounts (including percentages) refer to the weight, unless especially stated otherwise.

The symbols ">" and "<" mean "greater than" and "smaller than", respectively. The symbol "≥" means "greater than or equal to", the symbol "≤" means "smaller than or equal to".

If, in the context of the description and the examples, the terms "R" and "S" are given for the absolute configuration on a centre of chirality of the stereoisomers of the formulae (G1) and (G2), this RS nomenclature follows, unless defined differently, the Cahn-Ingold-Prelog rule.

In the context of the present invention and in the Tables 1 to 3 mentioning specific and preferred compounds according to the present invention, the following abbreviations are used:

H=hydrogen
Me=methyl or $CH_3$
Et=ethyl
Pr=propyl
Bu=butyl
nAlkyl=n-alkyl, e.g. nPr=n-propyl
cAlkyl=cycloalkyl, e.g. cPr=cyclopropyl, cHexyl=cyclohexyl
iAlkyl=isoalkyl, e.g. iPr=isopropyl
tAlkyl=tertiary alkyl, e.g. tBu=tert-butyl
Ac=acetyl
F, Cl, Br, I=fluorine, chlorine, bromine and iodine, respectively, in accordance with the conventional chemical atom symbol
MeO or OMe=methoxy
CN=cyano
$NO_2$=nitro
Ph=phenyl
diHal=diHal, e.g. diF=difluoro
triHal=triHal, e.g. triF=trifluoro
—CCH=ethinyl (—C≡CH)

The position of a substituent, e.g. at the phenyl ring in position 2, is stated as a prefix to the symbol or the abbreviation of the radical, for example
2-Cl=2-chloro
2-Me=2-methyl Numerations of the substituent positions for di- or trisubstituted substitution patterns are analogously stated as a prefix, for example
2,3-Cl$_2$=2,3-dichloro (e.g. as substitution at the phenyl ring)
2,4-diF=2,4-difluoro (e.g. as substitution at the phenyl ring)
2,4-F$_2$=2,4-difluoro (e.g. as substitution at the phenyl ring)
2,4,6-triF=2,4,6-trifluoro (e.g. as substitution at the phenyl ring)
2-F-4-Cl=2-fluoro, 4-chloro (e.g. as substitution at the phenyl ring)
5-F-2-Me=5-fluoro, 2-methyl (e.g. as substitution at the phenyl ring)

Other abbreviations are to be understood analogously to the examples stated above.

In addition, the customary chemical symbols and formulae apply, such as, for example, CH$_2$ for methylene or CF$_3$ for trifluoromethyl or OH for hydroxyl.

Correspondingly, composite meanings are defined as composed of the abbreviations mentioned, for example
4-CF$_3$-cHexyl=4-trifluoromethyl-cyclohexyl
Further, the following abbreviations are used:
DCM=dichloromethane
DMF=dimethylformamide
DMSO=dimethylsulfoxide
T3P=propylphosphonic anhydride
THF=tetrahydrofuran NMR-Peak lists 1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:
δ1 (intensity1); δ2 (intensity2); . . . ; δi (intensityi); . . . ; δn (intensityn)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, tetramethylsilane and/or the chemical shift of the solvent was used, especially in the case of spectra measured in DMSO (Dimethyl sulphoxide). Therefore in NMR peak lists, tetramethylsilane peak can occur, but not necessarily The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists can be found in the publication "Citation of NMR Peaklist Data within Patent Applications" of the Research Disclosure Database Number 564025.

The compounds according to the present invention, such as described in the Tables 1 to 3, are obtained according to or analogously to the following chemical synthesis examples.

(A) Chemical Synthesis Examples

Selected Examples

1. Synthesis of 3-amino-6-(cyclohexylmethyl)-4-(4-fluorophenyl)isothiazolo[5,4-c]pyridin-7-one (Compound No. I-71)

Scheme 9 illustrates the steps (i) to (viii) described in detail in the examples 1.1 to 1.8:

Scheme 9

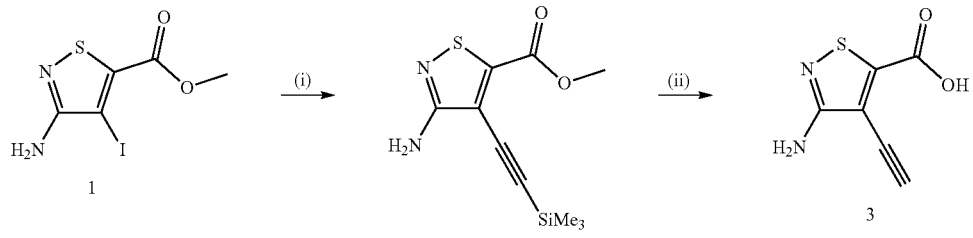

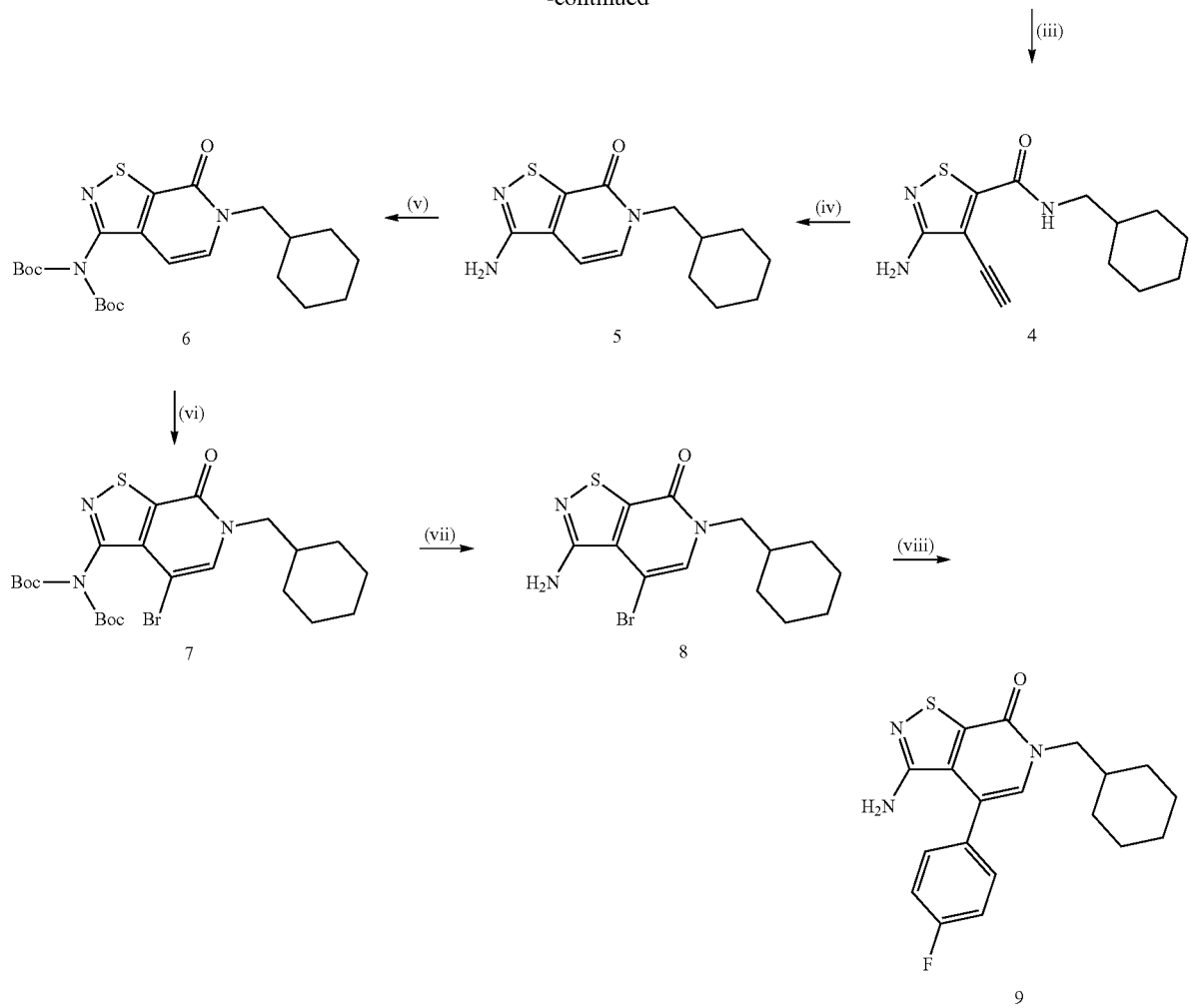

1.1 Step (i)=Synthesis of methyl 3-amino-4-prop-1-ynyl-isothiazole-5-carboxylate To a stirred degassed solution of 650 mg of ester 1 (2.3 mmol) in dry DMF (11 mL) were successively added 161 mg of palladium (II) diphenylphosphine dichloride (0.23 mmol), 44 mg of copper iodide (0.23 mmol), 0.64 mL of triethylamine (4.6 mmol) and 0.65 mL of ethynyltrimethylsilane (4.6 mmol). The reaction mixture was then stirred at 100 degrees for 1 h. The solution was cooled to rt and partitioned between a saturated aqueous solution of ammonium chloride and 10% dichloromethane in heptane. The aqueous phase was extracted twice with 10% dichloromethane in heptane and the combined organic extracts were dried over sodium sulfate, filtered, concentrated and purified by column chromatography. Yield: 486 mg (83% of theory).

$^1$H-NMR (400 MHz, CDCl$_3$ δ, ppm) 4.92 (br. s, 2H), 3.92 (s, 3H), 0.30 (s, 9H).

1.2 Step (ii)=Synthesis of 3-amino-4-ethynyl-isothiazole-5-carboxylic acid

To a stirred solution of 8.0 g of ester 2 (31 mmol) in THF (80 mL) and MeOH (80 mL) was added 42 mL of a 2 M aqueous solution of sodium hydroxide (94 mmol). The reaction mixture was then stirred at rt for 2 h. The mixture was concentrated and the residue partitioned between a 2 M aqueous solution of HCl and EtOAc. The aqueous phase was extracted twice with EtOAc and the combined organic extracts were dried over sodium sulfate, filtered and concentrated. The corresponding acid was engaged in the next step without further purification. Yield: 5.2 g (99% of theory).

$^1$H-NMR (400 MHz, DMSO δ, ppm) 13.9 (br. s, 1H), 6.42 (br. s, 2H), 4.68 (s, 1H).

1.3 Step (iii)=Synthesis of 3-amino-N-(cyclohexylmethyl)-4-ethynyl-isothiazole-5-carboxamide To a stirred solution of 3.0 g of acid 3 (18 mmol) in THF (93 mL) was added successively 16 mL of T3P (27 mmol, 50% in THF), 6.2 mL of triethylamine (45 mmol) and 3.5 mL of cyclohexylmethanamine (27 mmol). The reaction mixture was then stirred at 55 degrees for 2 h. The mixture was concentrated and the residue partitioned between a 2 M aqueous solution of HCl and EtOAc. The aqueous phase was extracted twice with EtOAc and the combined organic extracts were dried over sodium sulfate, filtered, concentrated and purified by column chromatography. Yield: 3.5 g (73% of theory).

¹H-NMR (400 MHz, DMSO δ, ppm) 8.08 (t, 1H), 6.40 (br. s, 2H), 4.82 (s, 1H), 3.12 (t, 2H), 1.72-1.61 (m, 5H), 1.53-1.48 (m, 1H), 1.22-1.11 (m, 3H), 0.98-0.92 (m, 2H).

1.4 Step (iv)=Synthesis of 3-amino-6-(cyclohexylmethyl)isothiazolo[5,4-c]pyridin-7-one To a stirred solution of 5.8 g of alkyne 4 (22 mmol) in THF (51 mL) was added 55 mL of a 1 M solution of tetrabutylammonium fluoride in THF (55 mmol). The reaction mixture was then stirred at rt for 1 h. Water was added and the resulting precipitate was collected by filtration and washed once with DCM. Yield: 4.5 g (75% of theory).

¹H-NMR (400 MHz, DMSO δ, ppm) 7.54 (d, 1H), 6.86 (d, 1H), 6.83 (br. s, 2H), 3.83 (d, 2H), 1.82-1.53 (m, 6H), 1.20-1.00 (m, 3H), 0.97-0.92 (m, 2H).

1.5 Step (v)=Synthesis of 6-(cyclohexylmethyl)-3-(dimethylamino)isothiazolo[5,4-c]pyridin-7-one To a stirred suspension of 5.1 g of amine 5 (19 mmol) in THF (150 mL) was added successively 47 mg of dimethylaminopyridine (0.39 mmol), 8.1 mL of triethylamine (58 mmol) and 11 g of di-tert-butyldicarbonate (48 mmol). The reaction mixture was then stirred at rt for 2 h. The mixture was partitioned between a saturated aqueous solution of ammonium chloride and EtOAc. The aqueous phase was extracted twice with EtOAc and the combined organic extracts were dried over sodium sulfate, filtered, concentrated and purified by column chromatography. Yield: 7.7 g (86% of theory).

¹H-NMR (400 MHz, DMSO δ, ppm) 7.66 (d, 1H), 6.65 (d, 1H), 3.89 (d, 2H), 1.83-1.50 (m, 6H), 1.35 (s, 18H), 1.23-1.10 (m, 3H), 1.07-0.92 (m, 2H).

1.6 Step (vi)=Synthesis of 4-bromo-6-(cyclohexylmethyl)-3-(dimethylamino)isothiazolo[5,4-c]pyridin-7-one To a stirred suspension of 7.7 g of pyridone 6 (17 mmol) in DMF (168 mL) was added 3.3 g of N-bromosuccinimide (18 mmol) and the reaction mixture was then stirred at rt for 4 h. The mixture was concentrated and the residue partitioned between water and EtOAc. The aqueous phase was extracted twice with EtOAc and the combined organic extracts were dried over sodium sulfate, filtered, concentrated and purified by column chromatography. Yield: 8.0 g (88% of theory).

¹H-NMR (400 MHz, DMSO δ, ppm) 8.05 (s, 1H), 3.89 (d, 2H), 1.83-1.50 (m, 6H), 1.35 (s, 18H), 1.23-1.10 (m, 3H), 1.07-0.92 (m, 2H).

1.7 Step (vii)=Synthesis of 3-amino-4-bromo-6-(cyclohexylmethyl)isothiazolo[5,4-c]pyridin-7-one To a stirred solution of 8.0 g of carbamate 7 (15 mmol) in DCM (135 mL) was slowly added 7.9 mL of trifluoroacetic acid (103 mmol) and the reaction mixture was then stirred at rt for 3 h. The mixture was concentrated and the residue partitioned between EtOAc and a 2 M aqueous solution of sodium hydroxide. The aqueous phase was extracted twice with EtOAc and the combined organic extracts were dried over sodium sulfate, filtered and concentrated. Yield: 4.7 g (93% of theory).

¹H-NMR (400 MHz, DMSO δ, ppm) 7.86 (s, 1H), 6.55 (br. s, 2H), 3.82 (d, 2H), 1.81-1.53 (m, 6H), 1.19-1.10 (m, 3H), 1.02-0.93 (m, 2H).

1.8 Step (viii)=Synthesis of 3-amino-6-(cyclohexylmethyl)-4-(4-fluorophenyl)isothiazolo[5,4-c]pyridin-7-one (I-71)

To a stirred and degassed solution of 0.19 g of bromo pyridone 8 (0.56 mmol) in THF (3.0 mL) was successively added 0.32 g of sodium carbonate (3.0 mmol), 0.20 g of 4-fluorophenylboronic acid (1.5 mmol) and 78 mg of palladium (II) diphenylphosphine dichloride (0.11 mmol). The reaction mixture was then stirred under argon at 80 degrees for 3 h. The mixture was cooled to rt and partitioned between EtOAc and a 2 M aqueous solution of HCl. The aqueous phase was extracted twice with EtOAc and the combined organic extracts were dried over sodium sulfate, filtered, concentrated and purified by column chromatography. Yield: 54 mg (27% of theory).

¹H-NMR (400 MHz, DMSO δ, ppm) 7.49 (dd, 2H), 7.43 (s, 1H), 7.35 (dd, 2H), 5.45 (br. s, 2H), 3.87 (d, 2H), 1.86-1.78 (m, 1H), 1.70-1.58 (m, 5H), 1.24-1.13 (m, 3H), 1.04-0.99 (m, 2H).

2. Synthesis of N-[6-(cyclohexylmethyl)-5-isopropyl-7-oxo-isothiazolo[5,4-c]pyridin-3-yl]-2,2,3,3,3-pentafluoro-propanamide (Compound No. I-21)

Scheme 10 illustrates the steps (i) to (v) described in detail in the examples 2.1 to 2.5:

Scheme 10

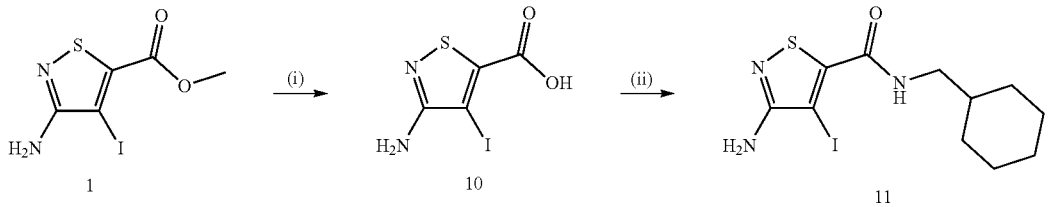

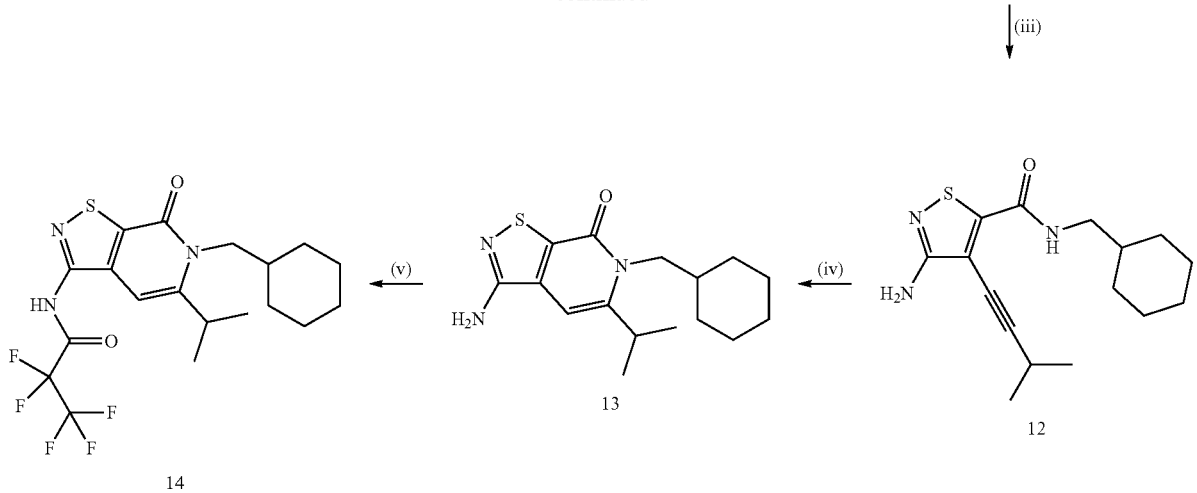

2.1 Step (i)=Synthesis of 3-amino-4-iodo-isothiazole-5-carboxylic acid

To a stirred solution of 21 g of ester 1 (72 mmol) in THF (0.15 L) and MeOH (0.15 L) was added 0.11 L of a 2 M aqueous solution of sodium hydroxide (0.22 mol). The reaction mixture was then stirred at rt for 2 h. The mixture was concentrated and the residue partitioned between a 2 M aqueous solution of HCl and EtOAc. The aqueous phase was extracted twice with EtOAc and the combined organic extracts were dried over sodium sulfate, filtered and concentrated. The corresponding acid was engaged in the next step without further purification. Yield: 19 g (97% of theory).

$^1$H-NMR (400 MHz, DMSO δ, ppm) 13.9 (br. s, 1H), 6.32 (br. s, 2H).

2.2 Step (ii)=Synthesis of 3-amino-N-(cyclohexylmethyl)-4-iodo-isothiazole-5-carboxamide To a stirred solution of 10 g of acid 10 (37 mmol) in THF (0.13 L) was added successively 33 mL of T3P (55 mmol, 50% in THF), 15 mL of triethylamine (0.11 mol) and 5.3 mL of cyclohexylmethanamine (41 mmol). The reaction mixture was then stirred at 55 degrees for 2 h. The mixture was quenched by addition of a 2 M aqueous solution of HCl and the resulting solid was collected by filtration and dried at air. Yield: 12 g (91% of theory).

$^1$H-NMR (400 MHz, DMSO δ, ppm) 8.42 (t, 1H), 6.24 (br. s, 2H), 3.06 (t, 2H), 1.75-1.47 (m, 6H), 1.24-1.12 (m, 3H), 0.98-0.89 (m, 2H).

2.3 Step (iii)=Synthesis of 3-amino-N-(cyclohexylmethyl)-4-(3-methylbut-1-ynyl)isothiazole-5-carboxamide To a stirred degassed solution of 1.0 g of amide 11 (2.7 mmol) in 15 mL of triethylamine (0.11 mol) were successively added 0.19 g of palladium (II) diphenylphosphine dichloride (0.27 mmol), 52 mg of copper iodide (0.27 mmol) and 0.39 g of 3-methyl-1-butyne (5.5 mmol). The reaction mixture was then stirred at 50 degrees for 2 h. The solution was cooled to room temperature and partitioned between a 2 M aqueous solution of HCl and EtOAc. The aqueous phase was extracted twice with EtOAc and the combined organic extracts were dried over sodium sulfate, filtered, concentrated and purified by column chromatography. Yield: 0.63 g (76% of theory).

$^1$H-NMR (400 MHz, DMSO δ, ppm) 7.87 (t, 1H), 6.30 (br. s, 2H), 3.14 (t, 2H), 2.88 (hept, 1H), 1.74-1.47 (m, 6H), 1.25 (d, 6H), 1.24-1.16 (m, 3H), 0.95-0.92 (m, 2H).

2.4 Step (iv)=Synthesis of 3-amino-6-(cyclohexylmethyl)-5-isopropyl-isothiazolo[5,4-c]pyridin-7-one To a stirred solution of 0.60 g of alkyne 12 (2.0 mmol) in THF (8.0 mL) was added 5.9 mL of a 1 M solution of tetrabutylammonium fluoride in THF (5.9 mmol). The reaction mixture was then stirred at rt for 4 h. The mixture was partitioned between a saturated aqueous solution of sodium chloride and EtOAc. The aqueous phase was extracted twice with EtOAc and the combined organic extracts were dried over sodium sulfate, filtered, concentrated and purified by column chromatography. Yield: 0.40 g (66% of theory).

$^1$H-NMR (400 MHz, DMSO δ, ppm) 6.94 (s, 1H), 6.84 (br. s, 2H), 4.02 (m, 2H), 3.11 (hept, 1H), 1.66-1.49 (m, 6H), 1.25 (d, 6H), 1.19-1.04 (m, 5H).

2.5 Step (v)=Synthesis of N-[6-(cyclohexylmethyl)-5-isopropyl-7-oxo-isothiazolo[5,4-c]pyridin-3-yl]-2,2,3,3,3-pentafluoro-propanamide (I-21)

To a stirred suspension of 80 mg of pyridone 13 (0.26 mmol) in DCM (6.0 mL) was added successively 3.2 mg of dimethylaminopyridine (0.03 mmol), 73 μL of triethylamine (0.52 mmol) and 0.16 g of pentafluoropropanoyl-pentafluoropropanoate (0.52 mmol). The reaction mixture was then stirred at rt for 4 h. The mixture was partitioned between water and DCM. The aqueous phase was extracted twice with DCM and the combined organic extracts were dried over sodium sulfate, filtered, concentrated and purified by column chromatography. Yield: 0.11 g (96% of theory).

$^1$H-NMR (400 MHz, DMSO δ, ppm) 12.5 (s, 1H), 6.56 (s, 1H), 4.02 (m, 2H), 3.17 (hept, 1H), 1.67-1.51 (m, 6H), 1.23 (d, 6H), 1.19-1.06 (m, 5H).

NMR Peak Lists

NMR peak lists for compounds according to formulae (G1) and (G2) in the context of the present invention. The numbering refers to Tables 1 to 4 above.

Example I-001: ¹H-NMR(400.0 MHz, d₆-DMSO):
δ = 12.048(0.7); 7.278(0.7); 7.264(3.9); 7.259(3.9); 7.250(3.5); 7.240(1.1); 7.221(15.5); 7.202(0.5); 6.903(2.3); 6.881(3.6); 6.810(0.5); 6.803(4.0); 6.798(1.2); 6.786(1.0); 6.782(2.6); 4.219(1.6); 4.207(3.3); 4.184(1.1); 4.173(1.0); 4.158(0.4); 3.713(16.0); 3.319(47.2); 2.675(0.3); 2.670(0.4); 2.666(0.3); 2.523(1.4); 2.510(28.0); 2.506(56.4); 2.501(74.8); 2.496(54.9); 2.492(27.3); 2.332(0.3); 2.328(0.5); 2.323(0.4); 0.000(2.6)
Example I-002: ¹H-NMR(400.0 MHz, d₆-DMSO):
δ = 11.802(0.5); 7.954(0.4); 7.941(1.0); 7.927(0.5); 7.506(16.0); 7.331(2.1); 7.310(2.1); 6.906(2.7); 6.902(1.1); 6.890(1.0); 6.885(2.6); 6.877(0.3); 6.091(0.5); 6.079(1.2); 6.067(0.5); 5.754(0.4); 4.529(1.9); 4.516(1.9); 4.384(1.7); 4.372(1.7); 3.731(12.7); 3.721(0.8); 3.358(0.4); 3.326(105.0); 2.510(15.2); 2.506(30.5); 2.501(40.4); 2.497(29.4); 2.492(14.4); 0.008(9.4); 0.000(9.4); −0.008(0.4)
Example I-003: ¹H-NMR(400.0 MHz, d₆-DMSO):
δ = 11.975(1.1); 7.440(0.7); 7.424(2.0); 7.406(3.5); 7.379(4.7); 7.360(2.1); 6.907(2.6); 6.885(4.3); 6.819(4.6); 6.797(2.8); 4.194(2.7); 4.182(4.0); 4.137(1.0); 4.124(1.2); 3.725(16.0); 3.518(14.0); 2.670(0.2); 2.501 (108.4); 2.328(0.6); 1.988(1.0); 1.398(0.4); 1.175(0.5); 0.000(12.1)
Example I-004: ¹H-NMR(400.0 MHz, d₆-DMSO):
δ = 7.308(2.5); 7.286(2.7); 6.923(0.5); 6.916(3.4); 6.911(1.2); 6.899(1.2); 6.894(3.3); 6.887(0.6); 6.872(1.4); 4.508(2.3); 4.494(2.2); 3.876(1.0); 3.811(10.2); 3.753(0.4); 3.735(16.0); 3.724(1.4); 3.674(1.6); 3.656(0.8); 3.589(0.4); 3.386(0.3); 3.320(614.7); 3.287(0.5); 2.679(0.7); 2.675(1.5); 2.670(2.1); 2.666(1.6); 2.661(0.7); 2.524(4.8); 2.519(7.7); 2.510(129.3); 2.506(275.1); 2.501(369.1); 2.496(261.7); 2.492(121.8); 2.332(1.5); 2.328(2.1); 2.323(1.5); 2.319(0.7); 1.398(2.8); 1.236(0.4); 0.000(3.3)
Example I-005: ¹H-NMR(400.0 MHz, d₆-DMSO):
δ = 12.008(1.5); 7.330(2.2); 7.324(3.9); 7.318(5.2); 7.280(2.4); 7.271(2.5); 7.262(1.8); 7.256(1.4); 7.222(16.0); 7.188(0.4); 5.755(0.6); 5.129(3.0); 3.712(0.4); 3.318(400.6); 2.670(1.8); 2.505(230.0); 2.501(313.5); 2.496(245.6); 2.327(1.9); 1.988(0.5); 1.298(0.4); 1.258(0.6); 1.235(4.5); 1.174(0.3); 0.853(0.5); 0.146(0.6); 0.008(4.6); 0.000(123.3); −0.150(0.6)
Example I-006: ¹H-NMR(400.0 MHz, CDCl3):
δ = 7.05 (1H), 4.15-4.05 (2H), 3.92-3.85 (2H), 3.30-3.20 (1H), 2.95-2.90 (1H), 2.70-2.60 (1H), 1.85-1.60 (6H), 1.51 (9H), 1.47 (9H), 1.32-0.92 (5H)
Example I-007: ¹H-NMR(400.0 MHz, d₆-DMSO):
δ = 6.27 (2H), 4.98 (1H), 3.87-3.84 (1H), 3.68-3.67 (1H), 3.45-3.42 (1H), 3.22-3.19 (1H), 2.99-2.96 (1H), 2.74-2.69 (2H), 1.73-1.60 (5H), 1.24-0.87 (6H)
Example I-008: ¹H-NMR(400.0 MHz, d₆-DMSO):
δ = 6.916(0.3); 6.894(0.5); 6.418(3.2); 3.898(0.4); 3.880(16.0); 3.863(14.9); 3.840(0.5); 3.820(0.9); 3.812(1.1); 3.782(0.4); 3.759(1.0); 3.754(1.1); 3.746(0.5); 3.735(1.6); 3.723(1.3); 3.716(1.6); 3.706(0.8); 3.698(0.5); 3.692(0.5); 3.683(0.4); 3.675(0.4); 3.652(0.4); 3.649(0.6); 3.642(0.4); 3.629(0.5); 3.620(0.5); 3.441(0.5); 3.319(212.2); 2.675(0.8); 2.670(1.1); 2.666(0.8); 2.524(2.6); 2.510(60.2); 2.506(127.6); 2.501(179.3); 2.497(134.3); 2.492(64.9); 2.333(0.8); 2.328(1.0); 2.324(0.8); 1.896(0.4); 1.433(0.3); 1.351(0.4); 1.336(0.6); 1.298(1.3); 1.258(1.9); 1.249(1.0); 1.244(1.3); 1.235(3.5); 0.854(0.5); 0.008(2.0); 0.000(61.7); −0.008(2.3)
Example I-009: ¹H-NMR(400.0 MHz, d₆-DMSO):
δ = 11.948(0.3); 11.881(0.3); 11.761(0.9); 7.556(1.1); 7.549(1.2); 7.512(16.0); 7.476(2.0); 7.470(2.0); 7.435(1.1); 7.430(1.1); 7.368(0.6); 7.349(0.5); 7.332(0.5); 7.310(0.5); 7.257(0.4); 7.240(0.5); 7.228(0.7); 7.186(0.6); 7.160(0.3); 7.143(0.7); 7.101(0.7); 7.086(0.5); 7.078(0.4); 7.066(0.4); 6.998(0.5); 6.995(0.5); 6.972(0.8); 6.954(0.4); 6.938(0.4); 6.929(0.3); 6.884(0.5); 6.855(0.4); 6.825(2.6); 6.445(0.3); 6.423(0.4); 6.243(0.4); 5.950(0.6); 5.938(1.3); 5.928(0.7); 4.372(2.4); 4.360(2.3); 4.322(0.4); 4.308(0.6); 3.817(1.0); 3.808(0.4); 3.762(0.7); 3.737(0.7); 3.731(1.5); 3.712(16.0); 3.699(0.4); 3.676(0.3); 3.662(0.4); 3.643(0.6); 3.606(1.2); 3.322(502.8); 3.227(0.4); 2.671(2.9); 2.506(403.4); 2.502(523.8); 2.497(395.9); 2.398(0.6); 2.350(0.4); 2.328(3.1); 2.324(2.4); 2.299(0.4); 2.282(0.3); 1.231(1.9); 1.208(0.9); 0.850(0.4); 0.000(2.8)
Example I-010: ¹H-NMR(400.0 MHz, d₆-DMSO):
δ = 8.313(3.8); 7.780(0.5); 7.766(1.0); 7.751(0.5); 7.299(2.6); 7.277(3.0); 6.898(3.0); 6.890(3.5); 6.885(1.2); 6.874(1.1); 6.869(3.2); 6.861(3.0); 6.762(3.2); 4.486(2.1); 4.472(2.4); 3.722(16.0); 3.691(1.4); 3.675(3.1); 3.659(1.5); 3.319(11.4); 3.296(0.7); 2.678(1.3); 2.662(2.6); 2.646(1.1); 2.524(0.4); 2.510(11.8); 2.506(24.8); 2.501(34.3); 2.497(25.7); 2.492(12.4); 0.008(0.5); 0.000(15.5); −0.008(0.6)
Example I-011: ¹H-NMR(400.0 MHz, d₆-DMSO):
δ = 11.566(0.4); 7.925(0.5); 7.310(1.2); 7.289(1.3); 7.099(1.2); 7.097(1.1); 6.901(1.5); 6.896(0.4); 6.884(1.5); 6.880(1.3); 4.510(1.0); 4.496(1.0); 3.726(6.5); 3.317(11.5); 2.524(0.4); 2.511(8.0); 2.506(16.5); 2.502(22.7); 2.497(16.7); 2.493(7.9); 1.989(0.8); 1.398(3.0); 1.175(0.4); 0.323(0.7); 0.315(16.0); 0.306(0.6); 0.000(6.4)

Example I-012: ¹H-NMR(400.0 MHz, d₆-DMSO):
δ = 11.933(1.4); 7.514(3.9); 7.507(5.1); 7.499(4.9); 7.384(2.5); 7.377(2.9); 7.374(2.5); 7.368(2.5); 7.361(2.0); 5.176(3.3); 3.725(0.6); 3.520(16.0); 3.320(91.6); 2.670(0.6); 2.506(76.4); 2.501(97.6); 2.497(77.0); 2.328(0.6); 0.000(10.8)
Example I-013: ¹H-NMR(400.0 MHz, d₆-DMSO):
δ = 16.689(0.8); 8.313(5.1); 3.829(1.0); 3.724(1.2); 3.438(1.0); 3.417(0.8); 3.404(1.0); 3.316(1728.3); 2.674(12.0); 2.670(16.0); 2.666(12.0); 2.633(1.4); 2.510(983.2); 2.506(1932.2); 2.501(2601.2); 2.497(1979.8); 2.387(1.3); 2.373(0.9); 2.332(11.5); 2.328(15.5); 2.323(11.8); 1.350(0.9); 1.298(0.8); 1.276(0.8); 1.259(1.4); 1.235(3.2); 0.853(0.8); 0.483(0.8); 0.146(7.6); 0.039(1.3); 0.008(70.4); 0.000(1641.8); −0.008(73.5); −0.075(0.8); −0.150(7.7); −3.613(0.8)
Example I-014: ¹H-NMR(400.0 MHz, d₆-DMSO):
δ = 11.600(4.8); 9.258(0.4); 8.315(0.6); 7.393(0.4); 7.372(0.5); 7.176(0.4); 7.156(0.4); 6.992(0.5); 6.968(0.5); 6.890(0.5); 6.875(0.4); 6.854(0.4); 6.820(0.4); 6.746(15.7); 6.711(0.7); 6.677(14.0); 4.792(4.5); 4.779(9.9); 4.766(4.8); 4.099(0.7); 4.086(0.8); 3.954(0.4); 3.762(2.1); 3.753(0.6); 3.732(1.3); 3.722(2.0); 3.700(4.4); 3.683(11.2); 3.669(11.5); 3.654(4.6); 3.496(0.4); 3.482(0.5); 3.429(0.6); 3.417(0.8); 3.404(0.6); 3.324(318.2); 3.216(0.4); 3.176(4.0); 3.162(3.8); 2.679(8.6); 2.663(16.0); 2.646(7.2); 2.502(405.0); 2.498(308.4); 2.329(2.4); 1.236(0.6); 0.146(1.3); 0.008(12.5); 0.000(299.4); −0.008(11.0); −0.150(1.4)
Example I-015: ¹H-NMR(400.0 MHz, d₆-DMSO):
δ = 11.607(3.3); 6.735(12.3); 6.625(16.0); 6.270(0.7); 3.602(1.0); 3.315(46.5); 2.671(0.6); 2.525(2.3); 2.520(3.3); 2.512(37.7); 2.507(79.4); 2.502(108.9); 2.498(76.7); 2.493(35.3); 2.457(0.8); 2.452(2.0); 2.445(1.2); 2.429(1.0); 2.401(8.5); 2.384(8.8); 2.334(0.6); 2.329(0.7); 2.325(0.5); 1.776(0.6); 1.768(0.6); 1.760(1.3); 1.649(10.3); 1.623(8.1); 1.238(0.9); 1.207(1.2); 1.160(1.4); 1.156(4.2); 1.108(1.1); 0.970(1.3); 0.943(3.4); 0.937(3.3); 0.917(3.0); 0.887(0.9); 0.000(4.5)
Example I-016: ¹H-NMR(400.0 MHz, d₆-DMSO):
δ = 10.9 (1H), 4.15-4.05 (1H), 3.85-3.78 (1H), 3.59-3.52 (1H), 3.05-2.95 (1H), 2.89-2.79 (1H), 1.47 (9H), 1.46 (9H)
Example I-017: ¹H-NMR(400.0 MHz, d₆-DMSO):
δ = 11.741(1.3); 8.313(1.2); 7.761(2.2); 7.090(3.9); 3.886(16.0); 3.315(151.5); 2.670(3.4); 2.618(0.4); 2.505(411.8); 2.501(552.6); 2.497(428.1); 2.332(2.4); 2.328(3.2); 2.324(2.5); 0.000(29.4)
Example I-018: ¹H-NMR(400.0 MHz, d₆-DMSO):
δ = 6.766(16.0); 6.748(16.0); 3.921(8.0); 3.903(7.9); 3.311(287.1); 3.261(1.7); 2.670(3.0); 2.510(207.1); 2.505(414.0); 2.501(551.4); 2.496(400.3); 2.492(194.4); 2.451(5.4); 2.428(46.7); 2.328(3.9); 1.771(2.5); 1.658(5.8); 1.598(3.7); 1.545(5.7); 1.513(5.6); 1.144(9.0); 1.089(3.5); 1.059(4.5); 1.034(3.5); 0.936(1.5); 0.000(27.3)
Example I-019: ¹H-NMR(601.6 MHz, d₆-DMSO):
δ = 19.088(3.8); 15.405(3.7); 8.440(3.7); 8.308(5.4); 7.439(4.3); 7.094(3.9); 6.907(6.2); 6.844(3.7); 6.803(4.4); 3.813(4.4); 3.770(4.9); 3.732(9.2); 3.724(4.1); 3.697(10.1); 3.462(4.3); 3.448(3.8); 3.358(4.9); 3.304(1645.2); 2.611(14.9); 2.518(32.9); 2.515(32.7); 2.503(1705.9); 2.500(2382.3); 2.498(1947.4); 2.384(14.4); 2.173(6.5); 1.768(4.5); 1.750(7.5); 1.737(5.4); 1.706(6.0); 1.702(4.9); 1.237(3.8); 1.212(4.1); 1.192(4.3); 1.171(4.6); 1.147(3.9); 1.133(5.4); 1.116(16.0); 1.106(15.3); 0.985(4.9); 0.964(5.5); 0.000(69.0); −0.874(3.8)
Example I-020: ¹H-NMR(400.0 MHz, d₆-DMSO):
δ = 7.183(1.1); 6.264(0.6); 3.811(1.0); 2.803(0.7); 2.802(0.7); 2.785(0.7); 2.511(3.7); 2.507(7.9); 2.502(11.0); 2.498(7.6); 2.493(3.3); 1.193(1.3); 1.174(3.0); 1.156(1.4); 1.150(0.7); 1.070(16.0); 0.858(0.5); 0.000(4.1)
Example I-021: ¹H-NMR(400.0 MHz, d₆-DMSO):
δ = 12.466(1.0); 6.565(10.0); 5.755(3.1); 4.023(1.2); 3.316(7.8); 3.185(0.9); 3.168(1.3); 3.152(1.0); 2.521(0.7); 2.512(14.2); 2.508(31.6); 2.503(44.8); 2.498(31.4); 2.494(14.1); 1.666(2.0); 1.592(1.0); 1.539(1.7); 1.514(1.5); 1.241(1.6); 1.229(1.4); 1.225(15.2); 1.194(0.5); 1.176(0.5); 1.135(2.5); 1.118(3.3); 1.095(1.7); 1.064(0.9); 0.858(1.7); 0.840(0.6); 0.000(5.2)
Example I-022: ¹H-NMR(400.0 MHz, d₆-DMSO):
δ = 12.414(2.0); 6.443(7.8); 5.755(16.0); 4.198(6.2); 4.180(6.5); 3.316(4.8); 2.526(1.3); 2.521(1.8); 2.512(22.3); 2.508(48.5); 2.503(68.4); 2.498(49.2); 2.494(23.8); 2.453(1.1); 2.089(1.1); 2.085(1.8); 2.071(1.2); 2.051(0.6); 1.990(0.6); 1.904(1.1); 1.670(3.2); 1.603(4.7); 1.577(3.2); 1.234(3.4); 1.176(1.8); 1.158(4.6); 1.138(6.4); 1.104(3.8); 1.092(5.6); 1.088(5.9); 1.072(5.8); 1.067(5.5); 1.057(2.2); 0.875(0.8); 0.858(2.7); 0.840(1.0); 0.780(1.5); 0.765(4.7); 0.756(4.5); 0.741(1.5); 0.008(1.4); 0.000(46.3); −0.008(1.7)
Example I-023: ¹H-NMR(400.0 MHz, d₆-DMSO):
δ = 6.939(11.7); 6.836(6.5); 4.038(0.6); 4.020(0.8); 3.992(1.1); 3.334(59.5); 3.144(1.2); 3.127(1.7); 3.110(1.2); 3.094(0.5); 2.672(0.7); 2.526(1.7); 2.521(2.5); 2.512(37.1); 2.508(81.9); 2.503(114.3); 2.498(79.9); 2.494(34.8); 2.458(0.7); 2.453(0.8); 2.334(0.5); 2.330(0.7); 2.325(0.5); 1.990(1.4); 1.664(2.8); 1.655(2.7); 1.590(1.3); 1.518(2.2);

-continued 1.491(2.0); 1.254(16.0); 1.237(16.0); 1.193(0.7); 1.175(1.1); 1.157(1.1); 1.123(3.0); 1.100(3.3); 1.072(2.1); 1.042(1.1); 0.008(1.0); 0.000(39.8); −0.008(1.2)

Example I-024: $^1$H-NMR(400.0 MHz, CDCl3): δ = 8.16 (1H), 6.76 (1H), 4.05 (2H), 3.12-3.08 (1H), 2.68-2.50 (2H), 1.74-1.62 (6H), 1.32-1.08 (14H)

Example I-025: $^1$H-NMR(400.0 MHz, CDCl3):
δ = 7.262(80.3); 6.662(2.2); 5.299(3.8); 4.251(5.4); 4.233(5.5); 2.611(0.7); 2.007(0.5); 1.958(1.3); 1.951(1.4); 1.940(2.2); 1.932(1.5); 1.924(1.6); 1.919(1.4); 1.905(0.9); 1.717(2.5); 1.701(2.6); 1.673(3.2); 1.588(4.4); 1.304(7.7); 1.285(16.0); 1.266(7.7); 1.219(1.0); 1.193(3.4); 1.172(4.0); 1.133(1.9); 1.104(1.5); 1.090(1.0); 1.078(3.4); 1.075(3.9); 1.058(3.2); 1.054(3.3); 1.040(1.1); 0.826(3.5); 0.812(3.2); 0.800(0.9); 0.000(6.1)

Example I-026: $^1$H-NMR(400.0 MHz, d$_6$-DMSO):
δ = 6.805(7.9); 6.788(4.5); 3.930(2.0); 3.912(2.0); 3.313(61.7); 2.689(2.5); 2.670(4.4); 2.651(2.6); 2.524(1.61; 2.519(2.3); 2.511 (37.4); 2.506(82.7); 2.502(116.6); 2.497(81.5); 2.492(36.3); 2.461(0.6); 2.456(0.7); 2.452(0.7); 2.447(0.6); 2.333(0.6); 2.328(0.7); 2.324(0.5); 2.074(0.5); 1.760(0.7); 1.752(0.7); 1.743(0.9); 1.724(0.7); 1.694(0.8); 1.676(2.9); 1.657(4.7); 1.638(3.9); 1.619(2.3); 1.601(1.5); 1.591(1.4); 1.525(2.1); 1.496(2.0); 1.169(0.7); 1.132(2.9); 1.102(2.2); 1.073(1.6); 1.038(1.1); 1.016(7.8); 0.998(16.0); 0.980(6.7); 0.955(0.8); 0.936(1.4); 0.918(0.6); 0.000(14.4)

Example I-027: $^1$H-NMR(400.0 MHz, d$_6$-DMSO):
δ = 7.005(3.5); 6.898(1.6); 5.129(4.5); 3.913(1.0); 3.895(1.0); 3.317(13.2); 2.670(0.6); 2.523(1.4); 2.518(2.0); 2.510(30.6); 2.505(67.7); 2.501(95.1); 2.496(66.6); 2.492(30.0); 2.455(0.6); 2.450(0.7); 2.446(0.6); 2.328(0.5); 2.142(16.0); 1.988(1.1); 1.657(0.7); 1.546(0.8); 1.515(0.8); 1.175(0.7); 1.157(0.6); 1.135(1.1); 1.060(0.6); 0.008(1.4); 0.000(63.5); −0.008(2.2)

Example I-028: $^1$H-NMR(400.0 MHz, d$_6$-DMSO):
δ = 6.995(12.9); 6.849(8.0); 4.440(16.0); 4.289(0.8); 4.272(0.7); 3.924(4.7); 3.906(4.8); 3.345(75.2); 3.311(142.5); 3.261(0.9); 3.166(0.5); 2.675(0.9); 2.670(1.4); 2.666(0.9); 2.524(3.0); 2.519(4.4); 2.510(80.8); 2.506(181.0); 2.502(256.8); 2.497(246.9); 2.492(180.0); 2.492(81.0); 2.460(1.3); 2.456(1.7); 2.451(1.9); 2.447(1.7); 2.405(1.6); 2.337(0.7); 2.332(1.3); 2.328(1.6); 2.323(1.3); 2.073(0.7); 1.830(0.8); 1.819(1.0); 1.810(1.2); 1.792(0.9); 1.653(2.9); 1.593(2.0); 1.532(2.8); 1.502(2.8); 1.138(4.5); 1.087(1.7); 1.055(2.2); 1.027(1.7); 0.954(1.0); 0.936(1.9); 0.918(0.8); 0.008(1.6); 0.000(31.2); −0.008(1.0)

Example I-029: $^1$H-NMR(400.0 MHz, CDCl3):
δ = 7.715(1.9); 7.262(69.6); 6.824(3.4); 6.822(6.5); 6.819(3.4); 5.299(5.7); 3.841(7.5); 3.823(7.5); 2.809(1.2); 2.792(3.6); 2.790(3.7); 2.774(3.8); 2.771(3.8); 2.755(1.3); 2.753(1.3); 2.631(0.7); 2.613(1.9); 2.595(1.9); 2.576(0.8); 1.884(0.5); 1.875(0.6); 1.865(0.7); 1.856(0.9); 1.847(0.5); 1.837(0.6); 1.828(0.6); 1.747(1.3); 1.741(1.3); 1.716(2.2); 1.709(2.8); 1.674(2.7); 1.288(7.1); 1.277(7.3); 1.269(16.0); 1.258(14.8); 1.251(8.0); 1.240(7.7); 1.205(2.9); 1.182(2.1); 1.152(0.5); 1.072(0.8); 1.043(1.7); 1.014(1.4); 0.008(0.7); 0.000(26.2); −0.008(0.7)

Example I-030: $^1$H-NMR(400.0 MHz, CDCl3):
δ = 8.621(1.6); 7.519(1.3); 7.260(237.6); 7.210(1.5); 7.158(2.1); 6.996(1.3); 6.868(6.6); 5.299(15.6); 3.850(7.1); 3.831(7.3); 3.804(2.3); 3.786(2.4); 2.765(1.4); 2.746(4.3); 2.728(4.5); 2.709(1.7); 2.660(0.6); 2.639(1.6); 2.637(1.6); 2.620(1.6); 2.601(0.7); 1.860(1.6); 1.851(1.5); 1.842(1.2); 1.832(1.2); 1.823(1.1); 1.814(0.9); 1.786(0.7); 1.742(2.9); 1.719(4.5); 1.687(5.5); 1.661(5.0); 1.600(4.0); 1.364(0.5); 1.346(1.1); 1.328(0.7); 1.292(7.2); 1.274(7.6); 1.254(14.1); 1.235(5.4); 1.224(2.8); 1.205(6.5); 1.186(5.4); 1.070(1.4); 1.040(2.8); 1.009(2.6); 0.987(1.8); 0.899(0.8); 0.882(1.8); 0.864(0.9); 0.069(2.9); 0.008(2.2); 0.000(89.2); −0.008(2.8); −0.050(0.7)

Example I-031: $^1$H-NMR(400.0 MHz, CDCl3):
δ = 8.410(1.2); 7.526(0.6); 7.267(107.2); 7.218(0.6); 7.003(0.6); 6.684(1.5); 5.301(4.1); 3.976(1.4); 3.961(1.4); 2.687(2.9); 2.668(3.4); 2.648(3.2); 2.586(1.0); 2.581(1.1); 2.576(0.9); 1.827(0.6); 1.818(0.8); 1.809(0.6); 1.799(0.5); 1.791(0.5); 1.720(2.1); 1.714(1.9); 1.701(2.9); 1.684(6.6); 1.663(5.6); 1.644(3.3); 1.627(2.3); 1.332(0.5); 1.301(6.6); 1.282(13.8); 1.263(6.7); 1.205(0.8); 1.182(2.9); 1.162(2.2); 1.139(1.2); 1.102(1.4); 1.074(1.1); 1.061(7.7); 1.042(16.0); 1.024(6.7); 0.008(1.1); 0.000(38.3); −0.008(1.1)

Example I-032: $^1$H-NMR(400.0 MHz, CDCl3):
δ = 8.848(1.5); 7.260(81.7); 7.210(0.6); 6.577(8.4); 3.986(2.1); 3.972(2.1); 2.698(3.4); 2.679(4.3); 2.659(3.6); 1.829(0.8); 1.821(0.9); 1.723(2.9); 1.705(3.2); 1.686(4.1); 1.666(5.4); 1.656(4.4); 1.648(4.7); 1.629(2.8); 1.562(4.6); 1.255(2.1); 1.186(3.9); 1.165(3.1); 1.144(1.8); 1.105(2.0); 1.073(8.7); 1.055(16.0); 1.036(7.1); 0.882(0.6); 0.008(1.4); 0.000(29.8); −0.008(1.2)

Example I-033: $^1$H-NMR(400.0 MHz, CDCl3):
δ = 8.077(0.9); 7.261(51.7); 7.211(0.6); 6.902(1.0); 5.299(2.0); 4.442(5.9); 4.055(1.8); 4.037(1.9); 3.392(16.0); 2.582(0.6); 1.716(1.2); 1.668(1.8); 1.649(1.6); 1.642(1.6); 1.308(0.6); 1.289(7.0); 1.271(3.5); 1.242(0.6); 1.210(0.7); 1.186(2.0); 1.164(1.6); 1.130(0.8); 1.099(1.0); 1.070(0.8); 0.000(18.9); −0.008(1.0)

Example I-034: $^1$H-NMR(400.0 MHz, CDCl3):
δ = 7.261(25.2); 6.804(3.6); 5.299(1.8); 4.446(4.6); 4.054(1.1); 4.036(1.1); 3.414(16.0); 1.715(0.9); 1.661(1.2); 1.630(0.9); 1.600(0.6); 1.186(1.4); 1.164(1.0); 1.098(0.6); 0.000(9.2)

Example I-035: 1H-NMR(400.0 MHz, CDCl3):
δ = 7.262(24.0); 6.873(3.2); 5.299(3.7); 5.122(5.4); 3.978(0.8); 3.960(0.8); 2.148(16.0); 1.727(0.7); 1.662(1.1); 1.632(0.9); 1.605(0.8); 1.255(0.5); 1.186(1.2); 1.164(0.9); 1.106(0.6); 0.000(8.8)

Example I-036: $^1$H-NMR(400.0 MHz, d$_6$-DMSO):
δ = 7.013(11.7); 4.499(16.0); 4.318(1.0); 4.026(0.7); 3.955(5.2); 3.936(5.2); 2.671(0.8); 2.666(0.5); 2.524(1.5); 2.520(2.3); 2.511(49.3); 2.506(112.1); 2.502(161.1); 2.497(117.0); 2.493(56.7); 2.452(1.5); 2.333(0.8); 2.329(1.1); 2.324(0.8); 1.909(0.8); 1.808(0.8); 1.798(1.0); 1.789(1.2); 1.770(0.9); 1.651(2.8); 1.593(1.8); 1.533(2.8); 1.502(3.0); 1.235(1.0); 1.132(4.5); 1.079(1.8); 1.050(2.3); 1.025(1.8); 0.000(10.4)

Example I-037: $^1$H-NMR(400.0 MHz, d$_6$-DMSO):
δ = 6.787(16.0); 6.785(16.0); 6.767(13.8); 4.158(9.9); 4.140(10.0); 3.618(0.9); 3.616(0.6); 3.612(0.5); 3.608(0.7); 3.601(2.2); 3.595(0.7); 3.585(1.0); 3.312(76.7); 3.262(0.5); 2.675(0.8); 2.670(1.1); 2.666(0.8); 2.534(0.5); 2.524(2.7); 2.519(3.9); 2.511(65.7); 2.506(145.5); 2.501(205.1); 2.497(143.1); 2.492(63.9); 2.456(1.1); 2.451(1.5); 2.447(1.1); 2.333(0.9); 2.328(1.3); 2.324(1.0); 2.074(4.4); 2.065(0.8); 2.052(1.6); 2.046(1.8); 2.031(3.2); 2.019(1.9); 2.012(1.8); 1.998(0.9); 1.915(0.5); 1.895(1.5); 1.887(1.7); 1.868(1.3); 1.776(1.0); 1.769(0.8); 1.760(2.8); 1.751(2.0); 1.743(1.0); 1.666(4.4); 1.584(5.2); 1.554(4.5); 1.320(0.7); 1.301(0.7); 1.149(6.6); 1.130(6.2); 1.086(3.4); 1.069(2.4); 1.064(3.6); 1.053(8.4); 1.048(8.3); 1.033(7.2); 1.028(7.8); 1.018(2.2); 0.955(1.8); 0.936(3.7); 0.918(1.4); 0.809(2.3); 0.799(6.3); 0.794(7.2); 0.786(6.6); 0.781(6.6); 0.770(2.0); 0.008(1.6); 0.000(62.3); −0.009(2.0)

Example I-038: $^1$H-NMR(400.0 MHz, d$_6$-DMSO):
δ = 7.008(16.0); 6.860(11.0); 4.743(2.7); 4.736(5.0); 4.727(2.9); 4.708(4.6); 4.675(6.0); 4.493(6.1); 4.461(4.8); 3.978(5.4); 3.959(5.5); 3.814(1.1); 3.806(1.4); 3.794(1.2); 3.785(2.5); 3.777(1.8); 3.766(1.3); 3.757(1.4); 3.618(0.6); 3.601(0.9); 3.545(1.2); 3.533(2.1); 3.519(1.5); 3.504(1.8); 3.358(0.7); 3.309(75.9); 3.259(0.9); 2.675(0.5); 2.671 (0.8); 2.666(0.6); 2.551 (0.6); 2.524(2.0); 2.519(3.0); 2.511 (45.1); 2.506(98.5); 2.502(138.0); 2.497(97.8); 2.492(44.8); 2.457(0.8); 2.452(0.9); 2.448(0.6); 2.333(0.6); 2.328(0.8); 2.324(0.6); 2.073(0.9); 1.853(0.9); 1.842(1.2); 1.834(1.4); 1.815(1.1); 1.784(0.9); 1.776(1.1); 1.769(1.3); 1.760(2.4); 1.751(1.7); 1.743(1.6); 1.739(1.6); 1.726(1.1); 1.708(2.3); 1.701(1.8); 1.676(4.7); 1.669(4.4); 1.661(4.4); 1.655(4.3); 1.593(2.4); 1.542(5.6); 1.534(6.3); 1.519(6.3); 1.506(7.3); 1.492(5.1); 1.129(5.2); 1.107(3.3); 1.060(2.5); 1.032(1.9); 0.955(0.6); 0.937(1.2); 0.000(3.5)

Example I-039: $^1$H-NMR(400.0 MHz, d$_6$-DMSO):
δ = 4.117(1.3); 4.100(1.6); 4.080(0.7); 4.013(0.6); 4.000(3.0); 3.979(1.8); 3.963(1.0); 3.872(1.0); 3.854(1.1); 3.839(1.2); 3.821(1.2); 2.869(1.5); 2.862(2.7); 2.856(3.4); 2.757(0.8); 2.740(0.8); 2.724(0.8); 2.707(0.8); 2.510(20.4); 2.505(50.8); 2.500(75.8); 2.496(57.3); 2.491(29.1); 2.455(1.2); 2.450(1.2); 2.446(1.0); 2.332(0.6); 2.327(0.8); 2.323(0.7); 2.238(0.6); 2.218(0.6); 2.214(1.0); 2.201(1.2); 2.195(3.0); 2.183(3.2); 2.176(3.3); 2.164(3.2); 2.158(1.4); 2.145(1.2); 2.141(0.7); 2.122(0.7); 2.040(1.6); 1.908(2.4); 1.723(0.8); 1.694(1.8); 1.678(1.8); 1.670(1.8); 1.660(1.6); 1.652(1.4); 1.626(2.0); 1.596(1.4); 1.298(1.0); 1.284(0.8); 1.236(1.7); 1.200(0.9); 1.168(1.8); 0.998(0.8); 0.972(1.1); 0.965(7.5); 0.954(0.9); 0.946(16.0); 0.928(7.1); 0.890(0.7); 0.863(0.6); 0.008(2.1); 0.000(51.5); −0.009(1.0)

Example I-040: $^1$H-NMR(400.0 MHz, d$_6$-DMSO):
δ = 9.625(16.0); 8.705(0.5); 7.789(15.1); 7.184(7.6); 6.905(1.1); 5.468(1.4); 4.408(7.2); 4.390(7.1); 4.012(0.7); 3.993(0.6); 3.633(1.1); 3.615(1.1); 3.608(1.2); 3.591(1.2); 3.305(91.5); 3.256(0.5); 2.674(2.1); 2.669(3.1); 2.665(2.2); 2.660(1.0); 2.555(2.0); 2.551(1.8); 2.523(8.0); 2.518(11.4); 2.509(165.2); 2.505(359.0); 2.500(501.6); 2.496(355.1); 2.491(162.9); 2.460(3.0); 2.456(3.5); 2.451(3.3); 2.447(1.6); 2.385(0.6); 2.381(0.6); 2.332(2.1); 2.327(3.0); 2.322(2.1); 2.318(1.0); 2.072(0.8); 1.645(3.3); 1.626(3.0); 1.591(2.0); 1.572(1.9); 1.526(2.7); 1.493(2.8); 1.369(0.7); 1.355(2.7); 1.298(0.6); 1.259(1.1); 1.236(3.9); 1.207(2.9); 1.189(6.2); 1.172(3.6); 1.125(3.3); 1.105(5.0); 1.081(2.4); 1.043(1.5); 1.011(2.0); 0.986(1.7); 0.954(1.1); 0.919(1.0); 0.902(1.0); 0.879(1.0); 0.861(1.1); 0.854(0.8); 0.146(1.2); 0.050(1.4); 0.011(0.6); 0.010(0.9); 0.008(10.1); 0.006(3.3); 0.005(4.0); 0.000(384.5); −0.006(7.3); −0.008(12.6); −0.011(3.4); −0.013(2.5); −0.014(2.2); −0.014(2.0); −0.015(1.6); −0.016(1.8); −0.018(1.4); −0.022(1.2); −0.025(1.0); −0.026(1.1); −0.034(0.9); −0.049(2.5); −0.120(0.7); −0.150(1.3)

Example I-041: $^1$H-NMR(400.0 MHz, d$_6$-DMSO):
δ = 7.189(5.3); 6.905(4.7); 5.468(4.5); 4.011(2.6); 3.993(2.7); 3.657(1.2); 3.650(1.1); 3.633(3.0); 3.625(1.5); 3.615(3.1); 3.608(3.2); 3.598(1.4); 3.590(3.1); 3.572(1.1); 3.566(1.3); 3.307(44.8); 2.670(0.8); 2.500(127.7);

-continued 2.496(101.7); 2.327(0.8); 1.839(0.6); 1.654(1.7); 1.592(1.1); 1.519(1.8); 1.492(1.5); 1.236(0.5); 1.207(7.8); 1.189(16.0); 1.172(8.0); 1.124(2.6); 1.102(2.9); 1.074(1.7); 1.044(1.0); 0.000(21.5)
Example I-042: $^1$H-NMR(400.0 MHz, d$_6$-DMSO):
δ = 6.882(4.9); 5.752(8.7); 4.750(1.4); 4.729(0.8); 4.718(2.7); 4.540(1.6); 4.507(1.3); 4.019(1.8); 4.001(1.9); 3.759(0.7); 3.751(0.5); 3.503(0.6); 3.305(12.2); 2.583(1.6); 2.565(5.6); 2.547(5.8); 2.529(1.7); 2.524(0.7); 2.519(0.7); 2.510(8.4); 2.506(18.4); 2.501(25.8); 2.497(18.3); 2.492(8.3); 1.704(0.8); 1.680(1.3); 1.665(1.7); 1.603(0.7); 1.576(1.2); 1.548(1.2); 1.532(0.9); 1.508(1.4); 1.486(1.6); 1.262(0.5); 1.245(0.8); 1.168(0.8); 1.145(1.6); 1.124(1.4); 1.085(0.8); 1.055(0.6); 1.028(7.2); 1.010(16.0); 0.992(6.8); 0.858(0.6); 0.000(16.4)
Example I-043: $^1$H-NMR(400.0 MHz, d$_6$-DMSO):
δ = 12.559(3.8); 6.769(16.0); 5.754(2.9); 4.767(9.1); 4.732(7.1); 4.588(6.9); 4.554(5.1); 4.015(0.6); 3.972(5.4); 3.960(5.5); 3.955(5.4); 3.920(0.8); 3.799(1.4); 3.791(1.9); 3.771(3.3); 3.764(2.5); 3.750(2.0); 3.744(2.0); 3.536(1.6); 3.525(3.0); 3.512(2.3); 3.496(2.6); 3.312(14.0); 2.671(0.8); 2.506(98.8); 2.502(136.2); 2.497(104.5); 2.329(0.9); 1.841(2.0); 1.822(1.7); 1.750(1.8); 1.726(2.7); 1.707(3.7); 1.677(6.8); 1.662(7.0); 1.597(3.7); 1.530(10.8); 1.235(4.6); 1.138(7.9); 1.117(6.4); 1.075(4.2); 1.044(3.1); 0.874(0.8); 0.858(2.1); 0.840(1.0); 0.008(1.7); 0.000(52.3); −0.008(3.1)
Example I-044: $^1$H-NMR(400.0 MHz, d$_6$-DMSO):
δ = 10.596(2.9); 5.752(3.5); 3.909(1.2); 3.891(1.3); 3.876(1.3); 3.858(1.2); 3.717(0.5); 3.697(1.6); 3.684(1.3); 3.670(0.6); 3.431(1.3); 3.418(1.3); 3.404(1.7); 3.391(1.5); 3.228(1.7); 3.208(1.7); 3.201(1.6); 3.181(1.5); 2.984(1.0); 2.967(1.0); 2.940(1.7); 2.924(1.5); 2.822(2.3); 2.789(1.3); 2.779(1.7); 2.772(1.5); 2.756(1.2); 2.739(1.1); 2.523(0.8); 2.519(1.2); 2.510(16.4); 2.505(34.7); 2.501(47.8); 2.496(34.4); 2.492(16.2); 2.403(1.0); 2.399(1.1); 2.384(3.1); 2.380(3.1); 2.364(3.4); 2.362(3.2); 2.345(1.3); 2.041(0.8); 1.988(1.2); 1.908(1.9); 1.694(2.3); 1.687(2.3); 1.668(1.8); 1.657(1.8); 1.633(2.2); 1.606(1.7); 1.299(0.5); 1.236(1.7); 1.222(1.0); 1.212(1.0); 1.193(1.8); 1.175(2.5); 1.157(1.7); 1.120(0.7); 1.092(7.5); 1.073(16.0); 1.054(7.2); 1.041(0.6); 1.010(0.9); 0.982(0.7); 0.911(0.9); 0.881(0.7); 0.008(1.0); 0.000(28.4); −0.008(0.9)
Example I-045: $^1$H-NMR(400.0 MHz, d$_6$-DMSO):
δ = 10.630(2.2); 5.752(2.5); 4.083(0.5); 4.069(1.4); 4.061(2.0); 4.054(2.9); 4.049(3.2); 4.030(1.3); 4.022(1.4); 4.011(0.9); 3.893(0.9); 3.875(0.9); 3.860(1.0); 3.841(1.0); 3.103(0.7); 3.086(0.8); 3.060(1.0); 3.042(1.0); 2.801(0.8); 2.784(1.0); 2.773(2.0); 2.751(0.9); 2.730(1.4); 2.524(0.5); 2.519(0.8); 2.510(12.0); 2.506(25.8); 2.501(35.8); 2.496(25.4); 2.492(11.8); 2.396(0.8); 2.390(0.7); 2.376(2.1); 2.371(2.1); 2.357(2.2); 2.352(2.2); 2.338(0.8); 2.333(0.9); 2.176(0.5); 2.157(0.6); 2.153(0.8); 2.137(1.3); 2.134(2.8); 2.118(3.0); 2.115(3.1); 2.100(2.9); 2.096(1.3); 2.081(0.9); 2.076(0.6); 2.058(0.5); 2.041(1.0); 1.908(1.2); 1.698(1.9); 1.688(1.9); 1.681(1.9); 1.664(1.2); 1.654(1.3); 1.632(1.5); 1.606(1.3); 1.299(0.5); 1.236(1.1); 1.217(0.7); 1.210(0.8); 1.178(1.5); 1.167(1.5); 1.090(6.1); 1.071(13.3); 1.052(6.0); 1.016(0.7); 0.989(0.6); 0.925(7.2); 0.906(16.0); 0.888(7.1); 0.008(0.7); 0.000(22.5); −0.008(0.7)
Example I-046: $^1$H-NMR(400.0 MHz, d$_6$-DMSO):
δ = 6.998(6.3); 6.892(0.8); 5.145(8.3); 3.916(2.1); 3.898(2.1); 3.471(1.0); 2.524(0.9); 2.519(1.3); 2.510(26.5); 2.506(58.2); 2.501(81.8); 2.496(58.7); 2.492(27.5); 2.467(6.2); 2.457(0.6); 2.449(6.1); 2.430(2.0); 2.328(0.6); 1.988(1.1); 1.811(0.6); 1.802(0.7); 1.784(0.6); 1.659(1.6); 1.598(1.0); 1.545(1.6); 1.515(1.5); 1.235(1.9); 1.193(0.6); 1.175(1.0); 1.157(1.2); 1.135(2.5); 1.115(1.7); 1.090(8.0); 1.071(16.0); 1.052(7.5); 1.032(1.0); 0.008(0.7); 0.000(26.3); −0.008(0.8)
Example I-047: $^1$H-NMR(400.0 MHz, d$_6$-DMSO):
δ = 12.529(3.8); 6.762(16.0); 5.777(2.7); 5.763(5.9); 5.755(12.0); 5.753(14.0); 4.558(11.3); 4.545(11.7); 3.961(9.2); 3.943(9.7); 3.311(18.3); 2.670(0.9); 2.524(2.1); 2.506(125.3); 2.501(164.6); 2.498(121.5); 2.497(121.0); 2.328(1.0); 1.988(1.0); 1.800(2.3); 1.782(1.9); 1.656(6.0); 1.596(4.0); 1.550(6.1); 1.521(6.0); 1.457(0.5); 1.406(0.6); 1.395(0.7); 1.299(0.6); 1.237(4.6); 1.193(1.0); 1.142(9.1); 1.122(6.4); 1.067(4.6); 1.038(3.6); 0.875(0.8); 0.858(2.2); 0.841(1.1); 0.008(1.0); 0.002(23.2); 0.000(32.7)
Example I-048: $^1$H-NMR(400.0 MHz, d$_6$-DMSO):
δ = 10.786(3.4); 6.932(5.0); 5.706(0.8); 4.526(3.5); 3.967(2.8); 3.949(2.9); 3.508(0.7); 3.326(26.5); 3.116(0.8); 3.104(0.8); 3.098(0.9); 3.086(0.9); 2.674(1.5); 2.669(2.2); 2.665(1.5); 2.523(5.1); 2.518(8.5); 2.509(145.0); 2.505(311.3); 2.500(432.1); 2.496(310.3); 2.491(147.7); 2.472(8.8); 2.453(7.4); 2.435(2.8); 2.332(2.4); 2.327(3.1); 2.322(2.4); 2.072(0.8); 1.988(1.0); 1.798(0.8); 1.655(1.9); 1.597(1.2); 1.546(1.9); 1.514(1.9); 1.298(0.8); 1.258(1.4); 1.236(5.7); 1.194(2.2); 1.176(4.3); 1.158(3.0); 1.130(8.5); 1.111(16.0); 1.093(7.6); 1.063(1.4); 1.029(1.2); 1.009(1.0); 0.854(1.0); 0.836(0.6); 0.146(0.8); 0.008(7.3); 0.000(215.3); −0.008(6.7); −0.150(0.8)
Example I-049: $^1$H-NMR(400.0 MHz, d$_6$-DMSO):
δ = 6.799(4.6); 4.540(5.8); 3.988(2.6); 3.970(2.8); 2.578(1.9); 2.560(6.3); 2.542(6.5); 2.523(3.0); 2.501(52.1); 2.498(40.1); 1.989(0.7); 1.825(0.6); 1.663(1.6); 1.601(1.0); 1.570(1.7); 1.540(1.6); 1.195(0.6); 1.176(1.7); 1.149(2.5); 1.130(2.0); 1.112(1.6); 1.074(1.3); 1.046(1.0); 1.028(7.8); 1.010(16.0); 0.992(7.7); 0.001(15.7); 0.000(16.7)
Example I-050: $^1$H-NMR(400.0 MHz, d$_6$-DMSO):
δ = 6.786(5.6); 6.780(8.0); 3.912(1.6); 3.898(1.6); 3.307(50.7); 2.670(0.7); 2.561(2.8); 2.544(3.2); 2.523(2.3); 2.518(3.2); 2.510(38.2); 2.505(78.1); 2.501(105.2); 2.496(76.0); 2.492(37.4); 2.332(0.5); 2.328(0.6); 1.988(1.2); 1.911(0.8); 1.894(1.1); 1.878(0.8); 1.732(0.7); 1.714(0.6); 1.661(1.7); 1.652(1.7); 1.588(1.2); 1.520(1.8); 1.492(1.7); 1.175(1.0); 1.157(1.2); 1.129(2.1); 1.103(2.0); 1.072(1.6); 1.041(1.0); 0.960(16.0); 0.943(15.7); 0.000(6.8)
Example I-052: $^1$H-NMR(400.0 MHz, CDCl3):
δ = 7.518(2.9); 7.329(0.8); 7.324(4.6); 7.322(5.1); 7.318(2.5); 7.316(2.5); 7.310(5.2); 7.308(6.3); 7.305(4.3); 7.302(7.2); 7.299(6.7); 7.296(1.9); 7.294(2.9); 7.292(3.0); 7.292(3.1); 7.288(7.0); 7.286(6.1); 7.284(1.9); 7.283(1.5); 7.282(1.5); 7.281(1.7); 7.280(1.6); 7.280(1.6); 7.279(1.5); 7.278(1.6); 7.277(1.4); 7.276(1.2); 7.276(1.3); 7.275(1.5); 7.274(1.5); 7.273(1.5); 7.272(1.5); 7.272(1.6); 7.271(1.8); 7.270(2.0); 7.269(2.2); 7.268(2.4); 7.268(2.6); 7.267(3.1); 7.266(3.8); 7.265(4.5); 7.264(5.5); 7.264(7.3); 7.263(10.4); 7.260(500.4); 7.256(17.1); 7.255(13.4); 7.254(10.6); 7.253(8.5); 7.252(7.5); 7.252(6.8); 7.251(6.0); 7.250(5.5); 7.249(5.1); 7.248(4.8); 7.248(4.4); 7.247(4.2); 7.246(3.9); 7.245(3.6); 7.244(3.5); 7.244(3.5); 7.243(3.3); 7.242(3.0); 7.241(2.9); 7.240(2.8); 7.240(2.8); 7.239(2.7); 7.238(2.6); 7.237(2.6); 7.236(2.5); 7.236(2.3); 7.235(2.4); 7.234(2.5); 7.233(2.5); 7.232(2.2); 7.232(2.1); 7.231(1.6); 7.230(1.6); 7.229(1.9); 7.228(1.8); 7.227(1.8); 7.226(1.8); 7.224(1.5); 7.224(1.3); 7.222(1.4); 7.220(1.5); 7.217(0.7); 7.137(1.1); 7.130(8.5); 7.125(2.7); 7.114(3.0); 7.108(15.0); 7.104(3.2); 7.092(2.6); 7.087(6.9); 7.080(0.9); 6.996(2.9); 6.268(8.8); 4.710(3.0); 3.431(15.8); 3.413(16.0); 2.044(2.0); 1.564(4.9); 1.556(5.4); 1.532(7.8); 1.500(2.8); 1.284(0.6); 1.276(1.0); 1.259(2.5); 1.241(0.9); 1.177(0.6); 1.168(1.1); 1.159(1.4); 1.150(1.6); 1.140(2.1); 1.131(1.9); 1.122(1.6); 1.112(1.6); 1.104(1.1); 1.094(0.6); 1.086(0.5); 1.057(3.4); 1.024(4.9); 1.002(2.1); 0.994(2.7); 0.988(1.6); 0.970(4.1); 0.939(4.0); 0.908(3.1); 0.899(2.2); 0.882(1.9); 0.864(0.9); 0.726(1.5); 0.717(1.4); 0.695(3.4); 0.689(3.3); 0.665(3.2); 0.635(1.3); 0.146(0.5); 0.014(0.5); 0.012(0.6); 0.011(0.7); 0.010(0.8); 0.010(1.1); 0.008(6.0); 0.006(1.9); 0.006(2.0); 0.005(2.4); 0.004(3.0); 0.003(4.8); 0.002(8.1); 0.000(193.4); −0.003(13.7); −0.005(5.2); −0.006(4.2); −0.007(3.5); −0.008(6.8); −0.011(2.2); −0.011(2.0); −0.012(1.8); −0.013(1.7); −0.031(0.7); −0.150(0.6)
Example I-053: $^1$H-NMR(400.0 MHz, d$_6$-DMSO):
δ = 8.05 (1H), 3.88 (2H), 1.88-1.50 (5H), 1.35 (18H), 1.19-0.92 (6H)
Example I-054: $^1$H-NMR(400.0 MHz, d$_6$-DMSO):
δ = 7.860(16.0); 6.549(1.7); 5.754(8.5); 3.830(10.8); 3.812(11.1); 3.410(8.6); 2.670(1.0); 2.524(2.0); 2.510(57.3); 2.506(118.7); 2.502(161.7); 2.497(119.8); 2.493(61.4); 2.328(1.0); 1.808(1.0); 1.800(1.2); 1.790(1.4); 1.781(1.8); 1.772(1.7); 1.762(1.3); 1.753(1.2); 1.744(0.7); 1.677(2.9); 1.661(3.9); 1.609(2.3); 1.559(3.7); 1.535(8.2); 1.235(0.5); 1.174(2.0); 1.147(7.0); 1.127(4.6); 1.021(1.5); 0.992(3.2); 0.963(2.6); 0.000(3.5)
Example I-056: $^1$H-NMR(400.0 MHz, d$_6$-DMSO):
δ = 12.377(1.6); 6.614(5.4); 5.754(3.3); 3.948(2.2); 3.932(2.2); 3.311(19.6); 2.621(3.0); 2.603(3.3); 2.524(1.0); 2.506(49.5); 2.502(67.9); 2.497(50.7); 2.493(26.0); 2.452(0.7); 1.882(0.9); 1.866(1.1); 1.849(1.0); 1.832(0.6); 1.752(0.8); 1.663(2.3); 1.655(2.3); 1.589(1.5); 1.534(2.2); 1.508(2.0); 1.236(1.2); 1.175(0.8); 1.157(1.6); 1.136(3.3); 1.115(3.7); 1.088(2.5); 1.058(1.2); 0.989(0.9); 0.972(1.1); 0.953(16.0); 0.936(15.8); 0.901(1.1); 0.884(0.9); 0.858(0.8); 0.000(10.2)
Example I-057: $^1$H-NMR(400.0 MHz, CDCl3):
δ = 7.518(2.5); 7.423(0.6); 7.405(1.6); 7.399(13.8); 7.394(4.6); 7.383(5.4); 7.378(19.8); 7.372(2.4); 7.304(0.6); 7.294(0.6); 7.287(1.3); 7.272(15.7); 7.268(7.9); 7.266(7.8); 7.266(7.9); 7.260(443.3); 7.252(12.6); 7.246(1.7); 7.209(4.6); 6.995(2.5); 6.244(11.5); 4.706(2.2); 3.436(16.0); 3.418(15.8); 2.043(1.8); 1.570(4.6); 1.562(4.4); 1.537(8.1); 1.502(2.6); 1.276(0.9); 1.258(2.2); 1.241(0.7); 1.178(0.7); 1.168(1.2); 1.159(1.5); 1.150(1.6); 1.140(2.2); 1.131(1.8); 1.122(1.6); 1.113(1.6); 1.103(1.0); 1.085(0.6); 1.064(3.6); 1.028(5.0); 1.005(1.8); 0.998(2.6); 0.990(1.4); 0.973(4.4); 0.942(4.1); 0.911(3.1); 0.882(1.8); 0.727(1.6); 0.719(1.5); 0.697(3.7); 0.668(3.3); 0.639(1.2); 0.146(0.6); 0.008(5.4); 0.000(167.6); −0.008(4.4); −0.150(0.5)
Example I-058: $^1$H-NMR(400.0 MHz, CDCl3):
δ = 9.640(1.1); 7.261(6.6); 7.084(1.1); 4.528(0.6); 4.509(0.6); 1.544(0.6); 1.433(16.0); 1.420(0.7); 1.391(0.8); 0.000(2.6)

Example I-059: ¹H-NMR(400.0 MHz, CDCl3):
δ = 7.518(3.0); 7.358(0.6); 7.310(3.2); 7.292(2.6); 7.288(4.1); 7.281(1.1); 7.271(5.5); 7.259(541.3); 7.253(6.2); 7.250(3.8); 7.246(1.0); 7.244(0.8); 7.242(0.6); 7.241(0.5); 7.237(0.6); 7.211(0.6); 6.995(3.1); 6.978(1.9); 6.972(2.3); 6.958(3.2); 6.952(4.5); 6.940(4.4); 6.933(3.4); 6.918(4.4); 6.910(3.2); 6.895(3.3); 6.888(2.5); 6.048(8.6); 4.722(3.1); 3.411(16.0); 3.393(16.0); 2.043(2.0); 1.576(4.8); 1.551(9.1); 1.526(3.7); 1.284(0.7); 1.276(1.1); 1.258(2.7); 1.241(0.9); 1.198(0.9); 1.190(1.2); 1.181(1.6); 1.171(1.7); 1.162(2.1); 1.153(1.8); 1.143(1.6); 1.134(1.5); 1.125(1.0); 1.116(0.7); 1.085(3.8); 1.048(4.8); 1.017(2.2); 1.010(3.4); 1.002(3.1); 0.990(3.3); 0.975(4.6); 0.945(2.7); 0.913(1.0); 0.882(1.5); 0.864(0.7); 0.747(1.6); 0.739(1.5); 0.718(3.8); 0.687(3.4); 0.659(1.2); 0.146(0.7); 0.050(0.5); 0.008(6.0); 0.000(204.7); −0.008(5.9); −0.149(0.6)
Example I-060: ¹H-NMR(400.0 MHz, CDCl3):
δ = 7.518(1.2); 7.424(2.0); 7.420(3.5); 7.416(1.6); 7.408(2.4); 7.404(9.9); 7.400(6.4); 7.385(10.6); 7.362(4.4); 7.359(3.8); 7.345(5.7); 7.333(9.5); 7.330(10.5); 7.329(10.0); 7.314(6.2); 7.312(6.5); 7.260(197.8); 6.996(1.1); 6.348(11.6); 4.726(8.2); 3.444(15.8); 3.426(16.0); 2.043(1.6); 1.535(4.0); 1.528(3.7); 1.512(5.0); 1.504(5.3); 1.496(4.0); 1.284(0.5); 1.276(0.7); 1.258(1.9); 1.241(0.5); 1.170(0.6); 1.161(1.2); 1.151(1.4); 1.142(1.6); 1.133(2.2); 1.124(1.8); 1.114(1.6); 1.105(1.4); 1.096(0.9); 1.087(0.6); 1.006(4.2); 0.976(5.9); 0.951(4.7); 0.920(3.9); 0.890(3.0); 0.882(2.8); 0.864(1.1); 0.858(0.7); 0.693(1.6); 0.685(1.4); 0.663(3.7); 0.656(3.2); 0.633(3.4); 0.603(1.2); 0.008(2.3); 0.000(75.6); −0.008(2.5)
Example I-061: ¹H-NMR(400.0 MHz, d₆-DMSO): δ = 6.80 (1H), 4.79-4.72 (2H), 4.61-4.58 (1H), 4.00 (2H), 3.79-3.70 (1H), 3.53-3.47 (1H), 1.90-1.47 (7H), 1.36 (18H), 1.29-0.84 (9H)
Example I-062: ¹H-NMR(400.0 MHz, CDCl3):
δ = 7.943(1.5); 7.518(3.0); 7.260(556.9); 7.227(0.8); 7.209(3.8); 6.996(3.1); 6.922(1.0); 6.782(2.1); 6.755(1.7); 6.739(1.6); 6.712(1.8); 5.846(3.5); 5.843(3.6); 5.804(3.2); 5.801(3.2); 5.523(2.9); 5.521(2.7); 5.496(2.7); 5.494(2.8); 5.298(10.2); 3.998(1.9); 3.979(2.0); 2.585(1.0); 2.375(0.9); 2.356(1.4); 2.337(1.0); 1.857(0.8); 1.838(0.9); 1.830(1.1); 1.821(1.0); 1.802(1.0); 1.715(2.9); 1.677(2.0); 1.657(3.7); 1.629(3.2); 1.540(3.4); 1.469(0.6); 1.452(0.5); 1.430(0.6); 1.333(1.7); 1.308(7.2); 1.289(14.8); 1.284(5.1); 1.270(8.6); 1.256(16.0); 1.239(3.4); 1.220(2.7); 1.208(3.1); 1.202(3.1); 1.190(4.2); 1.177(4.7); 1.153(4.0); 1.141(3.2); 1.134(4.1); 1.120(2.6); 1.115(3.1); 1.084(1.9); 1.011(0.7); 0.960(0.6); 0.954(0.6); 0.942(0.9); 0.920(0.9); 0.896(1.2); 0.880(3.2); 0.862(1.4); 0.256(1.1); 0.146(0.6); 0.069(13.0); 0.008(5.4); 0.000(217.0); −0.008(7.1); −0.033(0.6); −0.050(1.6); −0.150(0.8)
Example I-063: ¹H-NMR(400.0 MHz, d₆-DMSO):
δ = 7.430(0.7); 6.870(3.0); 6.856(3.7); 5.753(1.0); 4.220(2.3); 4.206(2.2); 4.039(0.6); 4.021(0.6); 3.920(1.7); 3.903(1.7); 3.307(27.2); 2.523(0.9); 2.518(1.4); 2.510(26.9); 2.505(59.0); 2.501(82.5); 2.496(58.8); 2.492(27.3); 2.328(0.5); 2.072(0.8); 1.988(2.4); 1.760(0.5); 1.658(1.6); 1.599(1.0); 1.541(1.4); 1.512(1.4); 1.444(0.6); 1.414(16.0); 1.236(1.4); 1.193(1.0); 1.175(1.8); 1.157(1.5); 1.130(2.2); 1.112(1.5); 1.085(1.1); 1.054(1.2); 1.030(0.9); 0.858(1.0); 0.008(0.7); 0.000(30.5); −0.008(1.1)
Example I-064: ¹H-NMR(400.0 MHz, CDCl3):
δ = 7.519(1.8); 7.260(316.9); 7.228(0.6); 7.210(0.6); 7.084(26.8); 6.996(1.8); 5.434(0.7); 5.299(3.7); 3.860(0.8); 3.826(15.9); 3.807(16.0); 2.978(1.2); 2.903(1.0); 2.901(1.0); 1.894(0.6); 1.884(1.0); 1.875(1.3); 1.866(1.4); 1.856(1.8); 1.847(1.5); 1.838(1.2); 1.828(1.2); 1.819(0.7); 1.809(0.5); 1.761(2.3); 1.754(2.3); 1.729(3.5); 1.720(2.7); 1.702(3.8); 1.676(4.3); 1.672(4.2); 1.567(4.0); 1.554(1.7); 1.394(1.1); 1.284(0.7); 1.277(0.8); 1.254(2.0); 1.246(2.3); 1.215(4.3); 1.188(3.1); 1.157(0.9); 1.072(1.4); 1.043(3.0); 1.013(2.4); 0.990(0.7); 0.982(0.8); 0.008(3.4); 0.000(119.8); −0.008(3.4)
Example I-065: ¹H-NMR(400.0 MHz, CDCl3):
δ = 7.261(21.0); 6.327(3.7); 5.299(0.8); 4.438(2.2); 4.420(2.2); 3.170(12.9); 3.149(0.5); 2.637(1.4); 2.619(4.7); 2.601(4.8); 2.583(1.5); 1.704(0.6); 1.691(0.8); 1.632(16.0); 1.577(0.8); 1.551(2.6); 1.167(6.4); 1.149(13.4); 1.131(5.7); 1.119(0.6); 1.089(0.7); 0.000(8.0)
Example I-066: ¹H-NMR(400.0 MHz, CDCl3):
δ = 7.260(45.4); 4.447(2.1); 4.429(2.1); 3.174(13.0); 1.668(16.0); 1.632(0.5); 1.565(0.7); 1.551(2.0); 1.309(2.4); 1.291(4.7); 1.272(2.3); 1.256(1.3); 1.155(0.8); 1.132(0.8); 1.077(0.6); 0.008(0.5); 0.000(17.9); −0.008(0.5)
Example I-067: ¹H-NMR(400.0 MHz, CDCl3):
δ = 7.260(61.3); 6.776(0.7); 6.748(0.8); 6.747(0.8); 6.734(0.8); 6.732(0.8); 6.705(0.6); 6.390(1.7); 6.389(1.7); 5.796(1.5); 5.794(1.5); 5.754(1.4); 5.752(1.4); 5.552(1.6); 5.549(1.5); 5.524(1.4); 5.522(1.5); 3.992(0.8); 3.975(0.8); 2.640(1.6); 2.622(5.2); 2.604(5.4); 2.585(1.7); 1.742(0.6); 1.734(0.7); 1.721(0.7); 1.671(1.2); 1.644(0.9); 1.536(1.9); 1.189(1.3); 1.169(1.0); 1.159(7.6); 1.141(16.0); 1.123(7.3); 0.008(0.7); 0.000(86.8); −0.008(0.7)

Example I-068: ¹H-NMR(400.0 MHz, d₆-DMSO):
δ = 8.00 (1H), 3.88 (2H), 1.88-1.50 (5H), 1.35 (18H), 1.25-0.87 (6H)
Example I-069: ¹H-NMR(400.0 MHz, d₆-DMSO):
δ = 7.970(1.2); 6.605(0.7); 3.852(0.6); 3.834(0.6); 3.309(6.7); 2.510(4.8); 2.506(10.4); 2.501(14.6); 2.497(10.4); 2.492(4.8); 0.258(16.0); 0.249(0.5); 0.000(6.5)
Example I-070: ¹H-NMR(400.0 MHz, d₆-DMSO):
δ = 7.946(16.0); 6.584(10.6); 4.620(16.0); 3.858(10.1); 3.840(10.3); 3.308(64.4); 2.675(1.0); 2.670(1.4); 2.666(1.0); 2.524(4.4); 2.519(6.4); 2.510(82.6); 2.506(176.8); 2.501(243.7); 2.496(171.6); 2.492(77.4); 2.332(1.1); 2.328(1.5); 2.323(1.0); 1.988(1.6); 1.812(0.9); 1.803(1.0); 1.793(1.2); 1.785(1.6); 1.776(1.3); 1.766(1.1); 1.757(1.0); 1.677(2.5); 1.660(3.2); 1.610(2.0); 1.553(3.0); 1.521(3.2); 1.235(2.0); 1.226(0.8); 1.208(0.6); 1.193(0.8); 1.175(2.5); 1.146(5.9); 1.126(3.8); 1.025(1.2); 0.995(2.7); 0.966(2.2); 0.936(0.7); 0.008(3.5); 0.000(114.8); −0.008(3.4)
Example I-071: ¹H-NMR(400.0 MHz, d₆-DMSO):
δ = 7.689(1.6); 7.671(1.8); 7.658(1.5); 7.640(1.8); 7.569(1.1); 7.550(1.1); 7.514(7.1); 7.500(8.4); 7.492(8.2); 7.484(4.2); 7.479(7.0); 7.426(16.0); 7.370(7.4); 7.364(2.3); 7.348(12.1); 7.331(2.5); 7.325(5.2); 5.452(10.3); 4.038(0.7); 4.021(0.6); 3.880(8.8); 3.861(8.7); 3.308(210.5); 3.257(0.7); 2.674(3.2); 2.670(3.9); 2.665(2.9); 2.523(18.6); 2.509(275.1); 2.505(530.3); 2.500(677.5); 2.496(467.3); 2.491(207.5); 2.449(1.7); 2.445(2.2); 2.332(3.2); 2.327(4.0); 2.323(2.9); 1.988(2.8); 1.819(1.5); 1.666(3.6); 1.610(5.4); 1.576(4.0); 1.237(3.0); 1.192(2.0); 1.175(3.3); 1.157(6.2); 1.132(4.2); 1.045(1.5); 1.016(3.0); 0.986(2.5); 0.875(1.3); 0.858(3.9); 0.841(1.4); 0.146(0.7); 0.008(9.1); 0.000(209.0); −0.008(7.0); −0.051(0.7); −0.150(0.7)
Example I-072: ¹H-NMR(400.0 MHz, d₆-DMSO):
δ = 7.791(1.2); 7.140(16.0); 6.859(12.0); 5.586(6.2); 5.572(6.2); 4.855(2.5); 4.840(3.2); 4.827(2.4); 4.184(1.8); 4.165(2.1); 4.148(1.8); 3.842(1.5); 3.310(147.3); 2.670(2.7); 2.523(8.4); 2.510(160.1); 2.505(340.4); 2.501(467.5); 2.496(329.2); 2.492(148.4); 2.328(2.6); 1.742(1.6); 1.663(4.4); 1.594(2.9); 1.507(2.6); 1.480(2.4); 1.425(14.7); 1.410(14.3); 1.361(2.6); 1.235(5.6); 1.129(6.5); 1.067(3.5); 1.041(2.6); 0.008(7.4); 0.000(228.9); −0.008(6.9)
Example I-073: ¹H-NMR(400.0 MHz, CDCl3):
δ = 7.518(0.8); 7.259(139.7); 7.236(1.5); 7.220(0.5); 7.216(1.8); 6.995(0.8); 6.980(1.2); 6.960(1.1); 6.268(1.2); 4.766(1.8); 4.737(0.6); 2.170(1.5); 1.532(16.0); 1.256(0.9); 0.008(1.6); 0.000(51.8); −0.008(1.6)
Example I-074: ¹H-NMR(400.0 MHz, CDCl3):
δ = 7.518(4.7); 7.477(0.9); 7.459(3.0); 7.453(1.1); 7.443(1.4); 7.440(2.6); 7.436(1.4); 7.402(3.4); 7.383(5.3); 7.365(2.6); 7.362(1.6); 7.358(0.6); 7.311(0.8); 7.293(1.0); 7.290(1.6); 7.259(834.4); 7.227(0.6); 7.211(0.7); 7.175(4.4); 7.158(4.6); 7.154(3.1); 7.048(0.9); 7.029(0.7); 6.995(4.6); 6.869(0.7); 6.847(1.0); 6.825(0.9); 6.804(0.7); 6.787(1.0); 6.770(1.1); 6.762(1.7); 6.746(1.7); 6.738(1.0); 6.722(1.0); 6.394(8.7); 6.358(1.0); 5.199(7.2); 4.777(2.5); 2.170(0.5); 2.044(0.7); 1.536(16.0); 1.284(0.7); 1.255(2.8); 0.146(0.9); 0.008(9.5); 0.000(309.3); −0.008(9.0); −0.150(1.1)
Example I-075: ¹H-NMR(400.0 MHz, CDCl3):
δ = 7.518(1.6); 7.260(272.2); 7.036(1.3); 7.015(2.9); 6.999(3.0); 6.996(3.4); 6.980(1.7); 6.882(0.9); 6.861(0.8); 6.814(1.5); 6.808(2.0); 6.794(2.6); 6.788(3.7); 6.779(3.0); 6.774(2.5); 6.767(2.1); 6.757(3.8); 6.750(2.8); 6.746(2.5); 6.734(2.9); 6.729(2.9); 6.722(3.8); 6.706(3.6); 6.698(2.1); 6.682(2.0); 6.591(1.4); 6.570(1.8); 6.565(1.7); 6.547(1.8); 6.526(1.4); 6.061(7.0); 4.778(16.0); 4.764(4.3); 4.163(1.8); 3.296(0.5); 2.170(2.3); 2.043(0.8); 1.547(1.6); 1.284(0.8); 1.276(0.8); 1.256(4.8); 1.240(0.5); 1.102(0.7); 0.880(1.0); 0.008(3.2); 0.000(101.4); −0.008(3.1)
Example I-076: ¹H-NMR(400.0 MHz, CDCl3):
δ = 7.518(4.0); 7.292(1.2); 7.290(1.1); 7.285(1.2); 7.259(708.1); 7.209(0.7); 7.028(3.6); 7.014(4.7); 7.008(7.4); 6.995(9.4); 6.975(1.6); 6.968(9.8); 6.962(2.6); 6.947(12.8); 6.942(2.7); 6.930(1.8); 6.925(4.7); 6.740(2.1); 6.724(2.3); 6.716(3.6); 6.700(3.5); 6.692(2.2); 6.676(2.0); 6.554(1.6); 6.534(1.8); 6.512(1.8); 6.490(1.5); 6.290(8.1); 4.761(16.0); 4.738(4.0); 2.170(0.9); 1.534(11.4); 1.333(7.0); 1.284(1.2); 1.255(7.8); 0.880(0.8); 0.146(0.9); 0.008(7.6); 0.000(257.0); −0.008(8.0); −0.150(0.9)
Example I-077: ¹H-NMR(400.0 MHz, d₆-DMSO):
δ = 12.284(2.8); 8.033(16.0); 3.880(9.7); 3.862(9.9); 3.309(34.4); 2.674(0.8); 2.670(2.6); 2.665(0.8); 2.523(3.1); 2.519(4.2); 2.510(62.9); 2.505(136.8); 2.501(192.1); 2.496(136.9); 2.492(62.9); 2.332(0.5); 2.328(1.2); 2.323(0.8); 1.834(0.9); 1.826(1.1); 1.816(1.3); 1.807(1.6); 1.798(1.4); 1.788(1.2); 1.780(1.0); 1.666(3.5); 1.612(2.2); 1.581(3.7); 1.552(3.4); 1.236(1.4); 1.182(1.9); 1.154(6.2); 1.134(4.0); 1.112(1.0); 1.040(1.4); 1.011(2.9); 0.982(2.3); 0.875(0.6); 0.858(1.9); 0.841(0.7); 0.008(2.6); 0.000(86.8); −0.008(2.5)
Example I-078: ¹H-NMR(400.0 MHz, d₆-DMSO):
δ = 10.349(3.2); 7.938(9.1); 3.870(4.6); 3.851(4.6); 3.308(47.4); 2.674(0.5); 2.670(0.7); 2.523(2.1); 2.518(3.0); 2.510(39.6); 2.505(85.3); 2.500(118.6); 2.496(83.3); 2.491(37.9); 2.426(1.9); 2.408(6.3); 2.389(6.5); 2.370(2.0); 2.332(0.5); 2.327(0.7); 2.323(0.5); 1.988(0.9); 1.812(0.5);

1.802(0.6); 1.793(0.8); 1.784(0.6); 1.775(0.5); 1.680(1.2); 1.664(1.6);
1.610(1.0); 1.572(1.6); 1.540(1.6); 1.248(1.4); 1.192(0.6); 1.175(1.2);
1.153(2.8); 1.132(1.9); 1.118(7.6); 1.099(16.0); 1.080(6.9); 1.036(0.6);
1.007(1.4); 0.978(1.1); 0.875(0.7); 0.858(2.5); 0.841(0.9); 0.008(1.7);
0.000(55.1); −0.008(1.6)
Example I-079: $^1$H-NMR(400.0 MHz, CDCl3):
δ = 7.518(0.7); 7.291(6.0); 7.260(120.3); 6.996(0.7); 3.849(3.4);
3.831(3.4); 2.707(1.2); 2.689(1.2); 2.680(0.6); 2.662(2.0); 2.644(2.0);
2.626(0.6); 2.539(1.6); 2.521(1.7); 2.503(0.6); 2.494(1.0); 2.476(1.0);
1.775(0.6); 1.744(1.0); 1.736(1.1); 1.701(1.2); 1.534(13.2); 1.256(2.0);
1.228(1.1); 1.208(0.8); 1.158(7.4); 1.140(16.0); 1.122(7.1); 1.058(0.8);
1.028(0.6); 0.008(1.3); 0.000(45.0); −0.008(1.3)
Example I-080: $^1$H-NMR(400.0 MHz, d$_6$-DMSO):
δ = 7.552(16.0); 7.210(4.1); 7.182(4.6); 7.168(4.6); 7.141(3.9);
6.273(14.8); 5.576(7.5); 5.573(7.7); 5.534(7.2); 5.530(6.7); 5.309(8.1);
5.305(7.4); 5.282(7.0); 5.278(7.9); 3.876(14.4); 3.858(15.1); 3.307(210.1);
2.670(4.9); 2.523(13.9); 2.510(264.9); 2.505(567.0); 2.500(785.9);
2.496(553.7); 2.491(251.6); 2.327(4.4); 1.808(2.9); 1.666(5.3); 1.610(3.5);
1.571(5.1); 1.536(5.0); 1.155(9.2); 1.135(5.8); 1.016(4.0); 0.991(3.6);
0.008(9.0); 0.000(287.4); −0.008(8.8)
Example I-081: $^1$H-NMR(400.0 MHz, d$_6$-DMSO):
δ = 12.361(3.2); 7.964(16.0); 3.872(9.8); 3.853(10.0); 3.338(0.6);
3.309(159.7); 2.679(0.7); 2.674(1.7); 2.670(2.4); 2.665(1.6); 2.660(0.7);
2.532(1.5); 2.523(7.0); 2.518(9.8); 2.510(139.2); 2.505(302.8);
2.500(423.1); 2.496(298.7); 2.491(136.8); 2.477(1.8); 2.472(1.2);
2.467(1.0); 2.457(1.1); 2.332(1.9); 2.327(2.6); 2.323(2.0); 2.318(0.9);
2.072(0.8); 1.838(0.9); 1.829(1.2); 1.820(1.3); 1.811(1.6); 1.802(1.4);
1.792(1.1); 1.783(1.0); 1.667(3.5); 1.613(2.2); 1.585(3.8); 1.554(3.4);
1.236(4.8); 1.181(1.8); 1.154(6.1); 1.134(4.1); 1.041(1.4); 1.010(2.9);
0.981(2.3); 0.854(0.6); 0.146(0.7); 0.008(6.4); 0.000(212.9); −0.008(6.0);
−0.150(0.8)
Example I-082: $^1$H-NMR(400.0 MHz, CDCl3):
δ = 7.518(0.6); 7.260(108.8); 7.172(6.0); 6.996(0.6); 3.845(3.1);
3.826(3.1); 2.711(1.2); 2.692(1.3); 2.684(0.6); 2.666(2.0); 2.648(2.0);
2.630(0.6); 2.541(1.7); 2.523(1.7); 2.505(0.6); 2.496(1.0); 2.478(1.0);
1.774(0.5); 1.736(1.0); 1.700(1.1); 1.532(8.3); 1.256(1.2); 1.226(1.0);
1.207(0.7); 1.157(7.2); 1.139(16.0); 1.121(7.0); 1.057(0.7); 1.028(0.6);
0.008(1.1); 0.000(40.3); −0.008(1.2)
Example I-083: $^1$H-NMR(400.0 MHz, d$_6$-DMSO):
δ = 10.418(3.3); 7.865(8.5); 3.862(4.7); 3.844(4.8); 3.309(21.0);
2.524(0.8); 2.519(1.2); 2.510(18.3); 2.506(39.8); 2.501(55.7); 2.496(39.8);
2.492(18.4); 2.409(2.0); 2.390(6.6); 2.372(6.8); 2.353(2.1); 1.988(1.5);
1.818(0.5); 1.808(0.6); 1.800(0.8); 1.791(0.6); 1.781(0.5); 1.772(0.5);
1.680(1.2); 1.666(1.6); 1.612(1.6); 1.574(1.7); 1.542(1.6); 1.258(2.0);
1.247(2.0); 1.193(0.8); 1.175(1.6); 1.157(3.0); 1.154(2.9); 1.134(1.9);
1.112(7.7); 1.094(16.0); 1.075(7.0); 1.038(0.6); 1.008(1.4); 0.988(1.0);
0.979(1.1); 0.875(1.0); 0.858(3.4); 0.840(1.3); 0.008(0.7); 0.000(22.6);
−0.009(0.7)
Example I-084: $^1$H-NMR(400.0 MHz, d$_6$-DMSO):
δ = 10.472(1.6); 7.869(5.5); 3.860(2.9); 3.842(2.9); 3.308(24.3);
2.523(0.6); 2.519(0.9); 2.510(13.5); 2.505(29.4); 2.501(41.2); 2.496(29.3);
2.492(13.4); 2.077(16.0); 1.988(1.3); 1.680(1.5); 1.664(1.0); 1.610(0.6);
1.576(1.0); 1.545(0.9); 1.248(0.8); 1.193(0.6); 1.175(1.1); 1.157(1.9);
1.153(1.8); 1.134(1.1); 1.009(0.8); 0.979(0.6); 0.858(1.4); 0.000(14.0)
Example I-085: $^1$H-NMR(400.0 MHz, CDCl3):
δ = 7.261(40.0); 7.164(5.1); 4.138(4.4); 4.131(0.8); 3.846(2.8); 3.827(2.8);
3.550(16.0); 2.043(2.2); 1.736(0.7); 1.702(0.9); 1.675(0.8); 1.548(8.1);
1.276(0.9); 1.259(1.8); 1.241(0.8); 1.217(0.8); 1.194(0.6); 1.050(0.6);
0.882(1.3); 0.000(14.1)
Example I-086: $^1$H-NMR(400.0 MHz, CDCl3):
δ = 9.441(2.1); 7.261(93.8); 7.222(1.5); 7.213(18.2); 6.997(0.5);
3.860(13.1); 3.842(13.2); 2.043(2.1); 1.894(0.7); 1.885(1.2); 1.875(1.4);
1.866(1.5); 1.856(1.9); 1.848(1.6); 1.838(1.3); 1.828(1.2); 1.820(0.7);
1.771(2.8); 1.741(4.2); 1.700(5.9); 1.673(4.8); 1.552(6.3); 1.323(1.0);
1.304(2.3); 1.265(11.5); 1.219(5.5); 1.195(3.9); 1.164(1.0); 1.082(1.6);
1.054(3.4); 1.023(2.7); 1.000(0.8); 0.993(0.8); 0.899(5.4); 0.882(16.0);
0.864(6.7); 0.008(1.3); 0.000(33.9); −0.008(1.1)
Example I-087: $^1$H-NMR(400.0 MHz, d$_6$-DMSO):
δ = 10.366(2.9); 7.965(7.2); 5.753(16.0); 4.101(13.3); 3.930(3.0);
3.872(3.5); 3.854(3.6); 3.433(31.7); 3.311(8.4); 3.291(5.4); 2.524(0.6);
2.519(0.8); 2.511(12.0); 2.506(26.3); 2.502(36.8); 2.497(25.7);
2.492(11.4); 1.989(1.4); 1.909(1.7); 1.797(0.6); 1.680(0.9); 1.664(1.2);
1.609(0.7); 1.573(1.2); 1.540(1.2); 1.235(0.6); 1.193(0.7); 1.175(1.4);
1.157(2.2); 1.153(2.2); 1.132(1.4); 1.009(1.0); 0.980(0.8); 0.000(11.2)
Example I-088: $^1$H-NMR(400.0 MHz, d$_6$-DMSO):
δ = 12.233(2.1); 8.030(16.0); 3.878(7.8); 3.860(8.1); 3.309(82.4);
2.670(1.3); 2.523(4.3); 2.518(5.8); 2.510(82.0); 2.505(179.1);
2.501(251.2); 2.496(176.0); 2.492(78.1); 2.327(1.4); 1.988(1.9);
1.806(1.4); 1.666(2.8); 1.582(3.2); 1.554(2.9); 1.282(1.4); 1.248(4.8);
1.175(2.4); 1.157(5.0); 1.135(3.3); 1.013(2.4); 0.984(2.1); 0.875(2.5);
0.858(8.6); 0.841(2.9); 0.008(1.9); 0.000(65.2); −0.009(2.0)
Example I-089: $^1$H-NMR(400.0 MHz, d$_6$-DMSO):
δ = 8.150(3.8); 7.649(4.9); 7.623(4.0); 5.957(16.0); 3.517(10.1);
3.498(10.2); 3.363(4.5); 3.346(1.9); 3.312(445.4); 3.263(3.2); 2.674(3.4);
2.670(4.7); 2.665(3.4); 2.556(5.1); 2.552(4.6); 2.547(1.8); 2.534(1.0);
2.523(11.0); 2.518(17.5); 2.510(255.6); 2.505(551.8); 2.501(770.4);
2.496(555.0); 2.492(261.4); 2.461(4.6); 2.456(5.6); 2.452(4.9); 2.447(1.5);
2.417(0.8); 2.400(0.9); 2.332(3.2); 2.328(4.6); 2.323(3.4); 2.222(0.8);
2.213(0.7); 2.178(0.7); 2.166(0.5); 2.124(0.8); 2.072(0.8); 1.860(3.6);
1.669(5.4); 1.620(6.6); 1.594(6.4); 1.298(3.2); 1.259(5.1); 1.235(14.4);
1.191(3.9); 1.162(8.7); 1.140(6.8); 1.012(2.4); 0.982(4.2); 0.953(3.6);
0.929(2.2); 0.854(3.0); 0.836(1.7); 0.000(19.1)
Example I-090: $^1$H-NMR(400.0 MHz, d$_6$-DMSO):
δ = 7.785(3.8); 6.569(2.5); 3.844(2.1); 3.826(2.2); 3.308(15.2); 2.928(0.9);
2.911(1.2); 2.894(0.9); 2.524(0.7); 2.519(1.1); 2.511(14.6); 2.506(31.4);
2.502(43.7); 2.497(30.6); 2.492(13.7); 1.656(0.8); 1.544(0.7); 1.516(0.7);
1.246(16.0); 1.229(15.5); 1.144(1.4); 1.123(0.9); 0.990(0.7); 0.960(0.5);
0.008(0.7); 0.000(24.2); −0.008(0.7)
Example I-091: $^1$H-NMR(400.0 MHz, CDCl3):
δ = 8.084(1.9); 7.548(1.1); 7.542(9.4); 7.537(3.1); 7.526(3.4); 7.521(12.0);
7.514(1.4); 7.484(1.2); 7.468(0.5); 7.463(1.6); 7.370(1.9); 7.365(0.5);
7.356(1.7); 7.350(13.0); 7.345(3.7); 7.334(3.2); 7.329(9.7); 7.322(1.2);
7.260(176.8); 7.016(16.0); 6.996(1.1); 6.898(1.9); 5.298(1.8); 4.415(0.6);
3.903(9.0); 3.885(9.1); 3.876(1.4); 3.858(1.2); 2.043(1.0); 1.924(0.7);
1.916(0.8); 1.905(0.9); 1.896(1.1); 1.888(1.0); 1.878(0.8); 1.869(0.7);
1.766(1.9); 1.734(5.4); 1.702(4.1); 1.545(7.6); 1.284(0.9); 1.276(1.0);
1.258(3.3); 1.255(3.3); 1.241(1.2); 1.222(3.0); 1.202(2.9); 1.158(0.7);
1.088(1.1); 1.060(2.2); 1.031 (1.9); 1.006(0.6); 0.999(0.7); 0.882(1.3);
0.864(0.6); 0.008(1.9); 0.000(64.2); −0.008(1.9)
Example I-092: $^1$H-NMR(400.0 MHz, CDCl3):
δ = 7.374(3.8); 7.369(1.2); 7.358(1.3); 7.353(4.5); 7.347(0.5); 7.270(0.5);
7.269(0.6); 7.268(0.8); 7.260(71.9); 7.255(0.8); 7.254(0.6); 7.104(0.6);
7.098(4.4); 7.092(1.5); 7.081(1.2); 7.076(3.7); 6.955(5.9); 5.298(1.0);
3.886(3.1); 3.868(3.2); 2.295(0.9); 2.277(1.0); 2.268(0.7); 2.250(2.2);
2.232(2.2); 2.216(1.0); 2.198(2.6); 2.180(2.7); 2.161(0.8); 2.152(1.1);
2.134(1.1); 1.743(1.6); 1.710(1.0); 1.537(6.4); 1.259(0.9); 1.227(0.8);
1.210(0.8); 1.194(0.6); 1.057(0.7); 1.034(0.6); 1.026(0.6); 0.991(7.1);
0.973(16.0); 0.955(6.7); 0.008(1.9); 0.000(27.7); −0.008(0.8)
Example I-093: $^1$H-NMR(400.0 MHz, CDCl3):
δ = 7.519(0.9); 7.495(4.1); 7.490(1.4); 7.479(1.6); 7.474(5.5); 7.467(0.7);
7.352(0.7); 7.345(6.0); 7.340(1.8); 7.329(1.5); 7.324(4.3); 7.318(0.5);
7.260(158.8); 7.182(0.8); 6.996(0.9); 3.889(4.2); 3.871(4.2);
2.142(1.5); 1.892(0.5); 1.730(2.2); 1.698(1.4); 1.537(16.0); 1.264(1.4);
1.214(1.2); 1.199(1.0); 1.187(0.9); 1.054(0.9); 1.033(0.8); 0.973(2.7);
0.954(5.4); 0.936(2.6); 0.899(0.7); 0.882(2.5); 0.864(1.0); 0.008(1.8);
0.000(59.3); −0.008(1.6)
Example I-094: $^1$H-NMR(400.0 MHz, d$_6$-DMSO):
δ = 7.182(6.5); 6.262(6.5); 5.755(9.1); 3.812(6.1); 3.794(6.1); 3.314(4.4);
2.823(1.3); 2.805(4.1); 2.786(4.2); 2.767(1.6); 2.526(0.7); 2.522(1.0);
2.513(11.8); 2.508(25.1); 2.504(34.7); 2.499(24.4); 2.495(11.1);
1.912(0.6); 1.810(0.6); 1.801(0.6); 1.792(0.8); 1.783(1.0); 1.774(0.8);
1.764(0.7); 1.755(0.6); 1.675(1.7); 1.659(2.0); 1.606(1.3); 1.596(1.2);
1.560(2.0); 1.529(2.0); 1.234(1.2); 1.195(6.9); 1.176(16.0); 1.158(7.8);
1.149(4.1); 1.128(2.4); 1.032(0.8); 1.003(1.6); 0.974(1.3); 0.000(2.3)
Example I-095: $^1$H-NMR(400.0 MHz, d$_6$-DMSO):
δ = 7.519(0.7); 7.260(111.7); 7.212(7.5); 6.996(0.6); 5.530(2.1);
3.832(6.0); 3.814(6.1); 2.466(3.5); 2.448(7.5); 2.431(3.9); 2.043(0.7);
1.886(0.6); 1.876(0.6); 1.867(0.8); 1.858(0.7); 1.848(0.6); 1.839(0.5);
1.752(1.2); 1.746(1.2); 1.721(2.0); 1.712(2.6); 1.693(4.1); 1.675(7.2);
1.657(6.3); 1.639(3.0); 1.621(0.8); 1.561(1.3); 1.276(0.7); 1.264(0.9);
1.259(1.2); 1.241(1.1); 1.206(2.3); 1.182(1.8); 1.083(7.8); 1.065(16.0);
1.046(8.0); 1.009(1.4); 0.986(0.6); 0.882(1.0); 0.008(1.3); 0.000(41.0);
−0.008(1.6)
Example I-096: $^1$H-NMR(400.0 MHz, d$_6$-DMSO):
δ = 8.651(9.7); 7.897(3.7); 7.878(4.0); 7.530(16.0); 7.519(3.6); 7.500(3.2);
5.482(11.2); 3.895(8.7); 3.877(8.2); 3.311(104.5); 2.671(2.3);
2.505(324.3); 2.501(411.1); 2.497(301.4); 2.328(2.6); 1.988(4.8);
1.669(4.7); 1.609(6.2); 1.584(4.9); 1.175(4.3); 1.156(7.8); 1.023(3.6);
0.992(3.3); 0.000(45.0)
Example I-097: $^1$H-NMR(400.0 MHz, CDCl3):
δ = 7.518(0.7); 7.418(0.5); 7.413(0.8); 7.403(3.4); 7.401(3.5); 7.395(1.6);
7.385(2.2); 7.376(0.5); 7.372(0.7); 7.363(0.5); 7.259(113.4); 7.163(2.2);
7.159(2.5); 7.154(1.1); 7.144(1.5); 7.139(1.0); 6.995(0.6); 6.978(5.7);
5.298(0.8); 3.890(3.5); 3.872(3.5); 2.287(1.1); 2.269(1.1); 2.260(0.6);
2.242(1.9); 2.224(2.0); 2.206(0.6); 2.154(0.6); 2.136(2.3); 2.118(2.4);
2.099(0.8); 2.090(1.3); 2.072(1.3); 1.754(1.6); 1.735(1.8); 1.699(0.6);
1.532(12.5); 1.256(1.0); 1.228(1.0); 1.207(1.0); 1.060(0.8); 1.034(0.7);
0.970(7.2); 0.952(16.0); 0.934(6.9); 0.008(1.3); 0.000(42.4); −0.008(1.3)

Example I-098: ¹H-NMR(400.0 MHz, CDCl3):
δ = 7.560(1.6); 7.556(1.2); 7.549(5.5); 7.545(6.0); 7.537(10.0); 7.532(11.2); 7.526(1.7); 7.521(1.2); 7.519(1.2); 7.428(1.3); 7.422(6.0); 7.414(4.3); 7.412(4.5); 7.404(5.2); 7.399(4.2); 7.260(148.0); 7.221(2.0); 6.996(1.2); 6.986(16.0); 3.894(9.6); 3.867(4.0); 2.401(0.6); 2.382(0.6); 2.076(1.0); 2.043(2.5); 1.935(0.8); 1.926(0.9); 1.916(1.0); 1.907(1.3); 1.898(1.1); 1.888(0.9); 1.879(0.8); 1.737(4.5); 1.730(4.1); 1.718(3.1); 1.672(1.1); 1.545(5.2); 1.304(0.8); 1.284(1.5); 1.276(2.2); 1.264(4.2); 1.259(4.2); 1.241(3.5); 1.221(2.6); 1.201(2.5); 1.188(2.4); 1.169(1.6); 1.156(0.8); 1.150(1.0); 1.086(1.0); 1.057(2.1); 1.034(1.8); 1.027(1.8); 0.997(0.7); 0.952(5.5); 0.933(10.6); 0.915(5.2); 0.899(2.2); 0.882(6.3); 0.864(2.5); 0.008(2.0); 0.000(57.1); −0.008(1.8)

Example I-099: ¹H-NMR(400.0 MHz, d6-DMSO):
δ = 7.554(1.4); 7.547(1.9); 7.543(1.1); 7.532(6.4); 7.528(3.3); 7.525(2.8); 7.518(4.1); 7.514(9.7); 7.510(6.2); 7.506(4.2); 7.502(1.6); 7.495(3.4); 7.480(0.9); 7.475(1.2); 7.467(8.7); 7.462(7.4); 7.457(2.1); 7.452(2.6); 7.447(5.8); 7.444(4.4); 7.433(16.0); 5.449(5.8); 3.890(7.5); 3.872(7.5); 3.601 (0.5); 3.316(40.7); 2.674(0.8); 2.670(1.2); 2.665(0.8); 2.523(3.9); 2.518(5.8); 2.510(67.7); 2.505(144.8); 2.501 (199.8); 2.496(139.1); 2.492(62.5); 2.455(0.5); 2.450(0.6); 2.446(0.5); 2.332(0.9); 2.328(1.2); 2.323(0.8); 2.073(1.2); 1.852(0.7); 1.844(0.8); 1.833(0.9); 1.825(1.1); 1.816(1.0); 1.806(0.8); 1.797(0.7); 1.760(0.7); 1.684(1.9); 1.668(2.6); 1.662(2.6); 1.611(3.9); 1.583(2.6); 1.184(1.3); 1.155(4.2); 1.133(1.7); 1.109(0.6); 1.050(1.1); 1.020(2.2); 0.990(1.8); 0.968(0.6); 0.008(3.2); 0.000(107.7); −0.009(3.2)

Example I-100: ¹H-NMR(400.0 MHz, d6-DMSO):
δ = 7.652(0.7); 7.582(9.9); 7.577(3.6); 7.566(4.2); 7.561(16.0); 7.482(15.6); 7.477(4.1); 7.466(3.8); 7.461(10.0); 7.454(1.6); 7.444(15.3); 5.481(8.7); 4.038(1.4); 4.021(1.4); 3.882(7.3); 3.864(7.4); 3.309(54.3); 2.670(1.4); 2.523(4.4); 2.518(6.4); 2.510(86.0); 2.506(185.0); 2.505(257.5); 2.501(257.5); 2.496(181.0); 2.491(81.5); 2.327(1.4); 2.072(3.2); 1.988(6.4); 1.818(1.2); 1.662(2.8); 1.606(4.0); 1.571(3.0); 1.235(1.1); 1.193(2.4); 1.175(4.6); 1.157(5.4); 1.132(3.2); 1.016(2.4); 0.984(1.9); 0.008(2.1); 0.000(67.9); −0.008(2.0)

Example I-101: ¹H-NMR(400.0 MHz, CDCl3):
δ = 8.172(1.9); 7.589(0.9); 7.579(10.1); 7.572(9.3); 7.568(4.4); 7.563(8.2); 7.556(2.2); 7.519(0.9); 7.429(0.6); 7.426(0.8); 7.420(5.7); 7.413(5.5); 7.408(3.6); 7.405(5.6); 7.401(2.5); 7.399(2.5); 7.396(4.0); 7.260(153.2); 7.033(16.0); 6.996(1.6); 5.298(0.7); 3.908(9.4); 3.890(9.6); 1.937(1.0); 1.928(0.8); 1.917(0.8); 1.909(1.2); 1.900(0.9); 1.890(1.0); 1.881(0.7); 1.767(1.8); 1.760(1.8); 1.736(5.4); 1.703(3.4); 1.680(1.2); 1.542(2.4); 1.284(0.9); 1.256(6.8); 1.224(2.5); 1.205(2.7); 1.191(1.8); 1.159(0.7); 1.091(1.0); 1.062(2.1); 1.039(1.7); 1.011(0.6); 1.001(0.6); 0.880(1.0); 0.008(1.6); 0.000(57.9); −0.008(1.8)

Example I-102: ¹H-NMR(400.0 MHz, d6-DMSO):
δ = 10.415(1.5); 7.940(5.8); 4.038(0.7); 4.020(0.7); 3.868(3.0); 3.849(3.1); 3.309(67.0); 2.669(0.7); 2.549(0.6); 2.545(0.6); 2.523(2.0); 2.518(2.8); 2.509(37.4); 2.505(80.2); 2.500(111.4); 2.496(79.2); 2.491(36.2); 2.327(0.7); 2.086(16.0); 1.988(3.2); 1.663(1.0); 1.610(0.6); 1.572(1.1); 1.542(1.0); 1.247(1.1); 1.192(1.1); 1.175(2.2); 1.157(2.4); 1.133(1.2); 1.008(0.9); 0.979(0.7); 0.875(0.5); 0.858(1.7); 0.841(0.6); 0.000(13.0)

Example I-103: ¹H-NMR(400.0 MHz, d6-DMSO):
δ = 7.930(7.6); 6.561(3.2); 5.754(1.5); 4.402(16.0); 3.859(4.1); 3.841(4.2); 3.345(39.8); 3.318(17.6); 3.299(0.7); 3.294(0.6); 2.674(0.5); 2.670(0.8); 2.665(0.6); 2.523(2.2); 2.519(3.3); 2.510(47.0); 2.505(102.9); 2.501(145.0); 2.496(103.1); 2.492(47.2); 2.469(0.8); 2.464(0.7); 2.332(0.7); 2.328(1.0); 2.323(0.7); 1.796(0.5); 1.788(0.7); 1.778(0.6); 1.677(1.1); 1.661(1.5); 1.608(0.9); 1.553(1.4); 1.523(1.4); 1.172(0.7); 1.145(2.6); 1.125(1.7); 1.025(0.6); 0.995(1.2); 0.966(1.0); 0.008(1.4); 0.000(52.6); −0.008(1.7)

Example I-104: ¹H-NMR(400.0 MHz, d6-DMSO):
δ = 8.040(16.0); 7.858(1.1); 7.610(0.8); 7.602(0.8); 7.591 (4.9); 7.585(3.31; 7.581 (6.5); 7.572(1.6); 7.566(7.6); 7.558(1.8); 7.500(1.5); 7.496(1.4); 7.483(3.6); 7.481(3.4); 7.475(9.8); 7.472(9.1); 7.470(6.4); 7.464(13.5); 7.458(14.0); 7.449(1.4); 6.561(10.5); 5.753(3.8); 3.896(7.7); 3.878(7.8); 3.829(0.6); 3.811(0.6); 3.337(0.5); 3.309(130.6); 2.679(0.6); 2.674(1.3); 2.670(1.7); 2.665(1.3); 2.523(5.9); 2.518(8.4); 2.510(97.8); 2.505(206.9); 2.501 (285.4); 2.496(200.8); 2.492(91.3); 2.332(1.2); 2.328(1.7); 2.323(1.2); 1.850(0.8); 1.841(0.9); 1.831(1.1); 1.822(1.4); 1.813(1.2); 1.804(1.0); 1.794(0.9); 1.673(3.2); 1.618(1.9); 1.583(3.2); 1.553(3.1); 1.236(0.7); 1.187(1.6); 1.158(5.3); 1.139(3.8); 1.049(1.2); 1.019(2.6); 0.990(2.2); 0.966(0.8); 0.858(0.6); 0.000(13.8)

Example I-105: ¹H-NMR(400.0 MHz, CDCl3):
δ = 7.271(3.0); 7.260(22.4); 7.190(0.6); 5.298(1.2); 3.846(1.4); 3.828(1.5); 3.419(9.5); 1.730(1.8); 1.699(1.6); 1.674(0.6); 1.572(1.6); 1.212(0.6); 0.000(8.1)

Example I-106: ¹H-NMR(400.0 MHz, CDCl3):
δ = 7.262(17.6); 7.215(3.7); 5.552(1.1); 5.298(3.8); 3.834(2.9); 3.816(3.0); 2.375(3.7); 2.359(4.0); 1.956(0.8); 1.940(1.0); 1.923(0.8); 1.906(0.5); 1.721(0.8); 1.713(0.9); 1.677(0.9); 1.669(0.9); 1.206(0.7); 1.182(0.7); 1.066(16.0); 1.050(15.5); 1.011(0.5); 0.000(6.8)

Example I-107: ¹H-NMR(400.0 MHz, CDCl3):
δ = 8.647(1.1); 7.519(1.7); 7.309(0.5); 7.292(0.6); 7.260(289.3); 6.996(1.7); 6.869(6.4); 5.298(1.8); 3.867(4.0); 3.852(4.3); 3.192(1.8); 3.042(0.6); 2.750(1.8); 2.732(4.7); 2.713(5.0); 2.696(2.1); 1.811(1.8); 1.688(6.1); 1.656(7.4); 1.631(6.6); 1.328(0.9); 1.278(7.4); 1.259(16.0); 1.240(9.2); 1.220(4.4); 1.164(7.0); 1.003(3.5); 0.978(3.4); 0.882(2.5); 0.864(1.6); 0.008(3.0); 0.000(102.4); −0.008(4.2)

Example I-108: ¹H-NMR(400.0 MHz, CDCl3):
δ = 7.265(9.1); 6.866(2.4); 6.863(2.3); 6.764(1.0); 6.761(1.0); 6.739(0.5); 6.736(1.1); 6.733(1.0); 6.174(0.5); 6.157(1.1); 6.146(0.5); 6.140(0.6); 6.129(1.0); 6.112(0.5); 4.956(1.0); 4.014(2.6); 4.011(2.4); 3.997(2.6); 3.994(2.4); 3.846(3.0); 3.827(3.0); 3.385(1.4); 3.345(16.0); 1.755(0.6); 1.749(0.6); 1.723(1.8); 1.691(1.4); 1.686(1.4); 1.255(0.6); 1.247(0.5); 1.216(1.1); 1.198(0.9); 1.189(0.8); 1.046(0.7); 1.017(0.6); 0.000(3.5)

Example I-109: ¹H-NMR(400.0 MHz, CDCl3):
δ = 8.085(0.9); 8.081 (0.7); 7.260(82.7); 6.765(5.4); 6.761 (5.2); 6.503(0.9); 6.500(2.0); 6.496(1.9); 6.492(0.8); 6.476(1.0); 6.472(2.2); 6.468(2.1); 6.465(0.8); 6.037(1.1); 6.018(2.4); 6.010(1.1); 6.000(1.2); 5.991(2.1); 5.972(1.0); 5.036(2.0); 4.677(0.9); 3.842(7.1); 3.824(7.2); 2.153(1.2); 2.149(1.2); 2.135(3.0); 2.131(3.0); 2.116(3.1); 2.112(3.0); 2.097(1.4); 2.093(1.3); 1.909(0.6); 1.898(0.6); 1.890(0.8); 1.881(0.7); 1.871(0.6); 1.861(0.5); 1.748(1.4); 1.741(1.4); 1.718(4.0); 1.689(2.9); 1.573(1.4); 1.482(0.6); 1.464(2.1); 1.445(3.7); 1.426(3.8); 1.408(2.2); 1.390(0.6); 1.255(4.1); 1.212(2.3); 1.201(1.8); 1.196(1.8); 1.185(1.6); 1.154(0.5); 1.062(0.8); 1.035(1.6); 1.011(1.3); 1.004(1.3); 0.921(7.6); 0.903(16.0); 0.884(6.9); 0.008(1.8); 0.000(33.6); −0.008(1.1)

Example I-110: ¹H-NMR(400.0 MHz, CDCl3):
δ = 8.085(2.8); 8.081(2.5); 7.519(1.0); 7.260(158.1); 7.211(1.4); 6.996(1.0); 6.753(12.1); 4.840(4.3); 4.676(3.2); 3.823(13.9); 3.805(13.7); 2.713(5.2); 2.694(7.4); 2.675(5.4); 2.448(0.6); 1.915(0.6); 1.905(1.1); 1.896(1.3); 1.887(1.4); 1.877(1.8); 1.869(1.6); 1.859(1.3); 1.850(1.2); 1.737(3.2); 1.708(5.7); 1.675(8.9); 1.665(9.0); 1.644(4.4); 1.625(1.9); 1.575(2.9); 1.421(1.1); 1.404(4.0); 1.401(4.0); 1.394(6.4); 1.386(12.9); 1.377(9.4); 1.368(8.8); 1.254(6.2); 1.237(2.6); 1.222(2.9); 1.205(6.0); 1.182(4.3); 1.151(1.1); 1.083(1.1); 1.065(2.8); 1.038(3.7); 1.008(3.1); 0.986(1.5); 0.978(1.1); 0.940(6.2); 0.923(16.0); 0.905(5.2); 0.880(1.0); 0.862(0.5); 0.008(2.3); 0.000(67.0); −0.008(3.0)

Example I-111: ¹H-NMR(400.0 MHz, d6-DMSO): ¹H-NMR(400.0 MHz, d6-DMSO): δ = 7.74 (1H), 6.61 (2H), 3.77 (2H), 1.85-1.52 (5H), 1.24-0.97 (6H)

Example I-112: ¹H-NMR(400.0 MHz, d6-DMSO):
δ = 7.256(8.2); 7.197(14.1); 7.194(14.2); 6.468(15.8); 5.753(16.0); 4.039(1.0); 4.021(1.0); 3.798(15.0); 3.780(15.3); 3.312(180.8); 2.676(0.7); 2.671(1.1); 2.666(0.8); 2.524(2.6); 2.520(3.8); 2.511(58.3); 2.506(127.2); 2.502(177.8); 2.497(126.7); 2.493(58.0); 2.333(0.8); 2.329(1.1); 2.324(0.8); 2.125(0.8); 2.112(1.9); 2.108(2.0); 2.104(2.0); 2.095(3.4); 2.092(3.4); 2.082(2.2); 2.079(2.1); 2.075(2.0); 2.062(0.9); 1.989(4.4); 1.800(0.8); 1.790(1.4); 1.781(1.7); 1.772(2.0); 1.763(2.5); 1.754(2.1); 1.744(1.8); 1.735(1.7); 1.726(1.0); 1.716(0.8); 1.671(4.2); 1.655(5.1); 1.605(3.4); 1.534(4.7); 1.503(5.0); 1.241(1.8); 1.193(2.0); 1.175(4.0); 1.165(2.8); 1.158(3.8); 1.141(9.2); 1.122(5.6); 1.018(2.0); 0.990(4.0); 0.959(5.9); 0.948(9.4); 0.944(9.8); 0.939(5.5); 0.934(5.4); 0.928(9.2); 0.923(9.0); 0.913(3.4); 0.875(1.0); 0.858(2.8); 0.840(1.1); 0.687(3.4); 0.677(9.1); 0.673(10.3); 0.664(9.4); 0.660(9.3); 0.649(2.8); 0.436(0.8); 0.428(1.6); 0.422(2.4); 0.415(1.4); 0.405(1.8); 0.399(2.9); 0.392(1.3); 0.343(0.8); 0.337(1.9); 0.330(2.8); 0.322(2.7); 0.315(4.0); 0.309(2.1); 0.301(0.9); 0.156(0.8); 0.149(0.9); 0.142(1.0); 0.136(0.7); 0.008(1.2); 0.000(42.9); −0.008(1.3); −0.379(0.8); −0.387(0.8); −0.402(1.4); −0.417(0.7); −0.425(0.7); −0.490(0.6)

Example I-113: ¹H-NMR(400.0 MHz, d6-DMSO):
δ = 7.601(6.1); 6.466(4.5); 6.449(4.6); 6.269(5.3); 5.754(2.5); 5.621(3.2); 5.604(3.1); 3.980(2.2); 3.962(7.2); 3.945(7.2); 3.927(2.2); 3.840(4.9); 3.823(5.0); 3.312(26.2); 2.525(0.6); 2.520(0.9); 2.512(13.4); 2.507(29.5); 2.503(41.2); 2.498(29.3); 2.494(13.3); 2.471(0.6); 2.333(0.8); 1.724(0.7); 1.662(1.6); 1.619(2.2); 1.593(2.2); 1.249(7.6); 1.231(16.0); 1.213(7.4); 1.176(1.1); 1.155(3.0); 1.136(1.9); 1.043(0.7); 1.014(1.3); 0.986(1.1); 0.000(8.0)

Example I-114: ¹H-NMR(400.0 MHz, d6-DMSO):
δ = 10.387(1.4); 7.534(11.3); 7.401(1.4); 7.361(3.2); 7.226(7.3); 7.206(16.0); 7.138(3.0); 6.629(2.4); 6.601(2.3); 6.269(1.6); 6.205(7.7); 6.158(14.8); 6.128(2.9); 6.113(3.0); 6.099(1.8); 6.088(4.0); 6.070(3.8); 6.056(2.0); 6.044(3.6); 6.030(1.6); 6.005(2.4); 5.987(2.7); 5.977(3.0); 5.960(2.0); 5.754(0.9); 5.589(2.0); 5.494(2.1); 5.442(1.9); 5.417(1.1); 5.140(5.8); 5.135(5.5); 5.114(5.0); 5.110(5.1); 5.053(1.4); 5.031(5.9); 5.027(5.3); 4.988(5.8); 4.984(5.2); 3.861(7.5); 3.842(8.4); 3.812(15.6); 3.794(15.4); 3.549(8.9); 3.534(8.5); 3.311(246.2); 2.671(2.3); 2.524(8.5); 2.520(11.5); 2.511(142.0); 2.506(303.0); 2.502(416.8); 2.497(289.5);

2.493(129.0); 2.329(2.5); 2.081(4.6); 1.985(6.6); 1.866(1.9); 1.850(2.4);
1.776(3.6); 1.730(12.2); 1.725(14.6); 1.721(15.1); 1.717(10.1);
1.713(11.7); 1.708(11.6); 1.662(8.7); 1.606(5.7); 1.562(7.4); 1.533(7.1);
1.235(8.6); 1.148(15.4); 1.130(9.5); 0.997(5.9); 0.853(1.5); 0.008(2.9);
0.000(86.0)
Example I-115: $^1$H-NMR(400.0 MHz, $d_6$-DMSO):
δ = 7.784(4.6); 6.563(3.6); 3.838(3.2); 3.819(3.4); 3.311 (100.2);
2.670(0.6); 2.524(1.7); 2.519(2.4); 2.510(33.6); 2.506(73.8);
2.501(103.2); 2.496(72.8); 2.492(32.9); 2.328(0.6); 2.123(16.0);
1.988(1.2); 1.776(0.6); 1.659(1.2); 1.598(0.9); 1.546(1.2); 1.519(1.1);
1.298(0.5); 1.281(0.6); 1.244(1.6); 1.193(0.5); 1.175(1.1); 1.143(2.1);
1.123(1.4); 0.988(0.9); 0.958(0.8); 0.892(0.7); 0.874(2.0); 0.858(3.1);
0.841 (1.0); 0.008(1.0); 0.000(33.2); −0.008(0.9)
Example I-116: $^1$H-NMR(400.0 MHz, CDCl3):
δ = 7.682(0.6); 7.412(0.6); 7.396(1.8); 7.392(1.2); 7.377(1.9); 7.357(0.9);
7.354(0.8); 7.340(1.1); 7.330(2.0); 7.328(1.9); 7.326(1.8); 7.312(1.2);
7.260(79.4); 6.438(1.6); 3.448(2.4); 3.431(2.5); 2.600(0.7); 2.581(0.6);
1.541(16.0); 1.511(0.9); 1.502(1.0); 1.303(1.0); 1.295(3.5); 1.276(7.3);
1.264(4.0); 1.258(5.0); 1.244(0.9); 1.185(0.6); 1.166(0.9); 1.148(0.6);
1.027(0.7); 0.994(0.8); 0.958(0.7); 0.938(0.8); 0.899(2.2); 0.882(6.0);
0.864(2.5); 0.665(0.7); 0.634(0.6); 0.008(1.1); 0.000(28.4); −0.008(1.2)
Example I-117: $^1$H-NMR(400.0 MHz, CDCl3):
δ = 7.260(59.0); 6.754(2.9); 4.839(0.9); 3.825(3.2); 3.807(3.2); 2.698(1.1);
2.679(1.8); 2.660(1.2); 1.739(0.7); 1.709(1.6); 1.695(1.1); 1.676(2.1);
1.668(1.6); 1.664(1.5); 1.656(1.8); 1.647(1.0); 1.643(0.8); 1.636(1.2);
1.629(0.7); 1.622(0.7); 1.617(0.8); 1.605(1.0); 1.588(1.2); 1.572(1.0);
1.555(1.0); 1.313(1.0); 1.296(1.4); 1.284(1.0); 1.273(1.7); 1.256(3.3);
1.238(0.8); 1.206(1.3); 1.183(1.0); 1.040(0.8); 1.010(0.7); 0.979(0.6);
0.914(1.6); 0.910(16.0); 0.898(1.8); 0.894(15.4); 0.880(0.7); 0.873(0.5);
0.008(0.6); 0.000(22.5); −0.008(0.7)
Example I-118: $^1$H-NMR(400.0 MHz, $d_6$-DMSO):
δ = 7.404(1.6); 7.226(10.2); 7.224(10.1); 6.629(3.1); 6.605(2.8);
6.601(3.4); 6.268(1.7); 6.205(11.5); 6.022(1.1); 6.005(4.1); 5.994(1.2);
5.987(4.0); 5.977(4.3); 5.960(4.2); 5.943(1.2); 5.923(0.7); 5.754(5.1);
3.861(11.1); 3.842(11.4); 3.309(80.5); 2.671(1.0); 2.524(2.6); 2.520(3.8);
2.511(61.0); 2.506(132.6); 2.502(185.1); 2.497(130.6); 2.493(59.2);
2.329(1.0); 1.989(1.4); 1.871(2.1); 1.866(2.0); 1.854(2.2); 1.850(2.2);
1.820(1.4); 1.801(2.0); 1.792(1.7); 1.774(1.4); 1.730(16.0); 1.726(15.6);
1.713(15.8); 1.708(16.0); 1.662(4.2); 1.573(4.1); 1.542(4.0); 1.236(0.9);
1.176(2.9); 1.151(7.6); 1.131(4.9); 1.013(3.3); 0.983(2.7); 0.008(2.7);
0.000(90.0); −0.009(2.5)
Example I-119: $^1$H-NMR(400.0 MHz, $d_6$-DMSO):
δ = 7.859(0.8); 7.258(16.0); 6.015(9.9); 5.795(4.1); 5.753(3.0); 3.824(8.8);
3.806(8.8); 3.359(2.1); 3.310(319.7); 2.890(0.6); 2.675(1.3); 2.670(1.9);
2.666(1.3); 2.555(1.1); 2.550(1.9); 2.545(2.0); 2.540(1.8); 2.523(6.5);
2.519(9.1); 2.510(104.6); 2.506(222.8); 2.501(307.9); 2.496(217.8);
2.492(98.5); 2.337(0.6); 2.332(1.3); 2.328(1.8); 2.323(1.2); 2.202(5.0);
2.187(5.3); 2.171(3.7); 1.802(0.9); 1.793(1.1); 1.783(1.3); 1.774(1.8);
1.765(2.1); 1.751(3.0); 1.737(4.1); 1.723(3.7); 1.658(4.8); 1.650(6.1);
1.635(4.3); 1.620(3.0); 1.607(2.7); 1.565(3.3); 1.533(3.3); 1.354(1.8);
1.169(1.8); 1.145(6.1); 1.126(3.8); 1.030(1.3); 1.000(2.6); 0.971(2.1);
0.008(1.7); 0.000(53.5); −0.008(1.5)
Example I-120: $^1$H-NMR(400.0 MHz, $d_6$-DMSO):
δ = 7.402(12.7); 7.361(3.3); 6.821(3.6); 6.782(3.9); 6.267(13.2);
6.130(2.1); 5.976(4.6); 5.960(5.1); 5.938(4.8); 5.922(4.5); 3.848(12.1);
3.830(12.4); 3.309(323.9); 2.670(3.2); 2.523(9.9); 2.518(14.1);
2.510(194.1); 2.505(423.3); 2.501(590.4); 2.496(417.4); 2.492(188.0);
2.327(2.9); 2.079(4.8); 1.988(2.8); 1.870(16.0); 1.866(16.0); 1.853(15.6);
1.849(15.8); 1.794(2.5); 1.660(5.0); 1.564(4.6); 1.536(4.5); 1.248(4.6);
1.175(4.3); 1.148(8.7); 1.128(5.4); 1.008(3.8); 0.982(3.4); 0.858(8.0);
0.841(2.8); 0.008(5.6); 0.000(195.8); −0.009(5.9)
Example I-121: $^1$H-NMR(400.0 MHz, $d_6$-DMSO):
δ = 7.796(16.0); 7.490(0.7); 6.598(9.9); 3.847(9.3); 3.828(9.4);
3.312(110.3); 2.671(1.1); 2.528(15.0); 2.520(5.2); 2.511(81.3);
2.506(147.0); 2.502(203.8); 2.497(143.0); 2.493(64.6); 2.328(1.2);
2.138(1.0); 2.119(2.5); 2.101(3.5); 2.082(2.7); 2.063(1.1); 1.989(0.7);
1.826(2.6); 1.812(3.6); 1.794(4.2); 1.781(3.7); 1.651(5.2); 1.644(4.4);
1.631(4.6); 1.613(4.9); 1.590(3.0); 1.576(2.2); 1.550(6.0); 1.543(5.7);
1.534(5.1); 1.521(5.9); 1.437(0.6); 1.328(1.3); 1.312(3.1); 1.292(3.3);
1.280(3.3); 1.262(2.8); 1.244(2.6); 1.170(1.9); 1.143(6.3); 1.123(4.0);
0.992(2.9); 0.962(2.3); 0.858(2.8); 0.841(1.0); 0.008(1.8); 0.000(58.6);
−0.008(1.7)
Example I-122: $^1$H-NMR(400.0 MHz, $d_6$-DMSO):
δ = 7.799(16.0); 7.489(1.0); 6.588(12.0); 3.847(10.0); 3.829(10.1);
3.311(196.6); 2.671(1.3); 2.524(3.6); 2.520(5.3); 2.511(78.6);
2.506(172.9); 2.502(242.1); 2.497(171.0); 2.493(76.9); 2.434(14.0);
2.417(14.6); 2.329(1.2); 1.826(3.9); 1.792(4.7); 1.715(3.6); 1.683(6.3);
1.651(5.0); 1.606(3.8); 1.546(4.8); 1.519(4.9); 1.291(1.1); 1.260(3.4);
1.235(3.0); 1.228(4.6); 1.197(2.7); 1.177(3.2); 1.171(3.0); 1.147(8.2);
1.124(5.1); 1.090(2.5); 1.052(4.0); 1.022(4.6); 0.992(4.0); 0.963(2.5);
0.858(0.9); 0.000(31.4)
Example I-123: $^1$H-NMR(400.0 MHz, CDCl3):
δ = 7.518(1.2); 7.396(1.0); 7.382(18.7); 7.375(7.6); 7.369(7.4); 7.367(7.9);
7.361(1.2); 7.353(0.9); 7.347(1.3); 7.314(1.4); 7.308(1.7); 7.301(1.6);
7.298(1.5); 7.293(2.1); 7.284(1.5); 7.279(1.5); 7.259(221.9); 7.190(1.1);
6.995(1.2); 5.369(2.0); 3.872(16.0); 3.837(8.0); 3.819(8.1); 3.806(0.8);
1.895(0.6); 1.885(0.8); 1.876(0.8); 1.866(1.1); 1.858(0.9); 1.848(0.8);
1.838(0.7); 1.752(1.5); 1.721(2.4); 1.698(2.4); 1.668(2.9); 1.559(3.6);
1.257(1.1); 1.238(1.3); 1.206(2.9); 1.182(2.1); 1.150(5.0); 1.069(0.9);
1.038(2.0); 1.008(1.6); 0.977(0.5); 0.882(1.4); 0.864(0.6); 0.008(2.7);
0.000(83.4); −0.008(2.8)
Example I-124: $^1$H-NMR(400.0 MHz, $d_6$-DMSO):
δ = 7.777(4.8); 7.769(6.1); 7.764(6.1); 7.757(6.3); 7.680(6.4); 7.677(6.4);
7.673(5.9); 7.670(4.9); 7.465(16.0); 7.265(5.9); 7.262(5.7); 7.253(5.6);
7.250(5.3); 5.753(4.3); 5.580(9.1); 3.875(8.3); 3.856(8.5); 3.308(336.8);
2.890(2.1); 2.732(2.1); 2.669(3.5); 2.523(9.4); 2.518(14.0); 2.510(201.8);
2.505(437.9); 2.500(609.5); 2.496(427.5); 2.491(191.5); 2.327(3.1);
1.660(3.2); 1.598(4.2); 1.567(3.3); 1.236(3.6); 1.153(5.4); 1.132(3.9);
1.020(2.6); 0.008(5.4); 0.000(205.2); −0.008(5.6)
Example I-125: $^1$H-NMR(400.0 MHz, $d_6$-DMSO):
δ = 7.900(7.3); 7.898(7.9); 7.895(7.6); 7.893(6.4); 7.721(16.0); 6.702(4.7);
6.700(4.6); 6.694(10.2); 6.691(8.7); 6.682(9.3); 6.677(8.5); 6.674(4.2);
6.669(4.1); 5.969(10.1); 3.897(9.3); 3.879(9.5); 3.310(232.9); 3.258(1.4);
2.670(2.6); 2.551(0.8); 2.523(6.6); 2.518(9.2); 2.510(145.2); 2.505(306.4);
2.501(414.6); 2.496(296.0); 2.492(139.3); 2.327(2.4); 2.323(1.8);
1.988(1.8); 1.820(1.6); 1.666(3.5); 1.584(4.1); 1.556(3.5); 1.175(2.5);
1.153(5.8); 1.134(4.2); 1.020(2.8); 0.987(2.2); 0.008(3.6); 0.000(126.3);
−0.008(4.9)
Example I-126: $^1$H-NMR(400.0 MHz, CDCl3):
δ = 7.520(0.6); 7.261(114.2); 6.997(0.7); 6.911(2.3); 6.908(2.3);
6.872(0.8); 6.791(6.3); 6.592(0.6); 6.589(0.6); 6.585(0.5); 6.554(0.6);
6.551(0.7); 6.546(0.6); 6.014(1.0); 5.998(1.0); 5.976(0.9); 5.959(0.9);
5.299(2.2); 3.944(0.6); 3.852(3.2); 3.838(7.7); 3.834(4.2); 3.819(7.4);
2.706(2.4); 2.689(3.8); 2.669(2.7); 2.142(0.9); 1.938(3.4); 1.933(3.6);
1.921(3.5); 1.917(3.7); 1.905(0.7); 1.896(0.8); 1.886(0.8); 1.878(1.1);
1.869(0.9); 1.859(0.8); 1.849(0.7); 1.751(1.9); 1.733(3.5); 1.714(6.2);
1.695(5.7); 1.676(4.8); 1.392(2.9); 1.332(0.6); 1.285(1.0); 1.256(4.3);
1.237(1.5); 1.206(3.4); 1.182(2.6); 1.152(0.7); 1.069(1.0); 1.052(8.3);
1.034(16.0); 1.016(8.0); 0.987(0.6); 0.880(0.8); 0.008(1.1); 0.000(40.9);
−0.008(1.3)
Example I-127: $^1$H-NMR(400.0 MHz, CDCl3):
δ = 8.783(2.3); 7.519(1.9); 7.260(353.5); 7.213(2.9); 7.125(12.1);
7.110(12.1); 6.996(2.0); 5.298(1.5); 3.861(1.7); 3.836(15.3); 3.818(15.5);
2.354(0.8); 2.336(0.5); 1.882(1.2); 1.872(1.4); 1.862(1.6); 1.853(2.0);
1.844(1.7); 1.835(1.4); 1.826(1.3); 1.760(2.8); 1.735(4.4); 1.703(5.7);
1.674(5.4); 1.542(16.0); 1.256(11.6); 1.215(6.2); 1.192(4.5); 1.162(1.1);
1.084(1.8); 1.054(3.9); 1.025(3.1); 0.993(1.0); 0.897(0.8); 0.880(1.7);
0.862(0.8); 0.008(4.0); 0.000(134.5); −0.008(3.8)
Example I-128: $^1$H-NMR(400.0 MHz, CDCl3):
δ = 8.020(0.6); 7.519(0.6); 7.260(107.3); 7.242(3.2); 7.069(2.8);
7.054(2.9); 6.996(0.6); 3.819(3.5); 3.800(3.7); 2.710(0.6); 1.754(0.7);
1.730(1.0); 1.704(1.1); 1.676(1.3); 1.539(16.0); 1.522(0.7); 1.292(4.4);
1.273(9.4); 1.254(5.0); 1.212(1.4); 1.189(1.1); 1.049(0.9); 1.020(0.7);
0.899(0.6); 0.882(2.0); 0.864(0.8); 0.008(1.2); 0.000(39.5); −0.008(1.6);
−0.019(1.1)
Example I-129: $^1$H-NMR(400.0 MHz, $d_6$-DMSO):
δ = 7.898(6.3); 7.896(7.6); 7.894(8.2); 7.892(6.7); 7.866(7.1); 7.862(10.7);
7.858(5.4); 7.438(16.0); 6.740(7.4); 6.738(7.7); 6.736(7.5); 6.733(6.4);
5.785(9.9); 4.038(1.3); 4.020(1.2); 3.863(8.5); 3.845(8.6); 3.358(1.4);
3.308(209.7); 3.277(0.6); 3.259(0.8); 3.257(0.9); 2.674(1.6); 2.670(2.2);
2.665(1.4); 2.555(1.4); 2.551(1.5); 2.523(8.7); 2.518(12.9); 2.510(131.5);
2.505(273.4); 2.500(370.0); 2.496(263.0); 2.491(122.4); 2.457(2.4);
2.332(1.7); 2.327(2.2); 2.323(1.7); 1.988(5.5); 1.825(1.0); 1.816(1.1);
1.806(1.5); 1.798(1.2); 1.789(1.0); 1.780(0.9); 1.663(3.2); 1.587(3.7);
1.558(3.2); 1.236(1.8); 1.192(2.2); 1.175(4.6); 1.157(5.6); 1.151(5.6);
1.131(3.8); 1.043(1.2); 1.013(2.6); 0.984(2.1); 0.858(1.1); 0.008(4.0);
0.000(116.5); −0.008(4.1)
Example I-130: $^1$H-NMR(400.0 MHz, $d_6$-DMSO):
δ = 8.513(16.0); 7.323(1.6); 4.039(0.6); 4.021 (0.6); 3.976(9.9);
3.958(9.9); 3.378(1.2); 2.671 (0.7); 2.593(59.0); 2.525(1.7); 2.520(2.5);
2.511(40.0); 2.507(88.2); 2.502(123.4); 2.498(86.2); 2.493(38.4);
2.329(0.7); 1.989(2.4); 1.910(1.0); 1.876(0.9); 1.867(1.1); 1.857(1.2);
1.848(1.5); 1.840(1.3); 1.829(1.0); 1.678(3.1); 1.623(1.9); 1.588(3.3);
1.560(3.1); 1.356(2.9); 1.232(0.6); 1.193(2.2); 1.175(3.1); 1.166(5.6);
1.145(3.8); 1.074(1.3); 1.046(2.5); 1.016(2.0); 0.996(0.7); 0.892(0.6);
0.875(1.0); 0.008(1.6); 0.000(58.5); −0.009(1.5)

Example I-131: ¹H-NMR(400.0 MHz, d₆-DMSO):
δ = 7.859(1.2); 7.744(5.5); 7.741(5.7); 7.731(5.8); 7.728(5.5); 7.602(16.0); 7.262(4.3); 7.259(4.7); 7.253(7.3); 7.250(6.4); 7.229(7.2); 7.221(4.4); 7.216(6.5); 7.208(4.4); 6.551(0.6); 5.638(8.8); 3.886(7.8); 3.868(7.9); 3.830(0.7); 3.811(0.7); 3.360(1.2); 3.346(1.6); 3.340(1.6); 3.337(1.2); 3.310(666.9); 3.286(1.8); 3.279(1.3); 3.260(0.7); 2.674(2.2); 2.670(3.1); 2.665(2.2); 2.550(1.1); 2.545(1.5); 2.540(1.8); 2.535(2.2); 2.530(2.6); 2.523(9.1); 2.518(13.5); 2.510(175.8); 2.505(376.5); 2.501(520.8); 2.496(367.4); 2.491(168.7); 2.469(1.1); 2.450(0.8); 2.332(2.3); 2.327(3.1); 2.323(2.2); 1.988(1.8); 1.804(1.3); 1.666(3.0); 1.595(3.8); 1.559(3.0); 1.236(1.3); 1.175(2.4); 1.152(4.9); 1.130(3.7); 1.042(1.1); 1.013(2.4); 0.985(2.0); 0.893(0.5); 0.874(0.8); 0.008(1.0); 0.000(31.7); −0.008(1.0)
Example I-132: ¹H-NMR(400.0 MHz, d₆-DMSO):
δ = 7.661(16.0); 6.558(7.3); 6.550(7.5); 6.278(4.8); 6.275(4.8); 6.270(4.5); 6.267(4.3); 5.971(9.8); 3.888(8.0); 3.870(7.9); 3.314(422.9); 2.670(1.7); 2.524(5.0); 2.510(103.4); 2.506(225.4); 2.501(315.0); 2.496(223.7); 2.492(101.9); 2.352(27.5); 2.328(1.8); 2.073(3.6); 1.814(1.5); 1.657(2.9); 1.575(3.0); 1.546(2.8); 1.152(5.0); 1.129(3.6); 1.013(2.4); 0.984(2.1); 0.000(39.1)
Example I-133: ¹H-NMR(400.0 MHz, d₆-DMSO):
δ = 7.562(12.1); 6.211(7.5); 4.495(4.5); 4.489(5.0); 4.407(5.7); 4.402(5.2); 3.982(2.1); 3.964(6.6); 3.947(6.5); 3.929(2.0); 3.863(6.2); 3.845(6.5); 3.312(184.1); 2.670(1.1); 2.523(2.6); 2.510(63.2); 2.506(137.7); 2.501(192.4); 2.496(136.2); 2.492(61.6); 2.328(1.0); 1.786(1.1); 1.661(2.4); 1.607(1.5); 1.567(2.5); 1.537(2.2); 1.326(7.3); 1.308(16.0); 1.291(7.0); 1.235(0.8); 1.175(1.5); 1.149(4.1); 1.131(2.9); 1.008(1.8); 0.980(1.6); 0.858(0.8); 0.008(1.8); 0.000(61.3); −0.008(1.8)
Example I-134: ¹H-NMR(400.0 MHz, CDCl3):
δ = 7.261(20.1); 7.130(4.6); 5.299(2.1); 4.013(16.0); 3.874(2.8); 3.856(2.8); 2.268(15.4); 1.717(1.1); 1.685(0.9); 1.677(0.8); 1.258(0.7); 1.255(0.6); 1.210(0.8); 1.190(0.6); 1.184(0.6); 1.047(0.5); 0.000(7.7)
Example I-135: ¹H-NMR(400.0 MHz, CDCl3):
δ = 7.611(16.0); 7.519(0.7); 7.260(118.6); 6.996(0.7); 5.299(1.4); 5.283(3.5); 3.891(9.6); 3.873(9.7); 1.883(0.7); 1.874(0.8); 1.864(0.9); 1.855(1.2); 1.846(0.8); 1.836(0.8); 1.827(0.7); 1.776(1.5); 1.744(2.2); 1.689(2.7); 1.662(2.2); 1.578(1.2); 1.284(0.8); 1.254(2.9); 1.218(2.9); 1.196(2.2); 1.163(0.6); 1.072(0.8); 1.042(1.9); 1.012(1.6); 0.008(1.3); 0.000(43.3); −0.008(1.3)
Example I-136: ¹H-NMR(400.0 MHz, CDCl3):
δ = 7.518(3.8); 7.434(1.8); 7.412(2.3); 7.392(2.3); 7.371(2.1); 7.310(1.1); 7.260(665.7); 7.240(13.6); 7.237(13.3); 7.015(2.1); 6.999(2.5); 6.995(4.3); 6.991(3.9); 6.975(3.8); 6.967(2.1); 6.952(2.1); 5.373(4.7); 5.126(16.0); 1.581(8.8); 1.284(2.8); 1.255(12.7); 0.880(2.1); 0.008(8.6); 0.000(233.7); −0.008(6.6); −0.150(0.8)
Example I-137: ¹H-NMR(400.0 MHz, d₆-DMSO): δ = 7.64 (1H), 6.67 (1H), 4.45 (1H), 4.11-4.03 (1H), 3.92-3.85 (1H), 2.35-2.25 (1H), 1.98-1.42 (6H), 1.37 (18H), 1.28-1.18 (2H)
Example I-138: ¹H-NMR(400.0 MHz, d₆-DMSO):
δ = 6.520(1.6); 5.606(0.8); 3.950(0.5); 3.844(0.6); 3.311(40.2); 2.505(28.0); 2.500(39.7); 2.496(31.8); 1.656(0.9); 1.625(0.9); 1.592(0.6); 1.455(0.6); 1.434(16.0); 1.419(1.2); 1.240(0.6); 1.153(0.8); 1.131(0.6); 0.858(0.6); 0.000(1.8)
Example I-139: ¹H-NMR(400.0 MHz, d₆-DMSO):
δ = 9.210(1.1); 8.153(3.1); 7.844(1.7); 7.842(1.7); 7.826(1.3); 7.814(1.3); 7.807(0.8); 7.336(1.4); 7.324(1.1); 6.871(1.6); 6.629(0.8); 5.727(1.1); 3.917(2.1); 3.899(2.2); 3.319(81.3); 2.670(0.5); 2.501(85.3); 2.327(0.5); 2.183(2.4); 1.988(0.9); 1.670(1.1); 1.595(1.2); 1.564(1.0); 1.356(16.0); 1.237(1.0); 1.192(0.8); 1.174(1.0); 1.158(1.6); 1.138(1.2); 1.004(0.9); 0.976(0.7); 0.000(2.0)
Example I-140: ¹H-NMR(400.0 MHz, d₆-DMSO):
δ = 9.255(0.8); 8.258(3.9); 7.826(1.4); 7.823(1.5); 7.813(1.5); 7.810(1.4); 7.427(1.4); 7.424(1.4); 7.418(1.6); 7.415(1.4); 7.240(1.5); 7.231(1.4); 7.227(1.5); 7.218(1.3); 6.870(1.2); 6.628(0.7); 5.829(0.8); 4.038(0.8); 4.020(0.8); 3.920(1.8); 3.902(1.8); 3.312(61.4); 2.669(0.7); 2.523(2.2); 2.518(3.2); 2.509(37.2); 2.505(78.9); 2.500(108.5); 2.496(76.3); 2.491(34.7); 2.327(0.6); 2.183(1.9); 1.988(3.4); 1.691(0.5); 1.668(0.7); 1.593(0.8); 1.559(0.7); 1.355(16.0); 1.236(0.6); 1.192(1.3); 1.174(2.2); 1.157(1.9); 1.135(0.8); 1.000(0.6); 0.970(0.5); 0.008(2.0); 0.000(61.6); −0.008(1.8)
Example I-141: ¹H-NMR(400.0 MHz, CDCl3):
δ = 7.260(33.2); 7.130(4.7); 4.272(1.2); 4.254(3.7); 4.236(3.8); 4.219(1.2); 3.874(2.8); 3.856(2.8); 2.277(16.0); 1.748(0.6); 1.721(1.5); 1.688(1.2); 1.684(1.2); 1.364(4.0); 1.347(8.3); 1.329(3.9); 1.241(0.5); 1.210(1.0); 1.186(0.8); 1.048(0.7); 1.019(0.6); 0.000(13.0); −0.008(0.6)
Example Example I-142: ¹H-NMR(400.0 MHz, CDCl3):
δ = 7.820(0.5); 7.518(1.4); 7.260(235.0); 7.253(0.9); 7.252(0.7); 7.251(0.6); 6.996(1.6); 6.848(6.3); 5.298(1.4); 4.800(1.2); 4.120(1.4); 4.102(4.5); 4.085(4.5); 4.067(1.4); 2.574(1.4); 2.284(0.9); 2.275(0.6); 2.239(16.0); 2.227(0.7); 2.043(1.2); 1.880(0.5); 1.751(0.8); 1.721(2.2); 1.690(1.6); 1.538(10.7); 1.304(0.7); 1.284(1.2); 1.276(1.6); 1.256(6.5); 1.241(1.1); 1.232(0.8); 1.214(1.6); 1.203(6.5); 1.186(12.6); 1.168(5.6); 1.061(0.5); 1.033(0.9); 1.009(0.8); 0.899(1.1); 0.882(3.3); 0.864(1.4); 0.008(2.7); 0.000(91.0); −0.008(2.6)
Example I-143: ¹H-NMR(400.0 MHz, CDCl3):
δ = 7.520(0.6); 7.261 (98.9); 6.997(0.5); 6.801(9.8); 6.177(0.8); 6.164(1.8); 6.151 (1.7); 6.138(2.1); 6.134(1.0); 6.126(1.0); 6.121 (2.1); 6.108(1.9); 6.095(2.1); 6.082(1.0); 5.298(1.2); 5.293(2.9); 5.290(2.9); 5.285(1.2); 5.272(1.1); 5.267(2.7); 5.264(2.8); 5.259(1.2); 5.120(1.2); 5.115(2.8); 5.112(2.7); 5.107(1.2); 5.077(1.1); 5.072(2.6); 5.069(2.5); 5.064(1.1); 4.870(4.7); 3.832(11.5); 3.814(11.6); 3.513(4.8); 3.512(5.0); 3.506(4.1); 3.500(4.9); 3.499(4.8); 2.575(1.4); 2.170(0.5); 1.914(0.8); 1.904(0.9); 1.894(1.0); 1.885(1.3); 1.876(1.1); 1.866(0.9); 1.858(0.8); 1.747(2.0); 1.709(4.3); 1.677(3.7); 1.667(3.7); 1.645(1.2); 1.626(0.7); 1.574(16.0); 1.387(0.6); 1.369(1.0); 1.350(1.0); 1.332(0.7); 1.318(0.6); 1.297(0.7); 1.278(0.9); 1.256(1.3); 1.247(1.3); 1.240(1.7); 1.209(3.5); 1.189(2.5); 1.183(2.4); 1.151(0.7); 1.069(1.2); 1.040(2.4); 1.010(1.9); 0.986(0.6); 0.979(0.7); 0.941(2.2); 0.923(4.5); 0.904(1.9); 0.008(1.0); 0.000(33.5); −0.008(1.0)
Example I-144: ¹H-NMR(400.0 MHz, d₆-DMSO):
δ = 6.29 (2H), 5.56 (1H), 4.69 (1H), 3.77-3.73 (1H), 3.55-3.51 (1H), 3.39-3.30 (1H), 3.20-3.15 (1H), 1-68-1.62 (5H), 1.24-0.85 (6H)
Example I-145: ¹H-NMR(400.0 MHz, d₆-DMSO):
δ = 7.595(8.0); 7.586(7.9); 6.244(8.3); 6.236(8.1); 6.156(0.9); 6.141(2.7); 6.125(2.6); 6.108(0.8); 6.039(0.8); 6.023(2.6); 6.007(2.7); 5.991(0.8); 5.753(3.7); 3.902(1.6); 3.884(1.7); 3.870(5.8); 3.852(11.3); 3.834(5.9); 3.820(1.6); 3.802(1.8); 3.363(1.0); 3.314(256.2); 2.676(0.7); 2.671(1.0); 2.666(0.7); 2.552(0.6); 2.547(0.6); 2.524(3.2); 2.520(4.7); 2.511(58.5); 2.507(126.0); 2.502(175.1); 2.498(124.6); 2.493(57.3); 2.333(0.8); 2.329(1.0); 2.324(0.8); 2.086(3.3); 1.989(0.8); 1.829(0.7); 1.820(1.2); 1.810(1.5); 1.801(1.7); 1.792(2.2); 1.783(1.8); 1.773(1.6); 1.764(1.5); 1.755(0.9); 1.734(12.1); 1.718(12.4); 1.676(16.0); 1.660(15.8); 1.611(2.9); 1.561(4.2); 1.533(4.3); 1.485(0.6); 1.468(0.6); 1.235(6.5); 1.208(0.7); 1.176(2.8); 1.154(8.5); 1.134(5.3); 1.041(1.7); 1.012(3.6); 0.982(2.9); 0.960(1.0); 0.858(0.7); 0.854(1.0); 0.008(0.7); 0.000(22.0); −0.008(0.7)
Example I-146: ¹H-NMR(400.0 MHz, d₆-DMSO):
δ = 8.014(3.4); 8.012(3.0); 7.898(3.2); 7.897(3.5); 7.894(2.9); 7.546(4.4); 5.755(5.6); 5.753(8.3); 5.752(7.3); 5.617(1.6); 3.871(3.3); 3.855(16.0); 3.370(0.7); 3.322(12.1); 2.501(43.5); 1.988(1.4); 1.911(2.7); 1.909(4.3); 1.908(3.9); 1.820(0.6); 1.666(1.5); 1.598(2.0); 1.567(1.6); 1.356(1.9); 1.235(1.2); 1.192(0.6); 1.175(1.5); 1.156(2.5); 1.152(2.5); 1.132(1.8); 1.043(0.6); 1.014(1.2); 0.986(1.0); 0.002(2.3); 0.000(3.6); −0.001(3.3)
Example I-147: ¹H-NMR(400.0 MHz, d₆-DMSO):
δ = 7.402(11.1); 7.056(9.9); 6.260(6.5); 6.251(6.4); 4.861(0.6); 4.845(2.0); 4.835(2.0); 4.828(2.0); 4.819(2.0); 4.802(0.5); 4.056(1.2); 4.038(3.6); 4.021(3.6); 4.003(1.2); 3.893(1.9); 3.874(2.0); 3.861(2.8); 3.842(2.8); 3.757(2.8); 3.739(2.9); 3.725(1.9); 3.707(1.9); 3.359(1.9); 3.309(182.9); 3.258(0.9); 3.243(0.7); 2.679(0.6); 2.674(1.2); 2.670(1.7); 2.665(1.2); 2.560(0.8); 2.556(1.3); 2.551(1.6); 2.546(1.0); 2.542(0.7); 2.523(5.2); 2.518(7.0); 2.510(92.8); 2.505(201.9); 2.501(282.4); 2.496(200.2); 2.491(91.5); 2.471(0.5); 2.466(0.6); 2.461(0.6); 2.456(0.6); 2.336(0.5); 2.332(1.2); 2.327(1.7); 2.323(1.2); 2.318(0.6); 1.988(16.0); 1.801(0.7); 1.793(0.9); 1.783(1.0); 1.774(1.3); 1.765(1.1); 1.755(1.0); 1.746(0.9); 1.666(2.8); 1.612(1.8); 1.581(1.7); 1.558(2.5); 1.456(14.7); 1.439(14.6); 1.236(0.9); 1.192(4.8); 1.175(10.3); 1.157(7.4); 1.150(4.7); 1.136(3.0); 1.040(1.0); 1.011(2.1); 0.981(1.8); 0.050(0.8); 0.008(3.4); 0.000(120.3); −0.008(3.8)
Example I-148: ¹H-NMR(400.0 MHz, d₆-DMSO):
δ = 13.275(0.6); 7.956(11.4); 7.952(11.6); 7.806(12.2); 7.802(11.5); 7.539(16.0); 5.618(3.7); 3.872(8.2); 3.854(8.3); 3.329(133.4); 2.674(2.0); 2.670(2.8); 2.665(2.2); 2.554(1.1); 2.550(1.7); 2.545(1.8); 2.540(1.7); 2.536(1.5); 2.523(8.9); 2.518(13.7); 2.510(166.0); 2.505(347.5); 2.501(477.5); 2.496(342.9); 2.492(162.1); 2.332(2.1); 2.327(2.8); 2.323(2.0); 1.988(1.1); 1.908(1.4); 1.819(1.6); 1.665(3.7); 1.597(4.8); 1.569(3.8); 1.236(1.5); 1.175(2.3); 1.152(6.1); 1.132(4.3); 1.042(1.5); 1.014(3.0); 0.985(2.5); 0.008(1.3); 0.000(38.0); −0.008(1.4)
Example I-149: ¹H-NMR(400.0 MHz, d₆-DMSO):
δ = 11.534(6.8); 8.462(9.3); 5.753(8.3); 4.021(0.5); 3.975(8.4); 3.957(8.4); 3.308(188.1); 3.258(0.7); 2.674(1.6); 2.670(2.2); 2.665(1.5); 2.560(45.0); 2.523(5.8); 2.518(9.1); 2.510(132.3); 2.505(283.4); 2.501(390.2); 2.496(274.6); 2.491(123.9); 2.450(1.4); 2.446(1.3); 2.332(1.8); 2.327(2.4); 2.323(1.7); 2.269(1.2); 2.106(1.2); 2.072(1.9); 2.035(0.8); 1.988(2.5); 1.874(1.0); 1.865(1.1); 1.857(1.4); 1.847(1.2); 1.837(1.0); 1.680(3.2); 1.661(2.4); 1.625(2.0); 1.596(3.4); 1.565(3.0); 1.258(0.9); 1.236(2.8); 1.192(2.2); 1.174(4.7); 1.168(5.5); 1.157(3.0); 1.148(3.8); 1.125(1.3); 1.080(1.3); 1.051 (2.6); 1.023(2.1); 0.854(0.7); 0.146(0.8); 0.008(7.1); 0.000(244.3); −0.008(7.2); −0.050(0.6); −0.149(0.9)

-continued

Example I-150: ¹H-NMR(400.0 MHz, d₆-DMSO):
¹H-NMR(400.0 MHz, d₆-DMSO): δ = 8.02 (2H), 7.84 (1H), 7.51 (2H), 5.61 (2H), 3.87 (2H), 1.85-1.56 (6H), 1.23-0.99 (5H)
Example I-151: ¹H-NMR(400.0 MHz, CDCl3):
δ = 8.314(16.0); 7.518(2.5); 7.492(3.7); 7.488(1.6); 7.474(6.7); 7.472(6.3); 7.458(2.3); 7.453(5.8); 7.351(3.2); 7.348(2.0); 7.332(4.4); 7.313(2.0); 7.310(1.5); 7.288(0.7); 7.260(396.4); 7.212(6.1); 7.209(8.2); 7.204(2.0); 7.193(3.6); 7.190(6.1); 7.188(5.5); 6.995(2.3); 6.454(0.9); 3.962(9.0); 3.944(9.0); 1.923(1.2); 1.905(0.8); 1.785(2.0); 1.751(4.6); 1.714(3.7); 1.639(0.9); 1.583(2.2); 1.548(14.6); 1.510(1.1); 1.503(1.1); 1.454(0.6); 1.410(2.3); 1.379(2.2); 1.304(1.0); 1.265(2.9); 1.241(2.8); 1.220(3.2); 1.173(0.7); 1.119(1.2); 1.089(2.2); 1.060(1.8); 1.028(0.6); 0.898(1.1); 0.882(3.0); 0.864(1.1); 0.146(0.6); 0.008(4.9); 0.000(146.4); −0.008(4.3); −0.150(0.6)
Example I-152: ¹H-NMR(400.0 MHz, d₆-DMSO):
δ = 7.94 (1H), 4.48 (1H), 4.10-4.03 (1H), 3.94-3.85 (1H), 2.35-2.28 (1H), 1.98-1.42 (6H), 1.37 (9H), 1.36 (9H), 1.28-1.18 (2H)
Example I-153: ¹H-NMR(400.0 MHz, d₆-DMSO):
δ = 7.94 (1H), 4.48 (1H), 4.10-4.03 (1H), 3.94-3.85 (1H), 2.35-2.28 (1H), 1.98-1.42 (6H), 1.37 (9H), 1.36 (9H), 1.28-1.18 (2H)
Example I-154: ¹H-NMR(400.0 MHz, d₆-DMSO):
δ = 7.94 (1H), 4.48 (1H), 4.10-4.03 (1H), 3.94-3.85 (1H), 2.35-2.28 (1H), 1.98-1.42 (6H), 1.37 (9H), 1.36 (9H), 1.28-1.18 (2H)
Example I-155: ¹H-NMR(400.0 MHz, CDCl3):
δ = 7.520(1.2); 7.286(43.4); 7.261(204.1); 7.211(0.6); 6.997(1.1); 5.396(8.3); 4.255(8.2); 4.248(8.5); 4.131(0.8); 4.108(6.7); 4.093(7.0); 4.075(8.0); 4.060(8.1); 3.773(8.8); 3.752(9.0); 3.740(7.3); 3.719(7.5); 2.418(1.1); 2.411(1.2); 2.402(1.8); 2.396(3.5); 2.390(2.4); 2.380(4.1); 2.374(4.0); 2.365(2.5); 2.358(3.4); 2.343(1.2); 2.337(1.1); 2.099(1.0); 2.080(4.1); 2.061(2.6); 2.050(4.2); 2.044(5.7); 1.811(3.9); 1.803(3.6); 1.777(6.2); 1.773(6.1); 1.750(7.6); 1.745(8.9); 1.730(4.0); 1.723(4.9); 1.714(6.3); 1.707(4.2); 1.683(3.4); 1.676(3.8); 1.652(4.7); 1.589(1.6); 1.557(6.7); 1.548(7.7); 1.532(16.0); 1.524(12.6); 1.510(6.4); 1.502(4.7); 1.488(1.0); 1.478(0.6); 1.469(0.6); 1.350(1.4); 1.326(2.4); 1.316(2.5); 1.308(2.7); 1.294(2.7); 1.284(2.6); 1.277(2.9); 1.259(5.1); 1.255(4.8); 1.241(1.6); 0.880(0.6); 0.069(0.5); 0.008(2.7); 0.000(77.5); −0.008(2.7)
Example I-156: ¹H-NMR(400.0 MHz, CDCl3):
δ = 7.521(0.9); 7.312(0.7); 7.286(48.7); 7.277(2.0); 7.262(163.4); 7.230(0.6); 6.998(0.9); 5.396(12.9); 4.255(7.8); 4.249(8.0); 4.131(1.1); 4.113(1.8); 4.108(6.9); 4.093(7.2); 4.075(8.4); 4.060(8.5); 3.773(9.0); 3.752(9.4); 3.740(7.7); 3.719(7.8); 2.956(2.0); 2.884(1.7); 2.418(1.1); 2.411(1.2); 2.403(1.8); 2.396(3.5); 2.390(2.4); 2.380(4.0); 2.374(3.9); 2.365(2.5); 2.358(3.4); 2.352(1.9); 2.343(1.3); 2.337(1.2); 2.089(2.1); 2.080(3.9); 2.062(2.6); 2.050(4.2); 2.044(6.7); 1.811(3.6); 1.803(3.4); 1.780(5.6); 1.777(5.8); 1.773(5.7); 1.750(7.3); 1.745(8.4); 1.730(3.7); 1.725(4.2); 1.722(4.5); 1.718(5.3); 1.714(5.7); 1.707(3.7); 1.690(1.1); 1.683(1.7); 1.676(1.6); 1.548(8.5); 1.557(8.6); 1.548(8.4); 1.547(8.0); 1.532(16.0); 1.524(12.7); 1.515(5.0); 1.510(6.8); 1.502(5.1); 1.489(1.1); 1.478(0.8); 1.469(0.7); 1.407(0.6); 1.350(1.4); 1.333(2.1); 1.326(2.4); 1.316(2.6); 1.308(2.8); 1.299(2.6); 1.293(2.7); 1.284(2.8); 1.277(3.3); 1.259(6.1); 1.255(5.2); 1.241(2.1); 0.880(0.8); 0.008(2.2); 0.000(61.8); −0.008(2.4)
Example I-157: ¹H-NMR(400.0 MHz, d₆-DMSO):
δ = 9.60 (1H), 8.91 (1H), 8.80 (1H), 4.05-3.92 (2H), 2.62 (3H), 1.85-1.57 (6H), 1.23-1.02 (5H)
Example I-158: ¹H-NMR(400.0 MHz, d₆-DMSO):
δ = 10.2 (1H), 9.48 (1H), 9.01 (1H), 4.02 (2H), 2.62 (3H), 1.85-1.57 (6H), 1.24-1.02 (5H)
Example I-159: ¹H-NMR(400.0 MHz, CDCl3):
δ = 9.560(1.0); 7.411(3.8); 7.260(63.5); 6.136(0.9); 4.231(1.7); 4.146(0.8); 4.133(0.9); 4.113(1.1); 4.100(1.1); 3.806(0.9); 3.784(1.1); 3.772(1.0); 3.751(0.9); 2.375(0.9); 2.088(0.8); 2.060(0.8); 1.784(1.4); 1.749(1.8); 1.721(1.4); 1.536(16.0); 1.266(1.5); 0.882(1.0); 0.000(22.8)
Example I-160: ¹H-NMR(400.0 MHz, CDCl3):
δ = 9.563(0.7); 7.519(0.6); 7.411(8.3); 7.260(120.2); 6.996(0.7); 6.135(0.8); 4.236(1.4); 4.229(1.4); 4.147(1.2); 4.132(1.2); 4.114(1.4); 4.099(1.4); 3.806(1.5); 3.784(1.5); 3.773(1.2); 3.751(1.3); 2.394(0.5); 2.374(0.6); 2.356(0.5); 2.091(0.7); 2.062(0.7); 1.820(0.8); 1.787(1.2); 1.755(1.2); 1.749(1.5); 1.735(0.6); 1.719(1.0); 1.568(1.1); 1.559(1.0); 1.536(16.0); 1.521(1.4); 1.512(1.2); 1.303(0.6); 1.258(1.1); 0.882(1.4); 0.864(0.5); 0.008(1.4); 0.000(42.8); −0.008(1.4)
Example I-161: ¹H-NMR(400.0 MHz, CDCl3):
δ = 9.597(6.4); 7.519(2.8); 7.427(58.6); 7.373(0.6); 7.310(1.6); 7.293(1.1); 7.260(475.8); 7.232(2.6); 7.209(2.4); 7.146(0.8); 6.996(2.8); 5.299(16.0); 4.228(9.4); 4.221(10.0); 4.153(7.7); 4.139(8.1); 4.120(9.4); 4.105(9.5); 3.810(9.8); 3.788(10.1); 3.776(8.5); 3.755(8.6); 2.412(1.2); 2.406(1.4); 2.398(2.2); 2.391(3.7); 2.385(2.9); 2.373(4.6); 2.352(4.4); 2.338(1.9); 2.332(1.7); 2.090(4.8); 2.061(4.9); 1.822(4.0); 1.787(8.2); 1.754(8.6); 1.748(10.9); 1.734(4.9); 1.718(7.4); 1.711(4.7); 1.686(2.2); 1.679(2.0); 1.568(9.0); 1.544(41.5); 1.520(12.3); 1.512(10.4); 1.432(2.1); 1.332(3.5); 1.304(4.0); 1.292(3.9); 1.280(4.0); 1.256(10.7); 0.881(1.9); 0.864(1.1); 0.146(0.6); 0.008(6.2); 0.000(175.7); −0.008(7.5); −0.052(1.0); −0.149(0.8)
Example I-162: ¹H-NMR(400.0 MHz, CDCl3):
δ = 9.600(3.4); 7.520(0.8); 7.427(32.5); 7.261(145.0); 6.997(0.8); 5.299(16.0); 4.228(5.2); 4.222(5.4); 4.153(4.4); 4.138(4.5); 4.120(5.2); 4.105(5.3); 3.810(5.7); 3.788(5.8); 3.777(4.8); 3.755(4.9); 2.412(0.7); 2.406(0.7); 2.398(1.2); 2.391(2.0); 2.384(1.5); 2.372(2.4); 2.358(1.7); 2.352(2.1); 2.346(1.1); 2.338(0.8); 2.331(0.7); 2.091(2.6); 2.073(1.6); 2.061(2.6); 2.053(1.6); 2.043(0.7); 1.826(2.1); 1.822(2.1); 1.801(1.5); 1.787(4.4); 1.754(4.4); 1.748(5.8); 1.734(2.2); 1.726(2.8); 1.718(3.7); 1.711(2.1); 1.695(0.6); 1.686(0.9); 1.680(0.8); 1.596(1.1); 1.568(5.0); 1.552(10.9); 1.541(9.9); 1.532(7.1); 1.520(5.4); 1.512(4.7); 1.358(0.8); 1.333(1.6); 1.322(1.7); 1.316(1.7); 1.304(1.8); 1.292(1.7); 1.281(1.7); 1.257(3.8); 0.882(0.9); 0.008(1.6); 0.006(0.7); 0.000(54.0); −0.008(1.7)
Example I-163: ¹H-NMR(400.0 MHz, d₆-DMSO):
δ = 7.838(7.0); 7.823(6.8); 7.627(2.0); 7.610(2.2); 7.602(2.7); 7.584(2.8); 7.575(2.1); 7.558(2.0); 7.457(1.7); 7.440(1.9); 7.435(2.0); 7.430(2.0); 7.418(1.9); 7.413(2.0); 7.408(1.8); 7.390(1.6); 6.654(10.8); 5.173(0.6); 5.138(16.0); 3.410(0.5); 3.370(0.8); 3.359(1.5); 3.345(2.3); 3.310(568.5); 3.278(0.6); 3.261(0.7); 2.679(1.2); 2.674(2.6); 2.670(3.6); 2.665(2.6); 2.660(1.2); 2.600(0.8); 2.523(13.7); 2.519(19.1); 2.510(198.2); 2.505(409.8); 2.501(563.2); 2.496(385.1); 2.492(174.3); 2.337(1.1); 2.332(2.4); 2.328(3.4); 2.323(2.4); 2.318(1.1); 2.072(1.1); 1.988(1.5); 1.236(0.5); 1.175(0.8); 0.008(2.0); 0.000(62.5); −0.008(1.9)
Example I-164: ¹H-NMR(400.0 MHz, d₆-DMSO):
δ = 8.05 (1H), 7.65-7.48 (2H), 5.18 (2H), 1.38 (18H)
Example I-165: ¹H-NMR(400.0 MHz, d₆-DMSO):
δ = 11.726(0.9); 7.965(6.5); 7.949(6.5); 7.632(2.1); 7.615(2.1); 7.606(2.9); 7.588(3.0); 7.581(2.2); 7.563(2.1); 7.532(1.6); 7.514(2.1); 7.482(2.1); 7.465(1.8); 6.658(4.2); 6.526(11.2); 6.393(4.7); 5.753(8.6); 5.178(16.0); 3.311(181.0); 2.670(1.7); 2.524(4.8); 2.510(95.7); 2.506(202.3); 2.501(279.8); 2.497(195.7); 2.492(89.9); 2.451(1.2); 2.328(1.4); 1.988(2.3); 1.235(5.8); 1.175(1.3); 0.000(47.8); −0.009(1.4)
Example I-166: ¹H-NMR(400.0 MHz, d₆-DMSO):
δ = 7.798(4.3); 6.491(2.9); 4.807(6.7); 3.891(2.2); 3.873(2.3); 3.716(16.0); 3.687(1.9); 3.309(150.6); 2.669(1.1); 2.523(5.6); 2.518(7.7); 2.510(85.0); 2.505(177.2); 2.500(243.6); 2.496(166.7); 2.491(74.8); 2.315(15.9); 2.189(1.8); 1.667(1.1); 1.533(1.0); 1.247(0.9); 1.157(1.7); 1.018(0.8); 0.858(1.5); 0.008(0.9); 0.000(39.5); −0.009(1.4)
Example I-167: ¹H-NMR(400.0 MHz, CDCl3):
δ = 7.260(86.1); 7.134(4.7); 4.007(3.8); 3.990(3.8); 3.874(2.8); 3.856(2.8); 2.302(16.0); 1.723(1.3); 1.690(1.0); 1.556(1.7); 1.255(0.6); 1.217(1.0); 1.212(1.2); 1.200(1.2); 1.187(0.9); 1.182(0.9); 1.050(0.6); 0.612(1.3); 0.609(1.4); 0.604(0.6); 0.598(0.6); 0.592(1.4); 0.589(1.2); 0.578(0.6); 0.345(0.6); 0.333(1.7); 0.330(1.4); 0.321(1.3); 0.318(1.7); 0.008(1.0); 0.000(31.6); −0.008(0.9)
Example I-168: ¹H-NMR(400.0 MHz, d₆-DMSO):
δ = 7.788(4.3); 6.720(2.8); 6.054(0.7); 6.028(0.8); 6.011 (0.9); 5.985(0.9); 5.754(0.9); 5.381 (1.2); 5.377(1.3); 5.338(1.1); 5.334(1.1); 5.287(0.5); 5.284(1.1); 5.279(1.0); 5.258(1.0); 5.253(1.0); 4.667(1.4); 4.663(2.4); 4.660(1.5); 4.653(1.5); 4.649(2.3); 4.646(1.4); 3.901(2.1); 3.883(2.1); 3.315(15.0); 2.521(0.5); 2.512(6.1); 2.508(12.9); 2.503(18.0); 2.499(12.5); 2.494(5.7); 2.282(16.0); 1.665(0.8); 1.564(0.7); 1.535(0.7); 1.153(1.3); 1.133(0.9); 1.020(0.6); 0.000(6.3)
Example I-169: ¹H-NMR(400.0 MHz, CDCl3):
δ = 7.262(14.6); 7.129(4.9); 5.974(1.5); 5.299(2.2); 4.438(1.0); 4.422(1.4); 4.407(1.0); 3.872(3.1); 3.854(3.1); 2.267(16.0); 1.754(0.6); 1.748(0.6); 1.723(1.7); 1.690(1.3); 1.685(1.2); 1.596(0.5); 1.325(15.5); 1.310(15.4); 1.255(1.0); 1.243(0.5); 1.210(1.0); 1.194(0.7); 1.185(0.8); 1.050(0.7); 1.021(0.6); 0.000(5.2)
Example I-170: ¹H-NMR(400.0 MHz, d₆-DMSO):
δ = 8.349(16.0); 3.947(7.2); 3.929(7.4); 3.507(0.6); 3.363(3.6); 3.313(460.0); 2.674(3.4); 2.670(4.9); 2.665(3.6); 2.598(0.5); 2.555(3.7); 2.551(5.0); 2.546(4.6); 2.541(4.2); 2.523(16.5); 2.518(23.6); 2.510(274.4); 2.505(571.0); 2.501(787.7); 2.496(548.7); 2.492(253.0); 2.332(3.3); 2.327(4.7); 2.323(4.4); 2.318(1.7); 2.072(0.7); 1.771(2.3); 1.660(2.9); 1.607(1.9); 1.564(2.9); 1.536(2.9); 1.298(1.3); 1.259(2.3); 1.236(7.8); 1.176(1.9); 1.149(5.1); 1.129(3.6); 1.012(2.4); 0.981(1.9); 0.854(1.4); 0.836(0.7); 0.050(0.5); 0.008(3.9); 0.000(149.1); −0.008(5.2); −0.150(0.5)
Example I-171: ¹H-NMR(400.0 MHz, CDCl3):
δ = 9.464(4.1); 7.763(1.3); 7.520(1.0); 7.425(36.4); 7.285(0.6); 7.261(182.1); 6.997(1.0); 5.299(16.0); 4.231(6.2); 4.224(6.5); 4.151(5.2); 4.136(5.5); 4.118(6.3); 4.103(6.5); 3.810(6.7); 3.788(6.8); 3.777(5.7); 3.755(5.8); 2.414(0.8); 2.407(0.9); 2.399(1.5); 2.392(2.4); 2.385(1.9); 2.372(3.1); 2.360(2.1); 2.353(2.9); 2.347(1.5); 2.339(1.0); 2.333(1.0); 2.093(3.2); 2.075(2.0); 2.063(3.1); 2.043(2.0); 1.821(2.5); 1.801(1.9); 1.788(5.2); 1.755(5.8); 1.749(7.0); 1.735(2.8); 1.727(3.9); 1.720(4.7);

1.713(2.7); 1.688(1.2); 1.682(1.0); 1.569(5.5); 1.549(12.5); 1.542(13.2);
1.533(9.0); 1.521(6.7); 1.512(5.9); 1.391(0.6); 1.359(1.1); 1.333(2.2);
1.324(2.2); 1.304(2.4); 1.293(2.2); 1.284(2.5); 1.276(2.1); 1.256(8.4);
0.897(0.7); 0.880(1.6); 0.863(0.8); 0.008(2.1); 0.000(65.8); −0.008(2.2)
Example I-172: $^1$H-NMR(400.0 MHz, CDCl3):
δ = 8.639(1.4); 7.518(2.5); 7.362(11.2); 7.296(0.6); 7.285(0.6); 7.283(0.5);
7.281(0.5); 7.279(0.6); 7.279(0.7); 7.278(0.8); 7.277(0.8); 7.276(0.8);
7.275(0.9); 7.275(0.9); 7.274(1.1); 7.273(1.2); 7.272(1.4); 7.271(1.4);
7.271(1.6); 7.270(1.7); 7.269(2.0); 7.268(2.4); 7.267(2.9); 7.267(3.6);
7.266(4.4); 7.265(5.4); 7.259(440.8); 7.250(2.9); 7.247(1.2); 7.246(0.9);
7.246(0.7); 7.245(0.8); 7.243(0.6); 7.242(0.6); 6.995(2.5); 4.233(1.7);
4.131(1.5); 4.117(1.4); 4.098(1.7); 4.083(1.7); 3.791(1.8); 3.770(1.8);
3.758(1.6); 3.736(1.8); 2.702(1.5); 2.685(1.6); 2.389(0.7); 2.368(0.8);
2.351(0.6); 2.085(0.8); 2.056(0.8); 2.043(0.6); 1.811(0.8); 1.783(1.3);
1.751(1.4); 1.746(1.7); 1.714(1.1); 1.562(1.3); 1.532(92.6); 1.516(1.6);
1.508(1.2); 1.301(8.0); 1.282(16.0); 1.264(7.8); 0.882(0.8); 0.146(0.5);
0.008(4.9); 0.006(2.0); 0.000(169.3); −0.007(3.2); −0.008(5.7)
Example I-173: $^1$H-NMR(400.0 MHz, CDCl3):
δ = 8.638(1.2); 7.518(3.1); 7.362(11.2); 7.292(0.5); 7.283(0.6); 7.277(1.0);
7.272(1.6); 7.271(1.8); 7.271(2.0); 7.270(2.2); 7.269(2.3); 7.268(2.7);
7.259(545.3); 7.246(0.7); 7.246(0.7); 7.245(0.6); 7.243(0.5); 7.238(0.5);
6.995(3.2); 4.233(1.6); 4.132(1.4); 4.117(1.4); 4.098(1.7); 4.084(1.7);
3.791(1.8); 3.770(1.8); 3.758(1.6); 3.736(1.5); 2.702(1.5); 2.683(1.5);
2.388(0.6); 2.368(0.7); 2.351(0.6); 2.082(0.8); 2.056(0.7); 2.044(0.8);
1.810(0.8); 1.784(1.3); 1.746(1.7); 1.714(1.1); 1.562(1.2); 1.532(126.2);
1.516(1.6); 1.507(1.3); 1.301(8.0); 1.283(16.0); 1.264(7.8); 0.882(1.0);
0.146(0.7); 0.008(6.0); 0.000(210.6); −0.008(6.8); −0.150(0.7)
Example I-174: $^1$H-NMR(400.0 MHz, CDCl3):
δ = 8.674(1.8); 7.519(1.8); 7.457(2.0); 7.439(2.2); 7.435(2.5); 7.415(2.5);
7.410(2.3); 7.393(2.0); 7.386(0.8); 7.302(6.1); 7.300(6.5); 7.287(6.6);
7.285(6.4); 7.260(314.3); 7.030(2.2); 7.014(2.3); 7.006(4.0); 6.996(2.3);
6.990(4.1); 6.982(2.4); 6.967(2.1); 5.298(1.4); 5.151(1.0); 5.128(16.0);
2.089(0.9); 1.542(3.9); 1.332(0.8); 1.284(1.2); 1.256(5.1); 0.880(0.9);
0.008(3.2); 0.000(112.8); −0.008(3.7)
Example I-175: $^1$H-NMR(400.0 MHz, CDCl3):
δ = 8.007(0.9); 7.519(0.6); 7.445(0.8); 7.428(0.9); 7.424(1.0); 7.420(1.0);
7.406(1.0); 7.403(1.0); 7.399(0.9); 7.382(0.8); 7.260(109.6); 7.234(2.8);
7.232(2.8); 7.220(2.9); 7.217(2.8); 7.020(1.0); 7.004(1.0); 6.996(2.3);
6.980(1.7); 6.972(1.6); 6.956(0.9); 5.298(1.7); 5.116(7.1); 2.685(1.0);
1.543(19.1); 1.284(7.8); 1.270(1.0); 1.265(16.0); 1.246(7.4); 0.008(1.2);
0.000(38.9); −0.008(1.1)
Example I-176: $^1$H-NMR(400.0 MHz, CDCl3):
δ = 7.47-7.44 (1H), 7.21 (1H), 7.01-6.98 (1H), 5.12 (2H), 2.75-2.05 (4H),
1.13 (6H)
Example I-177: $^1$H-NMR(400.0 MHz, CDCl3):
δ = 9.457(8.9); 7.519(5.9); 7.425(86.8); 7.309(1.4); 7.285(2.9);
7.260(1064.6); 6.996(5.6); 5.298(10.6); 4.231(13.4); 4.224(14.5);
4.152(12.2); 4.137(13.0); 4.118(15.7); 4.104(15.8); 3.810(15.4);
3.788(16.0); 3.776(13.0); 3.755(13.4); 3.012(1.7); 2.955(3.4); 2.940(1.2);
2.883(2.8); 2.414(1.9); 2.408(2.0); 2.393(5.3); 2.374(6.3); 2.354(5.7);
2.332(2.3); 2.092(6.7); 2.081 (4.8); 2.063(7.0); 1.823(5.7); 1.788(11.3);
1.755(12.5); 1.750(14.8); 1.735(5.7); 1.720(10.1); 1.713(5.6); 1.688(2.8);
1.569(11.3); 1.561(10.2); 1.537(132.8); 1.521(14.6); 1.513(12.4);
1.333(3.9); 1.317(4.1); 1.294(4.1); 1.282(3.9); 1.255(8.7); 0.146(1.3);
0.008(11.6); 0.000(373.9); −0.008(11.2); −0.150(1.3)
Example I-178: $^1$H-NMR(400.0 MHz, d$_6$-DMSO):
δ = 7.720(0.8); 7.702(14.9); 7.686(15.2); 6.627(16.0); 4.478(5.8);
4.471(6.1); 3.992(4.0); 3.973(4.0); 3.959(5.2); 3.940(5.5); 3.808(5.7);
3.792(5.8); 3.775(4.1); 3.759(4.3); 3.605(1.7); 3.362(0.5); 3.354(1.0);
3.344(2.0); 3.311(676.7); 3.270(0.8); 3.261(1.0); 2.679(1.3); 2.674(2.8);
2.670(3.8); 2.665(2.8); 2.523(14.9); 2.518(20.8); 2.510(219.8);
2.505(456.9); 2.501(629.5); 2.496(433.2); 2.492(196.9); 2.451(1.7);
2.337(1.4); 2.332(2.8); 2.327(3.9); 2.323(3.0); 2.318(1.5); 2.276(2.4);
2.072(0.9); 1.988(0.8); 1.947(2.0); 1.915(3.1); 1.822(1.3); 1.812(1.7);
1.804(1.4); 1.790(2.0); 1.784(2.9); 1.755(1.5); 1.748(1.7); 1.738(1.1);
1.684(2.3); 1.653(3.5); 1.630(2.0); 1.620(2.5); 1.597(2.0); 1.588(2.9);
1.564(0.9); 1.556(1.2); 1.495(3.3); 1.462(2.2); 1.429(1.8); 1.399(4.9);
1.391(4.2); 1.375(5.2); 1.367(4.5); 1.271(0.9); 1.258(1.2); 1.240(2.2);
1.229(2.4); 1.217(1.6); 1.199(1.8); 1.157(0.6); 0.008(2.7); 0.000(88.7);
−0.008(2.6)
Example I-179: $^1$H-NMR(400.0 MHz, CDCl3):
δ = 7.261(33.2); 6.883(5.2); 5.982(0.7); 5.979(2.2); 5.976(2.2); 5.972(0.8);
5.299(3.0); 4.802(1.3); 3.841(2.5); 3.823(2.6); 3.786(16.0); 2.535(8.6);
2.532(8.8); 1.756(0.5); 1.750(0.5); 1.725(0.8); 1.716(0.9); 1.702(0.9);
1.693(0.8); 1.671(1.1); 1.254(0.6); 1.244(0.6); 1.212(1.0); 1.192(0.7);
1.040(0.7); 1.010(0.6); 0.000(12.4)
Example I-180: $^1$H-NMR(400.0 MHz, CDCl3):
δ = 8.765(2.0); 7.519(1.2); 7.452(1.8); 7.435(2.3); 7.430(2.5); 7.427(2.4);
7.413(2.4); 7.410(2.5); 7.406(2.2); 7.388(2.2); 7.297(5.8); 7.295(6.4);
7.283(6.2); 7.280(6.3); 7.272(1.4); 7.270(1.3); 7.267(1.8); 7.260(201.5);
7.250(0.6); 7.028(2.0); 7.012(2.4); 7.004(3.9); 6.996(1.7); 6.988(3.9);
6.980(2.2); 6.964(2.0); 5.299(3.0); 5.150(1.4); 5.128(16.0); 2.043(1.1);
1.546(6.9); 1.332(0.6); 1.291(0.7); 1.284(1.1); 1.256(5.9); 1.241(0.6);
0.880(1.0); 0.008(2.1); 0.006(0.9); 0.005(1.0); 0.000(73.9); −0.008(2.3)
Example I-181: $^1$H-NMR(400.0 MHz, CDCl3):
δ = 8.085(1.1); 7.520(2.0); 7.286(1.2); 7.283(0.8); 7.261(386.3);
7.230(39.2); 7.216(39.3); 6.997(2.1); 5.299(3.2); 5.106(12.3); 4.677(1.1);
4.265(12.8); 4.258(13.4); 4.114(10.8); 4.099(11.1); 4.080(12.6);
4.066(12.8); 3.713(15.6); 3.691(16.0); 3.680(13.4); 3.658(13.8);
2.428(1.8); 2.422(2.0); 2.414(2.7); 2.408(5.2); 2.401(4.1); 2.393(4.6);
2.387(5.8); 2.375(3.9); 2.368(5.1); 2.362(3.2); 2.353(2.3); 2.347(1.8);
2.074(6.3); 2.059(4.2); 2.048(6.8); 2.044(4.1); 1.810(7.0); 1.803(6.3);
1.780(10.1); 1.775(10.5); 1.750(12.1); 1.744(14.7); 1.730(6.8); 1.725(7.2);
1.722(7.2); 1.713(9.8); 1.706(6.4); 1.690(1.9); 1.682(3.1); 1.675(2.9);
1.555(14.9); 1.548(12.0); 1.535(25.7); 1.526(21.6); 1.510(7.8); 1.500(6.5);
1.476(1.5); 1.467(1.4); 1.407(6.2); 1.355(2.3); 1.330(4.0); 1.320(4.0);
1.299(4.2); 1.278(3.4); 1.254(9.3); 0.880(1.1); 0.145(0.6); 0.070(0.7);
0.008(4.2); 0.000(136.6); −0.008(4.5)
Example I-182: $^1$H-NMR(400.0 MHz, CDCl3):
δ = 8.085(0.8); 7.520(2.0); 7.299(1.2); 7.294(1.0); 7.261(367.6);
7.245(39.4); 7.230(39.1); 6.997(2.0); 5.299(13.3); 5.211(1.9); 4.678(1.0);
4.432(0.5); 4.262(12.8); 4.256(13.5); 4.120(10.8); 4.106(11.1);
4.087(12.7); 4.073(12.9); 3.721(15.6); 3.700(16.0); 3.688(13.3);
3.666(13.8); 2.428(1.8); 2.421(2.0); 2.414(2.6); 2.407(5.1); 2.400(4.1);
2.386(5.8); 2.375(3.7); 2.367(5.2); 2.361(3.1); 2.353(2.0); 2.347(1.9);
2.127(4.5); 2.116(5.3); 2.088(3.4); 2.079(6.4); 2.060(4.2); 2.049(6.6);
2.041(4.0); 2.006(0.6); 1.811 (6.1); 1.777(9.7); 1.773(9.8); 1.750(11.8);
1.745(14.1); 1.730(5.9); 1.722(7.0); 1.714(9.4); 1.707(5.7); 1.683(2.6);
1.676(2.4); 1.555(13.2); 1.549(11.7); 1.536(25.2); 1.527(21.2); 1.511(9.1);
1.502(6.7); 1.478(1.4); 1.469(1.6); 1.356(2.1); 1.332(4.2); 1.321(3.9);
1.300(4.0); 1.280(3.6); 1.255(7.3); 0.880(1.0); 0.146(0.6); 0.070(0.6);
0.008(3.7); 0.000(130.8); −0.008(4.2); −0.150(0.6)
Example I-183: $^1$H-NMR(400.0 MHz, CDCl3):
δ = 8.805(1.9); 7.519(0.8); 7.361(9.2); 7.346(9.2); 7.260(148.8);
6.996(0.8); 5.299(16.0); 4.246(3.4); 4.239(3.6); 4.148(2.7); 4.133(2.7);
4.114(3.1); 4.100(3.1); 3.754(3.6); 3.732(3.7); 3.720(3.1); 3.699(3.2);
2.389(1.4); 2.382(1.1); 2.373(1.8); 2.367(1.7); 2.358(1.2); 2.351(1.5);
2.336(2.0); 2.085(1.7); 2.067(1.1); 2.058(1.7); 2.043(1.1); 1.822(1.5);
1.813(1.6); 1.785(2.9); 1.779(2.4); 1.753(2.5); 1.747(3.3); 1.733(1.8);
1.728(1.6); 1.720(2.0); 1.714(2.4); 1.707(1.4); 1.682(0.6); 1.676(0.6);
1.592(0.6); 1.566(3.2); 1.544(10.7); 1.534(6.1); 1.520(2.8); 1.512(2.0);
1.358(0.5); 1.332(1.2); 1.316(1.2); 1.303(1.3); 1.292(1.1); 1.284(1.3);
1.276(1.2); 1.257(3.5); 0.880(0.7); 0.008(1.8); 0.000(56.2); −0.008(1.9)
Example I-184: $^1$H-NMR(400.0 MHz, CDCl3):
δ = 7.260(34.3); 7.062(2.6); 7.047(2.6); 3.820(3.6); 3.802(3.6); 2.352(0.6);
1.769(0.7); 1.734(1.6); 1.700(1.5); 1.284(0.7); 1.256(6.2); 1.223(1.3);
1.198(1.0); 1.163(7.8); 1.145(16.0); 1.127(7.3); 1.059(0.9); 1.029(0.7);
0.880(0.9); 0.000(12.7)

B) Formulation Examples a) A dust is obtained by mixing 10 parts by weight of a compound of the formulae (G1) or (G2) and 90 parts by weight of talc as inert substance and comminuting the mixture in a hammer mill.

b) A wettable powder which is readily dispersible in water is obtained by mixing 25 parts by weight of a compound of the formulae (G1) or (G2), 64 parts by weight of kaolin-containing quartz as inert substance, 10 parts by weight of potassium lignosulphonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formulae (G1) or (G2) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formulae (G1) or (G2), 75 parts by weight of cyclohexanone as solvent and 10 parts by weight of oxyethylated nonylphenol as emulsifier.
e) Water-dispersible granules are obtained by mixing
   75 parts by weight of a compound of the formulae (G1) or (G2),
   10 parts by weight of calcium lignosulphonate,
   5 parts by weight of sodium laurylsulphate,
   3 parts by weight of polyvinyl alcohol and
   7 parts by weight of kaolin,
   grinding the mixture in a pinned-disk mill, and granulating the powder in a fluidized bed by spray application of water as a granulating liquid.
f) Water-dispersible granules are also obtained by homogenizing and precomminuting
   25 parts by weight of a compound of the formulae (G1) or (G2),
   5 parts by weight of sodium 2,2'-dinaphthylmethane-6,6'-disulphonate,
   2 parts by weight of sodium oleoylmethyltaurinate,
   1 part by weight of polyvinyl alcohol,
   17 parts by weight of calcium carbonate and
   50 parts by weight of water,
on a colloid mill, subsequently grinding the mixture in a bead mill and atomizing and drying the resulting suspension in a spray tower by means of a single-substance nozzle.

(C) Biological Examples

Herbicidal activities of the compounds of the formulae (G1) or (G2) according to the invention were investigated against the following harmful plants:

ALOMY=*Alopecurus myosuroides*
ECHCG=*Echinochloa crus-galli*
SETVI=*Setaria viridis*
ABUTH=*Abutilon theophrasti*
AMARE=*Amaranthus retroflexus*
PHBPU=*Pharbitis purpurea*
POLCO=*Polygonum convolvulus* (=*Fallopia convolvulus*)
STEME=*Stellaria media*
VIOTR=*Viola tricolor*

Herbicidal Effect and Crop Plant Compatibility Pre-Emergence

Seeds of mono- and dicotyledonous weed plants and crop plants are sown in wood-fiber pots in sandy loam and covered with soil. The compounds according to the invention, formulated in the form of wettable powders (WP) or as emulsifiable concentrates (EC), are then applied to the surface of the covering soil as aqueous suspension or emulsion, with the addition of 0.5% of an additive, at an application rate of 600 l of water/ha (converted).

Following treatment, the pots are placed in a greenhouse and kept under optimum growth conditions for the test plants. The visual grading of the damage to the test plants is carried out after ca. 3 weeks in comparison to untreated controls (herbicidal effect in percent (%): 100% effect=plants have died off, 0% effect=as control plants).

TABLE 5

| Example Number | Dosage | Unit | SETVI | AMARE | STEME | VIOTR | ALOMY | MATIN |
|---|---|---|---|---|---|---|---|---|
| I-128 | 320 | g/ha | 100 | 100 | 100 | 100 | 100 | 100 |
| I-161 | 320 | g/ha | 100 | 100 | 100 | 100 | 100 | 100 |
| I-156 | 320 | g/ha | 100 | 100 | 100 | 100 | 100 | 100 |
| I-127 | 320 | g/ha | 100 | 100 | 100 | 100 | 100 | 100 |
| I-163 | 320 | g/ha | 100 | 100 | 100 | 100 | 100 | 100 |
| I-172 | 320 | g/ha | 100 | 100 | 100 | 100 | 100 | 100 |
| I-138 | 320 | g/ha | 100 | 100 | 100 | 100 | 100 | 90 |
| I-064 | 320 | g/ha | 100 | 100 | 100 | 100 | 100 | 100 |
| I-086 | 320 | g/ha | 100 | 100 | 100 | 100 | 100 | 100 |
| I-077 | 320 | g/ha | 100 | 100 | 100 | 100 | 100 | 90 |
| I-081 | 320 | g/ha | 100 | 100 | 100 | 100 | 100 | 100 |
| I-078 | 320 | g/ha | 100 | 100 | 100 | 100 | 100 | 100 |
| I-160 | 320 | g/ha | 100 | 100 | 100 | 100 | 100 | 100 |
| I-165 | 320 | g/ha | 100 | 100 | 100 | 100 | 100 | 100 |
| I-136 | 320 | g/ha | 100 | 100 | 100 | 100 | 100 | 90 |
| I-087 | 320 | g/ha | 100 | 100 | 100 | 100 | 100 | 90 |
| I-049 | 320 | g/ha | 100 | 100 | 100 | 90 | 80 | 80 |
| I-048 | 320 | g/ha | 100 | 100 | 100 | 100 | 80 | 90 |
| I-084 | 320 | g/ha | 100 | 100 | 100 | 100 | 100 | 100 |
| I-171 | 320 | g/ha | 100 | 100 | 100 | 100 | 100 | 100 |
| I-088 | 320 | g/ha | 100 | 100 | 100 | 100 | 100 | 100 |
| I-029 | 320 | g/ha | 90 | 100 | 90 | 100 | 90 | 90 |
| I-028 | 320 | g/ha | 100 | 90 | 100 | 100 | 90 | 90 |
| I-083 | 320 | g/ha | 100 | 100 | 100 | 100 | 100 | 100 |
| I-047 | 320 | g/ha | 90 | 100 | 100 | 100 | 80 | 90 |
| I-054 | 320 | g/ha | 100 | 100 | 100 | 100 | 90 | 100 |

TABLE 6

| Example Number | Dosage | Unit | SETVI | AMARE | VIOTR |
|---|---|---|---|---|---|
| I-039 | 320 | g/ha | 100 | 100 | 100 |
| I-135 | 320 | g/ha | 100 | 100 | 100 |
| I-085 | 320 | g/ha | 100 | 100 | 100 |
| I-051 | 320 | g/ha | 90 | 90 | 100 |
| I-144 | 320 | g/ha | 90 | 100 | 100 |
| I-035 | 320 | g/ha | 100 | 100 | 80 |

TABLE 6-continued

| Example Number | Dosage | Unit | SETVI | AMARE | VIOTR |
|---|---|---|---|---|---|
| I-007 | 320 | g/ha | 80 | 100 | 90 |
| I-159 | 320 | g/ha | 100 | 100 | 100 |
| I-082 | 320 | g/ha | 100 | 100 | 100 |
| I-102 | 320 | g/ha | 100 | 100 | 100 |
| I-044 | 320 | g/ha | 90 | 100 | 100 |

TABLE 6-continued

| Example Number | Dosage | Unit | SETVI | AMARE | VIOTR |
|---|---|---|---|---|---|
| I-173 | 320 | g/ha | 100 | 90 | 100 |
| I-033 | 320 | g/ha | 100 | 100 | 100 |
| I-034 | 320 | g/ha | 100 | 100 | 100 |
| I-036 | 320 | g/ha | 90 | 100 | 80 |
| I-022 | 320 | g/ha | 100 | 100 | 100 |
| I-170 | 320 | g/ha | 100 | 100 | 90 |
| I-155 | 320 | g/ha | 100 | 80 | 100 |
| I-046 | 320 | g/ha | 100 | 100 | 90 |
| I-118 | 320 | g/ha | 90 | 90 | 80 |
| I-056 | 320 | g/ha | 90 | 90 | 100 |
| I-133 | 320 | g/ha | 90 | 90 | 100 |
| I-167 | 320 | g/ha | 100 | 100 | 100 |
| I-107 | 320 | g/ha | 80 | 100 | 100 |
| I-080 | 320 | g/ha | 80 | 80 | 100 |
| I-070 | 320 | g/ha | 100 | 100 | 100 |
| I-027 | 320 | g/ha | 90 | 100 | 90 |
| I-079 | 320 | g/ha | 100 | 100 | 100 |
| I-032 | 320 | g/ha | 100 | 80 | 80 |
| I-023 | 320 | g/ha | 90 | 100 | 90 |
| I-103 | 320 | g/ha | 80 | 90 | 100 |
| I-021 | 320 | g/ha | 90 | 100 | 100 |
| I-105 | 320 | g/ha | 100 | 100 | 100 |
| I-158 | 320 | g/ha | 80 | 90 | 100 |

At the same time, compounds according to the invention leave graminaceous crops such as barley, wheat, rye, millet, corn or rice practically undamaged in the pre-emergence method, even at high dosages of active ingredient. Moreover, some substances also leave dicotyledonous crops such as soybean, cotton, rapeseed, or sugar beet undamaged.

Some of the compounds according to the invention exhibit high selectivity and are therefore suitable pre-emergence for controlling undesired plant growth in agricultural crops.

Herbicidal Effect and Crop Plant Compatibility Post-Emergence

Seeds of mono- and dicotyledonous weed plants and crop plants are sown in wood-fiber pots in sandy loam, covered with soil and grown in a greenhouse under controlled growth conditions. 2 to 3 weeks after sowing, the test plants are sprayed in the single-leaf stage. The compounds according to the invention, formulated in form of wettable powders (WP) or as emulsifiable concentrates (EC), are then sprayed onto the green plant parts as aqueous suspension or emulsion, with the addition of 0.5% of an additive, at an application rate of 600 l of water/ha (converted). After the test plants had been in the greenhouse for ca. 3 weeks under optimum growth conditions, the effect of the preparations is assessed visually in comparison with untreated controls (herbicidal effect in percent (%): 100% effect=plants have died off, 0% effect=as control plants).

TABLE 7

| Example Number | Dosage | Unit | SETVI | AMARE | STEME | VIOTR | MATIN | PHBPU | POLCO |
|---|---|---|---|---|---|---|---|---|---|
| I-128 | 320 | g/ha | 100 | 100 | 100 | 100 | 100 | 100 | 100 |
| I-160 | 320 | g/ha | 100 | 100 | 100 | 100 | 80 | 100 | 100 |
| I-064 | 320 | g/ha | 100 | 100 | 100 | 100 | 100 | 100 | 100 |
| I-171 | 320 | g/ha | 100 | 100 | 100 | 100 | 90 | 100 | 100 |
| I-161 | 320 | g/ha | 100 | 100 | 100 | 100 | 80 | 100 | 100 |
| I-127 | 320 | g/ha | 100 | 100 | 100 | 100 | 100 | 100 | 100 |
| I-165 | 320 | g/ha | 90 | 100 | 100 | 100 | 100 | 80 | 100 |
| I-136 | 320 | g/ha | 90 | 100 | 100 | 100 | 100 | 100 | 100 |
| I-007 | 320 | g/ha | 100 | 100 | 100 | 100 | 100 | 100 | 100 |
| I-156 | 320 | g/ha | 100 | 100 | 100 | 100 | 80 | 100 | 100 |

TABLE 8

| Example Number | Dosage | Unit | SETVI | AMARE | VIOTR | ABUTH |
|---|---|---|---|---|---|---|
| I-163 | 320 | g/ha | 90 | 100 | 90 | 90 |
| I-172 | 320 | g/ha | 80 | 100 | 100 | 100 |
| I-083 | 320 | g/ha | 100 | 100 | 100 | 80 |
| I-039 | 320 | g/ha | 100 | 100 | 100 | 100 |
| I-084 | 320 | g/ha | 100 | 100 | 100 | 100 |

TABLE 9

| Example Number | Dosage | Unit | SETVI | AMARE | VIOTR |
|---|---|---|---|---|---|
| I-088 | 320 | g/ha | 100 | 100 | 100 |
| I-077 | 320 | g/ha | 90 | 100 | 90 |
| I-102 | 320 | g/ha | 100 | 100 | 100 |
| I-054 | 320 | g/ha | 100 | 100 | 100 |
| I-085 | 320 | g/ha | 100 | 100 | 100 |
| I-086 | 320 | g/ha | 100 | 100 | 100 |
| I-113 | 320 | g/ha | 100 | 100 | 100 |
| I-108 | 320 | g/ha | 100 | 100 | 100 |
| I-138 | 320 | g/ha | 80 | 100 | 100 |
| I-118 | 320 | g/ha | 100 | 100 | 100 |
| I-079 | 320 | g/ha | 90 | 100 | 100 |
| I-082 | 320 | g/ha | 100 | 100 | 100 |
| I-048 | 320 | g/ha | 100 | 100 | 100 |
| I-080 | 320 | g/ha | 100 | 100 | 80 |
| I-070 | 320 | g/ha | 100 | 100 | 100 |
| I-081 | 320 | g/ha | 100 | 100 | 100 |
| I-078 | 320 | g/ha | 100 | 100 | 80 |
| I-044 | 320 | g/ha | 100 | 100 | 100 |
| I-087 | 320 | g/ha | 100 | 100 | 100 |
| I-135 | 320 | g/ha | 90 | 100 | 100 |
| I-042 | 320 | g/ha | 90 | 100 | 100 |
| I-120 | 320 | g/ha | 100 | 100 | 100 |
| I-049 | 320 | g/ha | 100 | 90 | 100 |
| I-036 | 320 | g/ha | 100 | 90 | 100 |
| I-020 | 320 | g/ha | 100 | 100 | 100 |
| I-023 | 320 | g/ha | 90 | 100 | 100 |
| I-072 | 320 | g/ha | 80 | 100 | 100 |
| I-021 | 320 | g/ha | 100 | 100 | 80 |
| I-115 | 320 | g/ha | 100 | 100 | 100 |
| I-142 | 320 | g/ha | 100 | 100 | 80 |
| I-143 | 320 | g/ha | 100 | 100 | 100 |
| I-047 | 320 | g/ha | 90 | 90 | 100 |
| I-103 | 320 | g/ha | 100 | 100 | 100 |

TABLE 9-continued

| Example Number | Dosage | Unit | SETVI | AMARE | VIOTR |
|---|---|---|---|---|---|
| I-141 | 320 | g/ha | 100 | 100 | 100 |
| I-132 | 320 | g/ha | 100 | 80 | 90 |
| I-147 | 320 | g/ha | 80 | 100 | 100 |
| I-126 | 320 | g/ha | 80 | 100 | 100 |
| I-056 | 320 | g/ha | 100 | 90 | 90 |
| I-134 | 320 | g/ha | 80 | 100 | 100 |

At the same time, compounds according to the invention leave graminaceous crops such as barley, wheat, rye, millet, corn or rice practically undamaged in the post-emergence method, even at high dosages of active ingredient. Moreover, some substances also leave dicotyledonous crops such as soybean, cotton, rapeseed, or sugar beet undamaged. Some of the compounds according to the invention exhibit high selectivity and are therefore suitable post-emergence for controlling undesired plant growth in agricultural crops.

Fungicidal Examples

1) Example: In Vivo Preventive Test on *Alternaria brassicae* (Leaf Spot on Radish or Cabbage)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of radish or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Alternaria brassicae* spores. The contaminated radish or cabbage plants were incubated for 6 days at 20° C. and at 100% relative humidity.

The test was evaluated 6 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: I-020; I-027; I-028; I-034; I-108

2) Example: In Vivo Preventive Test on *Botrytis cinerea* (Grey Mould)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Botrytis cinerea* spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: I-030; I-032; I-056; I-115; I-128; I-136; I-138; I-141; I-143; I-147; I-155; I-166; I-168; I-169

In this test, the following compounds according to the invention showed efficacy of at least 70% at a concentration of 100 ppm of active ingredient: I-028; I-113; I-167

3) Example: In Vivo Preventive Test on *Phytophthora infestans* (Tomato Late Blight)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of tomato were treated by spraying the active ingredient prepared as described above.

Control plants were treated only with an aqueous solution of Acetone/Dimethyl sulfoxide/Tween® 80.

After 24 hours, the plants were contaminated by spraying the leaves with an aqueous suspension of *Phytophthora infestans* spores. The contaminated tomato plants were incubated for 5 days at 16-18° C. and at 100% relative humidity.

The test was evaluated 5 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: i-009; I-016; I-017; I-018; I-020; I-023; I-025; I-027; I-029; I-032; I-034; I-035; I-036; I-037; I-038; I-041; I-042; I-043; I-047; I-049; I-050; I-056; I-063; I-067; I-068; I-069; I-070; I-072; I-090; I-103; I-104; I-105; I-108; I-112; I-114; I-115; I-119; I-122; I-125; I-130; I-131; I-132; I-134; I-138; I-141; I-143; I-146; I-147; I-155; I-159

In this test, the following compounds according to the invention showed efficacy of at least 70% at a concentration of 100 ppm of active ingredient: I-028; I-077; I-080; I-081; I-113; I-118; I-120; I-123; I-133; I-136

4) Example: In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of wheat were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Puccinia recondita* spores. The contaminated wheat plants were incubated for 24 hours at 20° C. and at 100% relative humidity and then for 10 days at 20° C. and at 70-80% relative humidity.

The test was evaluated 11 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: I-069; I-070; I-080; I-081; I-088; I-090; I-103; I-105; I-108; I-113; I-118; I-120; I-123; I-125; I-130; I-132; I-133; I-141; I-143; I-147; I-155; I-158; I-159; I-168

In this test, the following compounds according to the invention showed efficacy of at least 70% at a concentration of 100 ppm of active ingredient: I-054; I-064; I-077; I-078; I-083; I-085; I-086; I-087; I-156; I-160; I-163; I-182

5) Example: In Vivo Preventive Test on *Septoria tritici* (Leaf Spot on Wheat)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of wheat were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Septoria tritici* spores. The contaminated wheat plants were incubated for 72 hours at 18° C. and at 100% relative humidity and then for 21 days at 20° C. and at 90% relative humidity.

The test was evaluated 24 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: I-016; I-017; I-020; I-021; I-022; I-023; I-027; I-028; I-029; I-032; I-034; I-035; I-070; I-073; I-081; I-090; I-106; I-118; I-119; I-120; I-122; I-123; I-130; I-131; I-132; I-133; I-163

In this test, the following compounds according to the invention showed efficacy of at least 70% at a concentration of 100 ppm of active ingredient: I-025; I-042; I-072; I-077; I-078; I-086; I-102; I-103; I-105; I-115; I-136; I-147; I-155

6) Example: In Vivo Preventive Test on *Sphaerotheca fuliginea* (Powdery Mildew on Cucurbits)

Solvent: 5% by volume of Dimethyl sulfoxide
10% by volume of Acetone
Emulsifier: 1 l of Tween® 80 per mg of active ingredient The active ingredients were made soluble and homogenized in a mixture of Dimethyl sulfoxide/Acetone//Tween® 80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Sphaerotheca fuliginea* spores. The contaminated gherkin plants were incubated for 72 hours at 18° C. and at 100% relative humidity and then for 12 days at 20° C. and at 70-80% relative humidity.

The test was evaluated 15 days after the inoculation. 0% means an efficacy which corresponds to that of the control plants while an efficacy of 100% means that no disease was observed.

In this test, the following compounds according to the invention showed efficacy of at least 70% at a concentration of 500 ppm of active ingredient: I-080; I-104; I-108; I-113; I-119; I-130; I-133; I-134; I-141; I-157; I-166; I-169

In this test, the following compounds according to the invention showed efficacy of at least 70% at a concentration of 100 ppm of active ingredient: I-028; I-077; I-086; I-088; I-105; I-118; I-120; I-168

Insecticidal Examples

1) *Meloidogyne incognita*—Test
Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means no galls were found and 0% means the number of galls found on the roots of the treated plants was equal to that in untreated control plants.

In this test, for example, the following compounds from the preparation examples showed good activity of 90% at an application rate of 20 ppm: I-038, I-042, I-049, I1-050

2) *Myzus persicae*—Spray Test
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 5 days mortality in % is determined. 100% means all aphids have been killed and 0% means none of the aphids have been killed.

In this test, for example, the following compounds from the preparation examples showed good activity of 100% at an application rate of 500 g/ha: I-043, I-077, I-081, I-083, I-084, I-086, I-088

In this test, for example, the following compounds from the preparation examples showed good activity of 90% at an application rate of 500 g/ha: I-007, I-037, I-042, I-049, I-072, I-080, I-103

3) *Nezara viridula*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Barley plants (*Hordeum vulgare*) infested with larvae of the southern green stink bug (*Nezara viridula*) are sprayed with a test solution containing the desired concentration of the active ingredient.

After 4 days mortality in % is determined. 100% means all the stink bugs have been killed; 0% means none of the stink bugs have been killed.

In this test, for example, the following compounds from the preparation examples showed good activity of 90% at an application rate of 500 g/ha: I-078, I-087, I-102

4) *Nilaparvata lugens*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Rice plants (*Oryza sativa*) are sprayed with a preparation of the active ingredient of the desired concentration and the plants are infested with the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of 100% at an application rate of 500 g/ha: 1-007, I1-087

5) *Phaedon cochleariae*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks are sprayed with a preparation of the active ingredient of the desired concentration. Once dry, the leaf disks are infested with mustard beetle larvae (*Phaedon cochleariae*).

After 7 days mortality in % is determined. 100% means all beetle larvae have been killed and 0% means none of the beetle larvae have been killed.

In this test, for example, the following compounds from the preparation examples showed good activity of 83% at an application rate of 500 g/ha: I-084

6) *Spodoptera frugiperda*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of 100% at an application rate of 500 g/ha: I-007, I-037, I-047, I-049, I-070, I-077, I-078, I-081, I-083, I-084, I-085, I-086, I-087, I-088, I-102

7) *Tetranychus urticae*—Spray Test OP-Resistant
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

French bean (*Phaseolus vulgaris*) leaf disks infected with all instars of the two spotted spidermite (*Tetranychus urticae*), are sprayed with a preparation of the active ingredient of the desired concentration.

After 6 days mortality in % is determined. 100% means all spider mites have been killed and 0% means none of the spider mites have been killed.

In this test, for example, the following compounds from the preparation examples showed good activity of 100% at an application rate of 500 g/ha: I-047, I-078, I-085, I-087

In this test, for example, the following compounds from the preparation examples showed good activity of 95% at an application rate of 500 g/ha: I-086, I-088

In this test, for example, the following compounds from the preparation examples showed good activity of 90% at an application rate of 500 g/ha: I-043, I-072, I-077, I-081, I-083, I-084

The invention claimed is:
1. A Compound of the formulae (G1) and (G2) and/or salt thereof

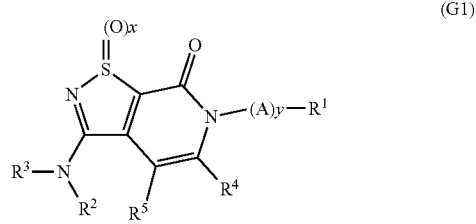

(G1)

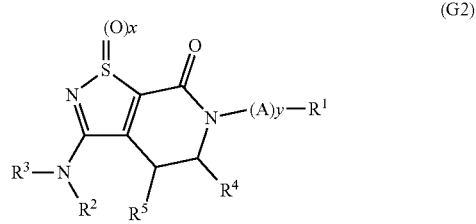

(G2)

in which
A is CR⁶R⁷,
x is 0, 1 or 2, $R^1$ is hydrogen, $(C_1-C_8)$-alkyl, $(C_2-C_8)$-alkenyl, $(C_2-C_8)$-alkynyl, $(C_1-C_8)$-alkoxy, $(C_1-C_8)$-alkoxy-$(C_1-C_8)$-alkyl, $(C_1-C_8)$-alkylthio, $(C_3-C_8)$-cycloalkyl, $(C_3-C_8)$-cycloalkenyl, $(C_3-C_8)$-cycloalkyl-$(C_1-C_8)$-alkyl, $(C_3-C_8)$-cycloalkenyl-$(C_1-C_8)$-alkyl, $(C_3-C_8)$-cycloalkoxy, $(C_3-C_8)$-cycloalkyl-$(C_1-C_8)$-alkoxy, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, aryloxy, heteroaryloxy, heterocyclyloxy, wherein all these residues are unsubstituted or substituted by one or more residues from the group consisting of halogen, nitro, hydroxyl, cyano, $NR^{13}R^{14}$, $(C_1-C_8)$-alkyl, $(C_1-C_8)$-haloalkyl, $(C_1-C_8)$-alkoxy, $(C_1-C_8)$-haloalkoxy, $(C_1-C_8)$-alkylthio, $(C_1-C_8)$-alkylsulphinyl, $(C_1-C_8)$-alkylsulphonyl, $(C_1-C_8)$-haloalkylthio, $(C_1-C_8)$-haloalkylsulphinyl, $(C_1-C_8)$-haloalkylsulphonyl, $(C_1-C_8)$-alkoxycarbonyl, $(C_1-C_8)$-haloalkoxycarbonyl, $(C_1-C_8)$-alkylcarboxy, $(C_3-C_8)$-cycloalkyl, $(C_3-C_8)$-cycloalkyl-$(C_1-C_8)$-alkyl, $(C_1-C_8)$-alkoxycarbonyl-$(C_1-C_8)$-alkyl, hydroxycarbonyl, hydroxycarbonyl-$(C_1-C_8)$-alkyl, $R^{13}R^{14}N$-carbonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, $R^2$, $R^3$ are each independently hydrogen, $(C_1-C_8)$-alkyl, $(C_2-C_8)$-alkenyl, $(C_2-C_8)$-alkynyl, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_1-C_8)$-alkoxyphenyl, $(C_1-C_8)$-alkoxyphenyl-$(C_1-C_8)$-alkyl, $(C_1-C_8)$-alkoxy-$(C_1-C_8)$-alkylcarbonyl, $(C_1-C_8)$-alkoxy-$(C_1-C_8)$-alkoxy-$(C_1-C_8)$-alkylcarbonyl, $(C_1-C_8)$-alkoxycarbonyl, $(C_2-C_8)$-alkenyloxycarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, $R^{13}R^{14}N$-carbonyl, $(C_1-C_8)$-alkylthio, $(C_1-C_8)$-alkylthiocarbonyl, $(C_1-C_8)$-alkylsulphinyl, $(C_1-C_8)$-alkylsulphonyl, $(C_1-C_8)$-alkylthio-$(C_1-C_8)$-alkyl, $(C_1-C_8)$-alkylsulphinyl-$(C_1-C_8)$-alkyl, $(C_1-C_8)$-alkylsulphonyl-$(C_1-C_8)$-alkyl, $(C_1-C_8)$-alkylthio-$(C_1-C_8)$-alkylcarbonyl, $(C_1-C_8)$-alkylsulphinyl-$(C_1-C_8)$-alkylcarbonyl, $(C_1-C_8)$-alkylsulphonyl-$(C_1-C_8)$-alkylcarbonyl, $(C_1-C_8)$-alkoxycarbonyl-$(C_1-C_8)$-alkylcarbonyl, $(C_3-C_8)$-cycloalkyl, $(C_3-C_8)$-cycloalkenyl, $(C_3-C_8)$-cycloalkyl-$(C_1-C_8)$-alkyl, $(C_3-C_8)$-cycloalkenyl-$(C_1-C_8)$-alkyl, $(C_3-C_8)$-cycloalkylcarbonyl, $(C_3-C_8)$-cycloalkenylcarbonyl, $(C_3-C_8)$-cycloalkyl-$(C_1-C_8)$-alkylcarbonyl, $(C_3-C_8)$-cycloalkenyl-$(C_1-C_8)$-alkylcarbonyl, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, arylcarbonyl, aryl-$(C_1-C_8)$-alkylcarbonyl, heteroarylcarbonyl, heteroaryl-$(C_1-C_8)$-alkylcarbonyl, heterocyclylcarbonyl, or heterocyclyl-$(C_1-C_8)$-alkylcarbonyl, wherein all these residues are unsubstituted or substituted by one or more residues from the group consisting of halogen, nitro, hydroxyl, cyano, $NR^{13}R^{14}$, $(C_1-C_8)$-haloalkyl, $(C_1-C_8)$-alkoxy, $(C_1-C_8)$-haloalkoxy, $(C_1-C_8)$-alkylthio, $(C_1-C_8)$-alkylsulphinyl, $(C_1-C_8)$-alkylsulphonyl, $(C_1-C_8)$-haloalkylthio, $(C_1-C_8)$-haloalkylsulphinyl, $(C_1-C_8)$-haloalkylsulphonyl, $(C_1-C_8)$-alkoxycarbonyl, $(C_1-C_8)$-haloalkoxycarbonyl, $(C_1-C_8)$-alkylcarboxy, $(C_3-C_8)$-cycloalkyl, $(C_3-C_8)$-cycloalkyl-$(C_1-C_8)$-alkyl, $(C_1-C_8)$-alkoxycarbonyl-$(C_1-C_8)$-alkyl, hydroxycarbonyl, hydroxycarbonyl-$(C_1-C_4)$-alkyl, $R^{13}R^{14}N$-carbonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $NR^2R^3$ is $-N=CR^8R^9$ or $-N=S(O)_nR^{10}R^{11}$, $R^4$, $R^5$ are each independently hydrogen, formyl, cyano, halogen, oxytetrahydropyranmethyl, $(C_1-C_8)$-alkoxycarbonyl, $(C_1-C_8)$-alkylcarbonyloxy, $(C_1-C_6)$-alkylcarbonyloxy-$(C_1-C_6)$-alkyl, $(C_1-C_8)$-alkylsilyl, $(C_2-C_6)$-alkenylcarbonyl, $(C_2-C_6)$-alkynylcarbonyl, $(C_3-C_8)$-cycloalkyl-$(C_1-C_8)$-alkylaminocarbonyl, aminocarbonyl, $(C_1-C_8)$-alkylcarboxy, $(C_1-C_8)$-alkyl, $(C_2-C_8)$-alkenyl, $(C_2-C_8)$-alkynyl, $NR^{13}R^{14}$, $R^{13}R^{14}N-(C_1-C_8)$-alkyl, $(C_1-C_8)$-alkoxy, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_1-C_8)$-alkylthio, $(C_1-C_8)$-alkylsulphinyl, $(C_1-C_8)$-alkylsulphonyl, $(C_1-C_8)$-alkylthio-$(C_1-C_8)$-alkyl, $(C_1-C_8)$-alkylsulphinyl-$(C_1-C_8)$-alkyl, $(C_1-C_8)$-alkylsulphonyl-$(C_1-C_8)$-alkyl, $(C_3-C_8)$-cycloalkyl, $(C_3-C_8)$-cycloalkenyl, $(C_3-C_8)$-cycloalkyl-$(C_1-C_8)$-alkyl, $(C_3-C_8)$-cycloalkenyl-$(C_1-C_8)$-alkyl, $(C_3-C_8)$-cycloalkoxy, $(C_3-C_8)$-cycloalkyl-$(C_1-C_8)$-alkoxy, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, aryloxy, heteroaryloxy, heterocyclyloxy, wherein all these residues are unsubstituted or substituted by one or more residues from the group consisting of halogen, hydroxyl, cyano, $(C_1-C_6)$-alkoxy, $(C_1-C_6)$-alkyl, $(C_1-C_8)$-haloalkyl, $(C_1-C_8)$-haloalkoxy, $(C_1-C_8)$-alkylthio, $(C_1-C_8)$-alkylsulphinyl, $(C_1-C_8)$-alkylsulphonyl, $(C_1-C_8)$-haloalkylthio, $(C_1-C_8)$-haloalkylsulphinyl, $(C_1-C_8)$-haloalkylsulphonyl, $(C_1-C_6)$-alkoxycarbonyl, $(C_1-C_6)$-alkoxycarbonyl-$(C_1-C_6)$-alkoxy, $(C_3-C_6)$-cycloalkyl-$(C_1-C_6)$-alkoxyimino, $(C_2-C_6)$-alkenyloxyimino, $(C_1-C_6)$-alkyloxyimino, aminocarbonyl and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, provided that $R^4$ and $R^5$ are not hydrogen at the same time, and wherein $R^4$ and $R^5$ together do not form an aromatic ring, $R^6$, $R^7$ are each independently hydrogen, cyano, halogen, $(C_1-C_8)$-alkyl, $(C_2-C_8)$-alkenyl, $(C_2-C_8)$-alkynyl, or $(C_3-C_8)$-cycloalkyl, $R^8$, $R^9$ are each independently hydrogen, $(C_1-C_8)$-alkyl, $(C_2-C_8)$-alkenyl, $(C_2-C_8)$-alkynyl, $(C_2-C_8)$-alkenyloxy, $(C_2-C_8)$-alkynyloxy, $NR^{13}R^{14}$, $(C_1-C_8)$-alkoxy-$(C_1-C_8)$-alkyl, $(C_1-C_8)$-alkoxy-$(C_1-C_8)$-alkoxy-$(C_1-C_8)$-alkyl, $(C_1-C_8)$-alkylthio-$(C_1-C_8)$-alkyl, $(C_1-C_8)$-alkylsulphinyl-$(C_1-C_8)$-alkyl, $(C_1-C_8)$-alkylsulphonyl-$(C_1-C_8)$-alkyl, $(C_3-C_8)$-cycloalkyl, $(C_3-C_8)$-cycloalkenyl, $(C_3-C_8)$-cycloalkyl-$(C_1-C_8)$-alkyl, $(C_3-C_8)$-cycloalkenyl-$(C_1-C_8)$-alkyl, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, wherein all these residues are unsubstituted or substituted by one or more residues from the group consisting of halogen, nitro, hydroxyl, cyano, $(C_1-C_8)$-alkyl, $(C_1-C_8)$-haloalkyl, $(C_1-C_8)$-alkoxy, $(C_1-C_8)$-haloalkoxy, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, $R^{10}$, $R^{11}$ are each independently hydrogen, $(C_1-C_6)$-alkyl, $(C_2-C_6)$-alkenyl, $(C_2-C_6)$-alkynyl, $(C_3-C_6)$-cycloalkyl, ($C_3$-$C_6$)-cycloalkyl-($C_1$-$C_6$)-alkyl, phenyl, phenyl-($C_1$-$C_6$)-alkyl, pyridinyl, furanyl, thienyl, pyridinyl-($C_1$-$C_6$)-alkyl, thienyl-($C_1$-$C_6$)-alkyl, furanyl-($C_1$-$C_6$)-alkyl, heterocyclyl, heterocyclyl-($C_1$-$C_6$)-alkyl, wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $R^{10}$ and $R^{11}$, together with the sulphur atom to which they are attached, form a 3- to 6-membered unsaturated, partially saturated or saturated ring, which comprises in each case, in addition to the carbon atoms and in addition to the sulphur atom, p ring members from the group consisting of $N(R^{12})_m$, O and $S(O)_n$, and wherein all these residues are unsubstituted or substituted by one or more residues from the group consisting of halogen, nitro, hydroxyl, cyano, $NR^{13}R^{14}$, $C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl or ($C_1$-$C_6$)-alkylsulphonyl, $R^{12}$ is hydrogen, ($C_1$-$C_6$)-alkyl or ($C_1$-$C_6$)-alkylcarbonyl, $R^{13}$, $R^{14}$ are each independently hydrogen, ($C_1$-$C_6$)-alkyl, wherein these residues are unsubstituted or substituted by one or more residues from the group consisting of halogen, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, or $R^{13}$ and $R^{14}$, together with the nitrogen atom to which they are attached, form a 3- to 8-membered unsaturated, partially saturated or saturated ring, n is independently selected from 0, 1 or 2, m is independently selected from 0 or 1, p is independently selected from 0, 1, 2 or 3, q is independently selected from 0, 1 or 2, y is 0 or 1.

2. A compound of the formulae (G1) and (G2) and/or salt thereof according to claim 1 in which A is $CR^6R^7$, x is 0, 1 or 2, $R^1$ is hydrogen, ($C_3$-$C_6$)-cycloalkyl, ($C_3$-$C_6$)-cycloalkenyl, ($C_3$-$C_6$)-cycloalkyl-($C_1$-$C_6$)-alkyl, ($C_3$-$C_6$)-cycloalkenyl-($C_1$-$C_6$)-alkyl, phenyl, pyridinyl, furanyl, thienyl wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, $R^2$, $R^3$ are each independently hydrogen, ($C_1$-$C_6$)-alkoxyphenyl-($C_1$-$C_6$)-alkyl, ($C_1$-$C_6$)-alkylthiocarbonyl, ($C_1$-$C_6$)-haloalkylthiocarbonyl, ($C_1$-$C_6$)-alkoxy-($C_1$-$C_6$)-alkylcarbonyl, ($C_1$-$C_6$)-alkylthio-($C_1$-$C_6$)-alkylcarbonyl, ($C_1$-$C_6$)-alkylsulphinyl-($C_1$-$C_6$)-alkylcarbonyl, ($C_1$-$C_6$)-alkylsulphonyl-($C_1$-$C_6$)-alkylcarbonyl, ($C_1$-$C_6$)-alkylcarbonyl, ($C_1$-$C_6$)-haloalkylcarbonyl, ($C_2$-$C_6$)-alkenylcarbonyl, ($C_2$-$C_6$)-alkynylcarbonyl, ($C_1$-$C_6$)-alkoxycarbonyl-($C_1$-$C_6$)-alkylcarbonyl, ($C_1$-$C_6$)-alkoxycarbonyl, ($C_1$-$C_6$)-haloalkoxycarbonyl, ($C_2$-$C_6$)-alkenyloxycarbonyl, ($C_3$-$C_6$)-cycloalkylcarbonyl, ($C_3$-$C_6$)-cycloalkyl-($C_1$-$C_6$)-alkylcarbonyl, phenylcarbonyl, phenyl-($C_1$-$C_6$)-alkylcarbonyl, pyridinylcarbonyl, furanylcarbonyl, thienylcarbonyl, pyridinyl-($C_1$-$C_6$)-alkylcarbonyl, furanyl-($C_1$-$C_6$)-alkylcarbonyl, thienyl-($C_1$-$C_6$)-alkylcarbonyl, heterocyclylcarbonyl, heterocyclyl-($C_1$-$C_6$)-alkylcarbonyl, wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $NR^2R^3$ is —N=$S(O)_nR^{10}R^{11}$, $R^4$, $R^5$ are each independently hydrogen, formyl, oxytetrahydropyranmethyl, cyano, halogen, ($C_1$-$C_6$)-alkoxycarbonyl, ($C_1$-$C_6$)-alkoxy-($C_1$-$C_6$)-alkyl, ($C_1$-$C_6$)-alkylcarbonyloxy, ($C_1$-$C_6$)-alkylcarbonyloxy-($C_1$-$C_6$)-alkyl, ($C_1$-$C_6$)-alkyloxycarbonyloxy-($C_1$-$C_6$)-alkyl, $C_6$)-alkylsilyl, ($C_3$-$C_6$)-cycloalkyl-($C_1$-$C_6$)-alkyl, ($C_3$-$C_6$)-cycloalkyl, ($C_3$-$C_6$)-cycloalkenyl, ($C_2$-$C_6$)-alkynylcarbonyl, ($C_3$-$C_6$)-cycloalkyl-($C_1$-$C_6$)-alkylaminocarbonyl, ($C_2$-$C_6$)-alkenyl, aminocarbonyl, ($C_2$-$C_6$)-alkynyl, ($C_2$-$C_6$)-alkenylcarbonyl, imino-($C_1$-$C_6$)-alkyl, phenyl, pyridinyl, furanyl, thienyl, wherein all these residues are unsubstituted or substituted by one or more residues from the group consisting of halogen, hydroxyl, ($C_1$-$C_6$)-alkoxy, ($C_1$-$C_6$)-alkoxycarbonyl, ($C_1$-$C_6$)-alkoxycarbonyl-($C_1$-$C_6$)-alkoxy, ($C_3$-$C_6$)-cycloalkyl-($C_1$-$C_6$)-alkoxyimino, ($C_2$-$C_6$)-alkenyloxyimino, ($C_1$-$C_6$)-alkyloxyimino, aminocarbonyl, provided that $R^4$ and $R^5$ are not hydrogen at the same time, and wherein $R^4$ and $R^5$ together do not form an aromatic ring, $R^6$ is hydrogen, $R^7$ is hydrogen or ($C_1$-$C_6$)-alkyl, ($C_3$-$C_6$)-cycloalkyl, $R^{10}$, $R^{11}$ are each independently hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, phenyl, phenyl-($C_1$-$C_6$)-alkyl, pyridinyl, furanyl, thienyl, furanyl-($C_1$-$C_6$)-alkyl, heterocyclyl, heterocyclyl-($C_1$-$C_6$)-alkyl, wherein all these residues are unsubstituted or substituted by one or more residues from the group consisting of halogen, nitro, hydroxyl, cyano, $NR^{13}R^{14}$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, and wherein heterocyclyl has q oxo groups, and wherein each of the aforementioned heterocyclic residues, in addition to the carbon atoms, has in each case p ring members from the group consisting of $N(R^{12})_m$, O and $S(O)_n$, or $R^{10}$ and $R^{11}$, together with the sulphur atom to which they are attached, form a 3- to 6-membered unsaturated, partially saturated or saturated ring, which comprises in each case, in addition to the carbon atoms and in addition to the sulphur atom, p ring members from the group consisting of $N(R^{12})_m$, O and $S(O)_n$, and wherein all these residues are unsubstituted or substituted by one or more residues from the group consisting of halogen, nitro, hydroxyl, cyano, $NR^{13}R^{14}$, ($C_1$-$C_6$)- alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl or $(C_1-C_6)$-alkylsulphonyl, $R^{12}$ is hydrogen, $(C_1-C_6)$-alkyl or $(C_1-C_6)$-alkylcarbonyl, $R^{13}$, $R^{14}$ are each independently hydrogen, $(C_1-C_6)$-alkyl, wherein these residues are unsubstituted or substituted by one or more residues from the group consisting of halogen, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, or $R^{13}$ and $R^{14}$, together with the nitrogen atom to which they are attached, form a 3- to 8-membered unsaturated, partially saturated or saturated ring, n is 0, m is independently selected from 0 or 1, p is independently selected from 0 or 1, q is independently selected from 0 or 1, y is 0 or 1.

3. A compound of the formulae (G1) and (G2) and/or salts thereof according to claim 1 in which A is $CR^6R^7$, x is 0, 1 or 2, $R^1$ is hydrogen, cyclopropyl, cyclobutyl, cyclopentyl cyclohexyl or phenyl, wherein all these residues are unsubstituted or substituted by one or more residues from the group consisting of halogen, $R^2$, $R^3$ are each independently hydrogen, $(C_1-C_4)$-alkoxyphenyl-$(C_1-C_4)$-alkyl, $(C_1-C_4)$-alkylcarbonyl, $(C_1-C_4)$-haloalkylcarbonyl, $(C_2-C_5)$-alkenylcarbonyl, $(C_2-C_5)$-alkynylcarbonyl, $(C_1-C_4)$-alkoxycarbonyl, $(C_1-C_4)$-haloalkoxycarbonyl, $(C_1-C_4)$-alkoxy-$(C_1-C_4)$-alkylcarbonyl, $(C_1-C_4)$-haloalkoxy-$(C_1-C_4)$-alkylcarbonyl, $R^4$, $R^5$ are each independently hydrogen, formyl, oxytetrahydropyranmethyl, cyano, halogen, $(C_1-C_4)$-alkoxycarbonyl, $(C_1-C_4)$-alkoxy-$(C_1-C_4)$-alkyl, $(C_1-C_4)$-alkylcarbonyloxy-$(C_1-C_4)$-alkyl, $(C_1-C_4)$-alkylcarbonyloxy, $(C_1-C_6)$-alkyl, $(C_1-C_4)$-alkylsilyl, $(C_3-C_6)$-cycloalkyl-$(C_1-C_4)$-alkyl, $(C_3-C_6)$-cycloalkyl, $(C_3-C_6)$-cycloalkenyl, $(C_2-C_5)$-alkynylcarbonyl, $(C_3-C_6)$-cycloalkyl-$(C_1-C_4)$-alkylaminocarbonyl, $(C_2-C_6)$-alkenyl, aminocarbonyl, $(C_2-C_6)$-alkynyl, $(C_2-C_5)$-alkenylcarbonyl, $(C_1-C_4)$-alkoxycarbonylamino-$(C_1-C_4)$-alkyl, imino-$(C_1-C_4)$-alkyl, phenyl, pyridinyl, furanyl, thienyl, carboxythienyl, phenoxycarbonyl, wherein all these residues are unsubstituted or substituted by one or more residues from the group consisting of halogen, hydroxyl, $(C_1-C_4)$-alkoxy, $(C_1-C_4)$-alkyl, $(C_1-C_4)$-alkoxycarbonyl, $(C_1-C_4)$-alkoxycarbonyl-$(C_1-C_4)$-alkoxy, $(C_3-C_6)$-cycloalkyl-$(C_1-C_4)$-alkoxyimino, $(C_2-C_5)$alkenyloxyimino, $(C_1-C_4)$alkyloxyimino, aminocarbonyl, provided that $R^4$ and $R^5$ are not hydrogen at the same time, and wherein $R^4$ and $R^5$ together do not form an aromatic ring, $R^6$ is hydrogen, $R^7$ is hydrogen or methyl, y is 0 or 1.

4. An herbicidal and/or plant growth-regulating composition, wherein said composition comprises one or more compounds of the formulae (G1) or (G2) and/or salts thereof as defined in claim 1, and one or more further substances selected from groups (i) and/or (ii):

(i) one or more further agrochemically active substances, optionally selected from the group consisting of insecticides, acaricides, nematicides, further herbicides, fungicides, safeners, fertilizers and/or further growth regulators, (ii) one or more formulation auxiliaries customary in crop protection.

5. A product comprising one or more compounds of the formulae (G1) or (G2) and/or salts thereof according to claim 1 and/or a composition thereof for controlling one or more harmful plants or for regulating the growth of one or more plants.

6. A product comprising one or more compounds of the formulae (G1) or (G2) and/or salts thereof according to claim 1 and/or a composition thereof for controlling fungi.

7. A product comprising one or more compounds of the formulae (G1) or (G2) and/or salts thereof according to claim 1 and/or a composition thereof for controlling one or more pests.

8. A method for controlling fungi, one or more pests, one or more harmful plants or for regulating the growth of one or more plants, comprising applying an effective amount of one or more compounds of the formulae (G1) or (G2) and/or salts thereof, as defined in claim 1, or a composition thereof, to the plants, seeds of plants, soil in which or on which plants grow or an area under cultivation.

* * * * *